US008957192B2

(12) United States Patent
Schlom et al.

(10) Patent No.: US 8,957,192 B2
(45) Date of Patent: Feb. 17, 2015

(54) HUMAN CYTOTOXIC T-LYMPHOCYTE EPITOPE AND ITS AGONIST EPITOPE FROM THE NON-VARIABLE NUMBER OF TANDEM REPEAT SEQUENCE OF MUC-1

(75) Inventors: Jeffrey Schlom, Potomac, MD (US); Kwong-Yok Tsang, Bethesda, MD (US)

(73) Assignee: The United States of America, as represented by the Secretary Department of Health and Human Services, Washington, DC (US)

( * ) Notice: Subject to any disclaimer, the term of this patent is extended or adjusted under 35 U.S.C. 154(b) by 199 days.

(21) Appl. No.: 13/176,341

(22) Filed: Jul. 5, 2011

(65) Prior Publication Data

US 2011/0319869 A1    Dec. 29, 2011

Related U.S. Application Data

(62) Division of application No. 10/582,702, filed as application No. PCT/US2004/041921 on Dec. 10, 2004, now Pat. No. 7,999,071.

(60) Provisional application No. 60/529,329, filed on Dec. 12, 2003.

(51) Int. Cl.
| C07H 21/02 | (2006.01) |
| A61K 39/00 | (2006.01) |
| C07K 14/47 | (2006.01) |
| C07K 14/705 | (2006.01) |
| C12N 15/85 | (2006.01) |

(52) U.S. Cl.
CPC ......... *A61K 39/0011* (2013.01); *C07K 14/4727* (2013.01); *C07K 14/70596* (2013.01); *C12N 15/85* (2013.01); *A61K 2039/5154* (2013.01); *A61K 2039/5156* (2013.01); *A61K 2039/5158* (2013.01)
USPC ........................ 536/23.1; 536/23.5; 514/44 R

(58) Field of Classification Search
None
See application file for complete search history.

(56) References Cited

U.S. PATENT DOCUMENTS

| 5,759,808 A | 6/1998 | Casterman et al. |
| 5,827,666 A | 10/1998 | Finn et al. |
| 5,861,381 A | 1/1999 | Chambon et al. |
| 6,001,349 A | 12/1999 | Panicali et al. |
| 6,123,923 A | 9/2000 | Unger et al. |
| 6,319,496 B1 | 11/2001 | Panicali et al. |
| 6,328,969 B1 | 12/2001 | Houghton et al. |
| 6,407,063 B1 | 6/2002 | Luiten et al. |
| 6,514,942 B1 | 2/2003 | Ioannides et al. |
| 6,531,451 B1 | 3/2003 | Chaux et al. |
| 6,534,062 B2 | 3/2003 | Raz et al. |
| 6,548,068 B1 | 4/2003 | Schlom et al. |
| 6,576,896 B2 | 6/2003 | Figeys et al. |
| 6,600,012 B1 | 7/2003 | Agrawal et al. |
| 6,602,660 B1 | 8/2003 | Agrawal et al. |
| 6,716,627 B2 * | 4/2004 | Dobie .......................... 435/375 |
| 7,129,053 B1 | 10/2006 | Reiter et al. |
| 2003/0021770 A1 | 1/2003 | Schlom et al. |
| 2003/0180314 A1 | 9/2003 | DeGroot |
| 2003/0235868 A1 | 12/2003 | Hoogenboom et al. |
| 2004/0054137 A1 | 3/2004 | Thomson et al. |
| 2005/0042209 A1 | 2/2005 | Kufe et al. |
| 2008/0166367 A1 * | 7/2008 | Panicali et al. ............ 424/185.1 |

FOREIGN PATENT DOCUMENTS

| EP | 1336850 A1 | 8/2003 |
| WO | WO 00/06723 A1 | 2/2000 |
| WO | WO 01/18035 A2 | 3/2001 |
| WO | WO 01/24810 A1 | 4/2001 |
| WO | WO 01/27612 A2 | 4/2001 |
| WO | WO 01/90197 A1 | 11/2001 |
| WO | WO 02/060953 A2 | 8/2002 |
| WO | WO 02/083903 A2 | 10/2002 |
| WO | WO 03/099193 A2 | 12/2003 |
| WO | WO 2005/046614 A2 | 5/2005 |
| WO | WO 2005/046622 A2 | 5/2005 |

OTHER PUBLICATIONS

BLAST search (SwissProt Analysis): RID: 1063146772-12815-1701048.BLASTQ3, <http://www.ncbi.nlm.nih.gov/blast/Glast.cgi> (2003).
Brossart et al., "Identification of HLA-A2-restricted T-cell epitopes derived from the MUC1 tumor antigen for broadly applicable vaccine therapies," *Blood*, 93 (12), 4309-4317 (1999).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 111 (5 pt. 1), 2129-2138 (1990).
Carmon et al., "Novel breast-tumor-associated MUC1-derived peptides: characterization in Db-/-x beta2 microglobulin (beta2m) null mice transgenic for a chimeric HLA-A2.1/Db-beta2 microglobulin single chain," *Int. J. Cancer*, 84 (3), 391-397 (2000).
Gendler et al., "Molecular cloning and expression of human tumor-associated polymorphic epithelial mucin," *J. Biol. Chem.*, 265 (25), 15286-15293 (1990).
Hareuveni et al., "A transcribed gene, containing a variable number of tandem repeats, codes for a human epithelial tumor antigen. cDNA cloning, expression of the transfected gene and over-expression in breast cancer tissue," *Eur. J. Biochem.*, 189 (3), 475-486 (1990).
Heukamp et al., "Identification of three non-VNTR MUC1-derived HLA-A*0201-restricted T-cell epitopes that induce protective anti-tumor immunity in HLA-A2/K(b)-transgenic mice," *Int. J. Cancer*, 91 (3), 385-392 (2001).
Lan et al., "Cloning and sequencing of a human pancreatic tumor mucin cDNA," *J. Biol. Chem.*, 265 (25), 15294-15299 (1990).
Lazar et al., "Transforming growth factor alpha: mutation of aspartic acid 47 and leucine 48 results in different biological activities," *Mol. Cell Biol.*, 8 (3), 1247-1252 (1988).
Pietersz et al., "Definition of MHC-restricted CTL epitopes from non-variable number of tandem repeat sequence of MUC1," *Vaccine*, 18 (19), 2059-2071 (2000).

(Continued)

*Primary Examiner* — Mark Halvorson
(74) *Attorney, Agent, or Firm* — Leydig, Voit & Mayer, Ltd.

(57) ABSTRACT

Novel MUC-1 epitopes outside the VNTR region are identified. In addition, the first agonist epitope of MUC-1 is described. The employment of agonist epitopes in peptide, protein and vector-based vaccine may well aid in the development of effective vaccines for a range of human cancers.

22 Claims, 10 Drawing Sheets

(56) References Cited

OTHER PUBLICATIONS

Skolnick et al., "From genes to protein structure and function: novel applications of computational approaches in the genomic era," *Trends Biotechnol.*, 18 (1), 34-39 (2000).

Tsang et al., "A Human Cytotoxic T-Lymphocyte Epitope and Its Agonist Epitope from the Nonvariable Number of Tandem Repeat Sequence of MUC-1," *Clinical Cancer Research*, 10, 2139-2149 (2004).

*Japanese Journal of Gastroenterological Surgery*, 31(6), 1635, Abstract 11-34 (1998).

Japanese Patent Office Communication from Application No. 2006-544119 dated Dec. 13, 2011.

Sawai et al., *Journal of Shiga University Medical Science*, 14, 19-28 (1999).

* cited by examiner

| Virus | Designation | Promoters/Transgenes |
|---|---|---|
| rV-CEA(6D)/B7-1/ICAM-1/LFA-3 | rV-CEA(6D)/TRICOM | p40─CEA(6D)─p30─LFA-3─I3─ICAM-1─sE/L─B7-1 |
| rF-CEA(6D)/B7-1/ICAM-1/LFA-3 | rF-CEA(6D)/TRICOM | p40─CEA(6D)─p30─LFA-3─I3─ICAM-1─sE/L─B7-1 |
| rF-MUC-1/B7-1/ICAM-1/LFA-3 | rF-MUC-1/TRICOM | p40─MUC-1─p30─LFA-3─I3─ICAM-1─sE/L─B7-1 |
| rV-CEA(6D)/MUC-1(93L)/1/B7-1/ICAM-1/LFA-3 | rV-CEA/MUC/TRICOM | p40─CEA(6D)─sE/L─MUC-1(93L)─p30─LFA-3─I3─ICAM-1─sE/L─B7-1 |
| rF-CEA(6D)/MUC-1(93L)/1/B7-1/ICAM-1/LFA-3 | rF-CEA/MUC/TRICOM | p40─CEA(6D)─sE/L─MUC-1(93L)─p30─LFA-3─I3─ICAM-1─sE/L─B7-1 |

Figure 5

```
   1 ATGACACCGG GCACCCAGTC TCCTTTCTC CTGCTGCTGC TCCTCACAGT GCTTACAGTT
  61 GTTACGGGTT CTGGTCATGC AAGCTCTACC CCAGGTGGAG AAAGGAGAC TTGGCTACC
 121 CAGAGAAGTT CAGTGCCCAG CTCTACTGAG AAGAATGCTG TGAGTATGAC AAGCTCCGTA
 181 CTCTCCAGCC ACAGCCCCGG TTCAGGCTCC TCCACCACTC AGGGACAGGA TGTCACTCTG
 241 GCCCCGGCCA CGGAACCAGC TTCAGGTTCA GCTGCCTTGT GGGGACAGGA TGTCACCTCG
 301 GTACCAGTTA CTAGACCAGC TTTAGGTAGC ACAGCCACTC CTGCTCATGG AGTAACTAGT
 361 GCTCCTGATA CTCGTCCAGC TCCTGGCAGT ACTGCACCAC CGGCACATGG CGTAACATCA
 421 GCACCTGATA CAAGACCTGC ACCTGGATCT ACAGCGGCGC CTGCGCAGG AGTGACATCG
 481 GCGCCCGATA CGCGCCCCGC TCCCGGTAGC ACCGACCGC CGCCCCAGG TGTTACAAGT
 541 GCACCCGATA CCCGGCGGGC ACCGGAAGT ACCGTCCAC CTGCACAGG GGTCACAAGC
 601 GCGCCAGACA CTCGACCTGC GCCAGGGTCG ACTGCCCCTC CGGCGCATGG TGTGACCTCA
 661 GCTCCTGACA CAAGGCCAGC CCCAGCTAGC ACTCTGGTGC ACAACGGCAC CTCTGCCAGG
 721 GCTACCACAA CCCAGCCAG CAAGAGACACT CCATTCTCAA TTCCCAGCCA CCACTCTGAT
 781 ACTCCTACCA CCCTGCCAG CCATAGCACC AAGACTGATG CCAGTAGCAC TCACCATAGC
 841 ACGGTACCTC CTCTCACCTC CTCCAATCAC AGCACTTCTC CCCAGTTGTC TACTGGGGTC
 901 TCTTTCTTTT TCCTGTCTTT TCACATTTCA AACCTCCAGT TTAATTCCTC TCTGGAAGAT
 961 CCCAGCACCG ACTACTACCA AGAGCTGCAG AGAGACATTT CTGAAATGTT TTTGCAGATT
1021 TATAAACAAG GGGGTTTTCT GGGCCCTCC AATATTAAGT TCAGGCCAGG ATCTGTGTG
1081 GTACAATTGA CTCTGGCCTT CCGAGAAGGT ACCATCAATG TCCACGACGT GGAGACACAG
1141 TTCAATCAGT ATAAAACGGA AGCAGCCTCT CGATATAACC TGACGATCTC AGAGGTCAGC
1201 GTGAGTGATG TGCCATTCC TTTCTCTGCC CAGTCTGGGG CTGGGGTGCC AGGCTGGGGC
1261 ATCGCGCTGC TGGTGCTGGT CTGTGTCTG GTTGGCGTGG CCATTGTCTA TCTCATTGCC
1321 TTGGCTGTCT GTCAGTGCGG CCGAAAGAAC ACCTACCACA TACGGGCAGC TGGACATCTT
1381 GATACCTACC ATCCTATGAG CGAGTACCCC ACCTACCACA CCCATGGGCG CTATGTGCCC
1441 CCTAGCAGTA CCGATCGTAG CCCCTATGAG AAGGTTTCTG CAGGTAATGG TGGCAGCAGC
1501 CTCTCTTACA CAAACCCAGC AGTGGCCAGC ACTTGTAG
```

SEQUENCE OF wMUC-1(6)

MTPGTQSPFFLLLLTVLTVVTGSGHASSTPGGEKETSATQRSSVPSSTEKNAV
SMTSSVLSSHSPGSGSSTTQGQDVTLAPATEPASGSAALWGQDVTSVPVTRPAL
GSTAPPAHGVTSAPDTRPAPGSTAPPAHGVTSAPDTRPAPGSTAPPAHGVTSAP
DTRPAPGSTAPPAHGVTSAPDTRPAPGSTAPPAHGVTSAPDTRPAPGSTAPPAH
GVTSAPDTRPAPASTLVHNGTSARATTTPASKSTPFSIPSHHSDTPTTLASHST
KTDASSTHHSTVPPLTSSNHSTSPQLSTGVSFFFLSFHISNLQFNSSLEDPSTD
YYQELQRDISEMFLQIYKQGGFLGLSNIKFRPGSVVVQLTLAFREGTINVHDVE
TQFNQYKTEAASRYNLTISDVSVSDVPFPFSAQSGAGVPGWGIALLVLVCVLVA
LAIVYLIALAVCQCRRKNYGQLDIFPARDTYHPMSEYPTYHTHGRYVPPSSTDR
SPYEKVSAGNGGSSLSYTNPAVAATSANL

AMINO ACID SEQUENCE OF wMUC-16₍ᵣ₎

SEQUENCE LISTING

```
<160> NUMBER OF SEQ ID NOS: 42

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Ala Thr Trp Gly Gln Asp Val Thr Ser Val
1               5                   10

<210> SEQ ID NO 2
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 2

Ala Leu Trp Gly Gln Asp Val Thr Ser Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Ala Leu Leu Val Leu Val Cys Val Leu Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Thr Ile Ser Asp Val Ser Val Ser Asp Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Ala Leu Ala Ile Val Tyr Leu Ile Ala Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Val Leu Val Ala Leu Ala Ile Val Tyr Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Tyr Leu Ile Ala Leu Ala Val Cys Gln Cys
1               5                   10

<210> SEQ ID NO 8
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 8

Trp Gly Gln Asp Val Thr Ser Val Pro Val
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Arg Glu Gly Thr Ile Asn Val His Asp Val
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Gly Thr Gln Ser Pro Phe Phe Leu Leu Leu
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Leu Ala Phe Arg Glu Gly Thr Ile Asn Val
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Thr Leu Ala Ser His Ser Thr Lys Thr Asp
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Leu Gln Arg Asp Ile Ser Glu Met Phe Leu
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Synthetic
```

<400> SEQUENCE: 14

Ala Ile Trp Gly Gln Asp Val Thr Ser Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Ala Leu Trp Gly Gln Asp Val Thr Ser Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Ala Met Trp Gly Gln Asp Val Thr Ser Val
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Ala Met Trp Gly Gln Asp Val Thr Ser Leu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Ala Ile Trp Gly Gln Asp Val Thr Ser Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Ala Leu Trp Gly Gln Asp Val Thr Ser Val
1               5                   10

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
gccacctggg gacaggatgt cacctcggtc　　　　　　　　　　　　　　　30

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
gccctgtggg gacaggatgt cacctcggtc　　　　　　　　　　　　　　　30

<210> SEQ ID NO 22
<211> LENGTH: 30
<212> TYPE: DNA
<213> ORGANISM: Artificial Sequence
<220> FEATURE:
<223> OTHER INFORMATION: Synthetic

<400> SEQUENCE: 22
gccctgctgg tcctggtctg cgtcctggtc　　　　　　　　　　　　　　　30

<210> SEQ ID NO 23
<211> LENGTH: 30
<212> TYPE: DNA
<213> ORGANISM: Artificial Sequence
<220> FEATURE:
<223> OTHER INFORMATION: Synthetic

<400> SEQUENCE: 23
accatctcgg atgtctcggt ctcggatgtc　　　　　　　　　　　　　　　30

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
gccctggcca tcgtctacct gatcgccctg　　　　　　　　　　　　　　　30

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
gtcctggtcg ccctggccat cgtctacctg　　　　　　　　　　　　　　　30

<210> SEQ ID NO 26
<211> LENGTH: 30
<212> TYPE: DNA
<213> ORGANISM: Artificial Sequence
<220> FEATURE:
<223> OTHER INFORMATION: Synthetic

<400> SEQUENCE: 26
tacctgatcg ccctggccgt ctgccaatgc　　　　　　　　　　　　　　　30

<210> SEQ ID NO 27
<211> LENGTH: 30

```
<212> TYPE: DNA
<213> ORGANISM: Artificial Sequence
<220> FEATURE:
<223> OTHER INFORMATION: Synthetic

<400> SEQUENCE: 27
tggggacagg atgtcacctc ggtcccagtc                              30

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
agagaaggta ccatcaacgt ccacgatgtc                              30

<210> SEQ ID NO 29
<211> LENGTH: 30
<212> TYPE: DNA
<213> ORGANISM: Artificial Sequence
<220> FEATURE:
<223> OTHER INFORMATION: Synthetic

<400> SEQUENCE: 29
ggcacccagt ctcctttctt cctgctgctg                              30

<210> SEQ ID NO 30
<211> LENGTH: 30
<212> TYPE: DNA
<213> ORGANISM: Artificial Sequence
<220> FEATURE:
<223> OTHER INFORMATION: Synthetic

<400> SEQUENCE: 30
ctggccttca gagaaggtac catcaacgtc                              30

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
actctggcct cgcactcgac caagaccgat                              30

<210> SEQ ID NO 32
<211> LENGTH: 30
<212> TYPE: DNA
<213> ORGANISM: Artificial Sequence
<220> FEATURE:
<223> OTHER INFORMATION: Synthetic

<400> SEQUENCE: 32
ctgcaaagag atatctcgga aatgttcctg                              30

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
```
gccacttggg gacaggatgt cacctcggtc            30

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
gccctgtggg gacaggatgt cacctcgctg            30

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
gccatgtggg gacaggatgt cacctcggtc            30

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36
gccatgtggg gacaggatgt cacctcgctg            30

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
gccacttggg gacaggatgt cacctcgctg            30

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Tyr Leu Ser Gly Ala Asp Leu Asn Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Tyr Arg Pro Gly Glu Asn Leu Asn Leu
1               5

<210> SEQ ID NO 40
<211> LENGTH: 10

```
<212> TYPE: PRT
<213> ORGANISM: Artificial Sequence
<220> FEATURE:
<223> OTHER INFORMATION: Synthetic

<400> SEQUENCE: 40

Val Ile Ser Asn Asp Val Cys Ala Gln Val
1               5                   10

<210> SEQ ID NO 41
<211> LENGTH: 1548
<212> TYPE: DNA
<213> ORGANISM: Artificial Sequence
<220> FEATURE:
<223> OTHER INFORMATION: Synthetic

<400> SEQUENCE: 41
atgacaccgg gcacccagtc tcctttcttc ctgctgctgc tcctcacagt gcttacagtt      60
gttacgggtt ctggtcatgc aagctctacc ccaggtggag aaaaggagac ttcggctacc     120
cagagaagtt cagtgcccag ctctactgag aagaatgctg tgagtatgac aagctccgta     180
ctctccagcc acagccccgg ttcaggctcc tccaccactc agggacagga tgtcactctg     240
gccccggcca cggaaccagc ttcaggttca gctgccttgt ggggacagga tgtcacctcg     300
gtaccagtta ctagaccagc tttaggtagc acagcacctc ctgctcatgg agtaactagt     360
gctcctgata ctcgtccagc tcctggcagt actgcaccac cggcacatgg cgtaacatca     420
gcacctgata caagacctgc acctggatct acagcgccgc ctgcgcacgg agtgacatcg     480
gcgcccgata cgcgccccgc tcccggtagc accgcaccgc ccgcccacgg tgttacaagt     540
gcacccgata cccggccggc acccggaagt accgctccac ctgcacacgg ggtcacaagc     600
gcgccagaca ctcgacctgc gccagggtcg actgccccto cggcgcatgg tgtgacctca     660
gctcctgaca caaggccagc cccagctagc actctggtgc acaacggcac ctctgccagg     720
gctaccacaa ccccagccag caagagcact ccattctcaa ttcccagcca ccactctgat     780
actcctacca cccttgccag ccatagcacc aagactgatg ccagtagcac tcaccatagc     840
acggtacctc ctctcacctc ctccaatcac agcacttctc cccagttgtc tactgggtc      900 tctttctttt tcctgtcttt tcacatttca aacctccagt ttaattcctc tctggaagat     960
cccagcaccg actactacca agagctgcag agagacattt ctgaaatgtt tttgcagatt    1020
tataaacaag ggggttttct gggcctctcc aatattaagt tcaggccagg atctgtggtg    1080
gtacaattga ctctggcctt ccgagaaggt accatcaatg tccacgacgt ggagacacag    1140
ttcaatcagt ataaaacgga agcagcctct cgatataacc tgacgatctc agacgtcagc    1200
gtgagtgatg tgccatttcc tttctctgcc cagtctgggg ctggggtgcc aggctggggc    1260
atcgcgctgc tggtgctggt ctgtgttctg gttgcgctgg ccattgtcta tctcattgcc    1320
ttggctgtct gtcagtgccg ccgaaagaac tacgggcagc tggacatctt ccagcccgg     1380 gataccctacc atcctatgag cgagtacccc acctaccaca cccatgggcg ctatgtgccc    1440
cctagcagta ccgatcgtag cccctatgag aaggtttctg caggtaatgg tggcagcagc    1500
ctctcttaca caaacccagc agtggcagcc acttctgcca acttgtag                 1548

<210> SEQ ID NO 42
<211> LENGTH: 515
<212> TYPE: PRT
<213> ORGANISM: Artificial Sequence
<220> FEATURE:
<223> OTHER INFORMATION: Synthetic
```

<400> SEQUENCE: 42

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95

Asp Val Thr Ser Val Pro Val Thr Arg Pro Ala Leu Gly Ser Thr Ala
            100                 105                 110

Pro Pro Ala His Gly Val Thr Ser Ala Pro Asp Thr Arg Pro Ala Pro
        115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
210                 215                 220

Arg Pro Ala Pro Ala Ser Thr Leu Val His Asn Gly Thr Ser Ala Arg
225                 230                 235                 240

Ala Thr Thr Thr Pro Ala Ser Lys Ser Thr Pro Phe Ser Ile Pro Ser
                245                 250                 255

His His Ser Asp Thr Pro Thr Thr Leu Ala Ser His Ser Thr Lys Thr
            260                 265                 270

Asp Ala Ser Ser Thr His His Ser Thr Val Pro Pro Leu Thr Ser Ser
        275                 280                 285

Asn His Ser Thr Ser Pro Gln Leu Ser Thr Gly Val Ser Phe Phe
290                 295                 300

Leu Ser Phe His Ile Ser Asn Leu Gln Phe Asn Ser Ser Leu Glu Asp
305                 310                 315                 320

Pro Ser Thr Asp Tyr Tyr Gln Glu Leu Gln Arg Asp Ile Ser Glu Met
                325                 330                 335

Phe Leu Gln Ile Tyr Lys Gln Gly Gly Phe Leu Gly Leu Ser Asn Ile
            340                 345                 350

Lys Phe Arg Pro Gly Ser Val Val Val Gln Leu Thr Leu Ala Phe Arg
        355                 360                 365

Glu Gly Thr Ile Asn Val His Asp Val Glu Thr Gln Phe Asn Gln Tyr
370                 375                 380

Lys Thr Glu Ala Ala Ser Arg Tyr Asn Leu Thr Ile Ser Asp Val Ser
385                 390                 395                 400

Val Ser Asp Val Pro Phe Pro Phe Ser Ala Gln Ser Gly Ala Gly Val
```

```
                        405                 410                 415
Pro Gly Trp Gly Ile Ala Leu Leu Val Leu Val Cys Val Leu Val Ala
            420                 425                 430

Leu Ala Ile Val Tyr Leu Ile Ala Leu Ala Val Cys Gln Cys Arg Arg
            435                 440                 445

Lys Asn Tyr Gly Gln Leu Asp Ile Phe Pro Ala Arg Asp Thr Tyr His
        450                 455                 460

Pro Met Ser Glu Tyr Pro Thr Tyr His Thr His Gly Arg Tyr Val Pro
465                 470                 475                 480

Pro Ser Ser Thr Asp Arg Ser Pro Tyr Glu Lys Val Ser Ala Gly Asn
            485                 490                 495

Gly Gly Ser Ser Leu Ser Tyr Thr Asn Pro Ala Val Ala Ala Thr Ser
            500                 505                 510

Ala Asn Leu
        515
```

HUMAN CYTOTOXIC T-LYMPHOCYTE EPITOPE AND ITS AGONIST EPITOPE FROM THE NON-VARIABLE NUMBER OF TANDEM REPEAT SEQUENCE OF MUC-1

CROSS-REFERENCE TO RELATED APPLICATIONS

This patent application is a divisional of U.S. patent application Ser. No. 10/582,702, filed Apr. 23, 2007, now U.S. Pat. No. 7,999,071, which claims the benefit of U.S. Provisional Application No. 60/529,329, filed Dec. 12, 2003, which is incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 14,526 bytes ASCII (Text) file named "708183SeqListing_ST25.txt," created on Jul. 5, 2011.

FIELD OF THE INVENTION

CTL epitope sequences outside traditional MUC-1 immunogenic tumor antigens and HLA-anchor residues have been identified. In particular, the invention describes a method for T-cell activation by modifying HLA-anchor residues to provide a stronger immune response to native antigens associated with solid tumors, leukemias, or lymphomas.

BACKGROUND OF THE INVENTION

The tumor-associated antigen MUC-1, or DF-3/MUC-1, is overexpressed on the cell surface of many human adenocarcinomas such as ovarian, breast, pancreas, colorectal and prostate carcinoma, and hematological malignancies including multiple myeloma and some B-cell non-Hodgkin lymphomas. While MUC-1 is expressed on some normal epithelial tissue on lumenal surfaces, it has been demonstrated that the apical localization of MUC-1 is lost in tumor tissues. In addition, MUC-1 is under-glycosylated in human adenocarcinomas as compared with normal tissues and thus the antigenic epitopes of the protein core are more exposed. A high level of MUC-1 expression and secretion has also been shown to be associated with poor prognosis and high metastatic potential. It was initially demonstrated that histocompatibility complex (MHC)-unrestricted cytotoxic T cells could be established from subjects with pancreatic carcinoma, ovarian cancer and multiple myeloma; these T cells were shown to recognize the MUC-1 protein core in the 20 amino acid variable number of tandem repeat (VNTR)[2] region. While the VNTR region is immunogenic for MHC non-restricted CTL as well as for the production of MUC-1 specific antibodies, relatively limited information is available with respect to the immunogenicity of the region outside the VNTR.

Current treatment of cancers include radiation therapy and chemotherapy, which have particularly adverse effects on a subject undergoing such therapies.

Accordingly, there is a need for improved, safer treatments that have long-lasting protective effects for the prevention and treatment of tumors. In particular, there is a need for treatments that are more specific and less toxic than the currently available therapeutic agents.

SUMMARY OF THE INVENTION

The invention describes the identification and characterization of anti-tumor cytotoxic T lymphocyte (CTL) epitopes. In particular, MUC-1 CTL epitopes in the non-variable number of tandem repeat (VNTR) region extracellular region of MUC-1 are described. The VNTR is not a region of MUC-1, which is traditionally known to have immunogenic epitopes. The invention also describes the generation of enhancer agonist epitopes which generate stronger immune cell reaction than native peptides.

In a preferred embodiment, the invention provides an isolated nucleic acid molecule which encodes an agonist polypeptide antigen derived from a tumor antigen, such as for example, MUC-1, wherein the agonist polypeptide stimulates a stronger immune response as compared to a native polypeptide.

In another preferred embodiment, the agonist polypeptide binds to HLA molecules with a high avidity as compared to native polypeptides. Preferably, the agonist polypeptide has a higher association constant ($K_a$) for HLA molecules than a native polypeptide. Also preferably, the agonist polypeptide has a lower dissociation constant ($K_d$) for HLA molecules than a native polypeptide.

In another preferred embodiment, the nucleic acid molecule encodes an agonist polypeptide up to about 12 amino acids in length. Preferably, the agonist polypeptide is derived from a mucin tumor antigen.

In another preferred embodiment, the agonist polypeptide is derived from a non-variable number of tandem repeats region of MUC-1. Preferably, the agonist polypeptide generates an immune response.

In one aspect of the invention, the generated immune response is a cellular immune response. Cellular immune responses include cytotoxic T cell responses, T helper cell responses, and B cell immune responses.

In another preferred embodiment, the invention provides a nucleic acid molecule comprising a nucleic acid sequence corresponding to (i.e. that can code for) any one of the amino acid sequences as identified by SEQ ID NO: 1 through 19, fragments or variants thereof. SEQ ID NO: 1 through 19 are identified by:

| SEQ ID NO (peptide) | Peptide sequence | Nucleotide sequence | SEQ ID NO (n.t.) |
| --- | --- | --- | --- |
| 1 | ATWGQDVTSV | GCC/ACC/TGG/GGA/CAG/GAT/GTC/ACC/TCG/GTC | 20 |
| 2 | ALWGQDVTSV | GCC/CTG/TGG/GGA/CAG/GAT/GTC/ACC/TCG/GTC | 21 |
| 3 | ALLVLVCVLV | GCC/CTG/CTG/GTC/CTG/GTC/TGC/GTC/CTG/GTC | 22 |
| 4 | TISDVSVSDV | ACC/ATC/TCG/GAT/GTC/TCG/GTC/TCG/GAT/GTC | 23 |
| 5 | ALAIVYLIAL | GCC/CTG/GCC/ATC/GTC/TAC/CTG/ATC/GCC/CTG | 24 |

-continued

| SEQ ID NO (peptide) | Peptide sequence | Nucleotide sequence | SEQ ID NO (n.t.) |
|---|---|---|---|
| 6 | VLVALAIVYL | GTC/CTG/GTC/GCC/CTG/GCC/ATC/GTC/TAC/CTG | 25 |
| 7 | YLIALAVCQC | TAC/CTG/ATC/GCC/CTG/GCC/GTC/TGC/CAA/TGC | 26 |
| 8 | WGQDVTSVPV | TGG/GGA/CAG/GAT/GTC/ACC/TCG/GTC/CCA/GTC | 27 |
| 9 | REGTINVHDV | AGA/GAA/GGT/ACC/ATC/AAC/GTC/CAC/GAT/GTC | 28 |
| 10 | GTQSPFFLLL | GGC/ACC/CAG/TCT/CCT/TTC/TTC/CTG/CTG/CTG | 29 |
| 11 | LAFREGTINV | CTG/GCC/TTC/AGA/GAA/GGT/ACC/ATC/AAC/GTC | 30 |
| 12 | TLASHSTKTD | ACT/CTG/GCC/TCG/CAC/TCG/ACC/AAG/ACC/GAT | 31 |
| 13 | LQRDISEMFL | CTG/CAA/AGA/GAT/ATC/TCG/GAA/ATG/TTC/CTG | 32 |
| 14 | AIWGQDVTSV | GCC/ACT/TGG/GGA/CAG/GAT/GTC/ACC/TCG/GTC | 33 |
| 15 | ALWGQDVTSL | GCC/CTG/TGG/GGA/CAG/GAT/GTC/ACC/TCG/CTG | 34 |
| 16 | AMWGQDVTSV | GCC/ATG/TGG/GGA/CAG/GAT/GTC/ACC/TCG/GTC | 35 |
| 17 | AMWGQDVTSL | GCC/ATG/TGG/GGA/CAG/GAT/GTC/ACC/TCG/CTG | 36 |
| 18 | AIWGQDVTSL | GCC/ACT/TGG/GGA/CAG/GAT/GTC/ACC/TCG/CTG | 37 |
| 19 | ALWGQDVTSV | | |

In another preferred embodiment, the invention provides for a vector comprising an isolated nucleic acid molecule expressing any one of amino acids identified by SEQ ID NO: 1 through 19.

In another preferred embodiment, the vector comprises nucleic acid molecules encoding immune cell co-stimulatory molecules, such as for example, B7-1, ICAM-1 and LFA-3 31.

In yet another preferred embodiment, the invention provides for the transduction of dendritic cells with a vector comprising any one of the molecules as identified by SEQ ID NO: 1 through 19, fragments or variants thereof, and optionally, immune cell co-stimulatory molecules, such as for example, B7-1, ICAM-1 and LFA-3.35.

In one aspect of the invention, dendritic cells transduced with the vector comprising any one of the molecules as identified by SEQ ID NO: 1 through 19, fragments or variants thereof, and optionally, immune cell co-stimulatory molecules, generates an immune response, such as activation of a cytotoxic T cell response.

In another preferred embodiment, the invention provides a nucleic acid vector comprising one or more nucleic acid sequences encoding polypeptides as identified by any one of SEQ ID NO: 1 through 19, fragments or variants thereof, operably linked to an inducible promoter.

In another preferred embodiment the nucleic acid vector is a viral vector, plasmid and the like. Preferably the nucleic acid vector comprises an inducible promoter which is tissue specific, and optionally, immune cell co-stimulatory molecules.

In another preferred embodiment, the vector comprising a nucleic acid sequence encoding any one of the polypeptides identified by SEQ ID NO: 1 through 19.

In another preferred embodiment, the vector codes for any one of the polypeptides identified by any one of SEQ ID NO: 1 through 19 having a sequence identity to any one of SEQ ID NO: 1 through 19 of at least about 10%, more preferably, 25%, even more preferably a sequence identity of about 40%, 50%, 60%, 70%, 80%, 90%, or 99.9% to any of the SEQ ID NO: 1 through 19.

In another preferred embodiment, the vector contains a sequence identified by any one of SEQ ID NO: 20 through 37 having a sequence identity to anyone one of SEQ ID NO: 20 through 37 of at least about 10%, more preferably. More preferably, 25%, even more preferably about 40%, 50%, 60%, 70%, 80%, 90%, or 99.9% sequence identity to any one of SEQ ID NO: 30-37.

In another preferred embodiment, the invention provides a host cell expressing the polypeptide products of the vector as identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%. Preferably the host cell is an antigen presenting cell, such as for example, a monocyte/macrophage, dendritic cell or the like.

In another preferred embodiment, the invention provides a method for treating a subject suffering from or susceptible to a MUC-1 tumor comprising administering to a subject any one of the peptides identified by SEQ ID NO: 1 through 19, fragments or variants thereof.

In another preferred embodiment, the invention provides a method for treating a subject suffering from or susceptible to a MUC-1 tumor comprising administering to a subject any one of the nucleic acids identified by SEQ ID NO: 20 through 37, fragments or variants thereof.

In another preferred embodiment, the invention provides a method for generating an immune response to a MUC-1 tumor antigen comprising administering an isolated nucleic acid molecule in a therapeutically effective dose sufficient to generate a cellular immune response, wherein the isolated nucleic acid molecule encodes any one of polypeptides identified by SEQ ID NO: 1 through 19, fragments or variants thereof, and optionally immune cell co-stimulatory molecules. Preferably, the vector can express polypeptides as identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%.

In another preferred embodiment, the invention provides for a method for treating a subject suffering from or susceptible to a MUC-1 tumor comprising isolating dendritic cells from a subject suffering from cancer; and, treating the dendritic cells with one or more of the polypeptides identified by SEQ ID NO: 1 through 19; fragments, and variants thereof. Preferably, the treated dendritic cells are administered to the subject.

In another preferred embodiment, the invention provides a method for generating an immune response to a weakly immunogenic antigen comprising administering to an subject a polypeptide with a high avidity for HLA fused to the weak immunogen.

In one aspect of the invention, the polypeptide comprises the HLA binding fragment of SEQ ID NO: 19.

In another aspect of the invention, the weak immunogen is a differentiation antigen, or a tumor antigen.

In another preferred embodiment, the HLA binding fragment of SEQ ID NO: 19 is fused to a carcinoembryonic antigen, tumor antigen, self antigen, viral antigen and the like.

In another preferred embodiment, the invention provides for an isolated polypeptide comprising an amino acid sequence set forth in SEQ ID NO: 1 through 19, fragments or variants thereof.

In another preferred embodiment, the invention provides for a polypeptide identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%.

In one aspect of the invention, the polypeptide comprises SEQ ID NO: 19. Preferably, the polypeptide binds to HLA molecules with a high avidity and has a higher association constant ($K_a$) for the HLA than a native polypeptide and/or a lower dissociation constant ($K_d$) for the HLA than a native polypeptide.

In another aspect of the invention, the polypeptide is derived from a mucin tumor antigen, preferably, the polypeptide is derived from a non-variable number of tandem repeats region of MUC-1.

In another aspect of the invention, antigen presentation, by antigen presenting cells of the polypeptides induces an immune response, preferably a cellular immune response. For example, the cellular immune response is a cytotoxic T cell response, a T helper cell response, or a B cell immune response.

In another preferred embodiment, the invention provides for an agonist polypeptide comprising an amino acid sequence which is at least about 60% identical to the amino acid sequence of SEQ ID NO: 1 through 19, fragments, or variants thereof, more preferably, the agonist polypeptide comprises an amino acid sequence which is at least about 80% identical to the amino acid sequence of SEQ ID NO: 1 through 19, more preferably, the agonist polypeptide comprises an amino acid sequence which is at least about 90%, 95%, or 99.9% identical to the amino acid sequence of SEQ ID NO: 1 through 19.

In another preferred embodiment, a method of treating a subject suffering from or susceptible to a MUC-1 tumor is disclosed. The method may include the isolating dendritic cells from a subject suffering from cancer, treating the dendritic cells with one or more of polypeptides identified by SEQ ID NO: 1 through 19, activating peripheral blood mononuclear cells with the treated dendritic cells, and administering the activated PBMC cells to the subject.

Other aspects of the invention are described infra.

BRIEF DESCRIPTION OF THE FIGURES

FIG. 1A is a graph showing use of peptides at concentrations of 0-50 μg/ml. FIG. 1B is a graph showing use of peptides at concentrations of 0-12.5 μg/ml. P-92 MUC-1 peptide (open square), P-93L (closed square), P-93I (closed triangle). Results are expressed in mean fluorescence intensity (MFI).

FIG. 5 shows a schematic representation of certain viral constructs.

Figure 1A:
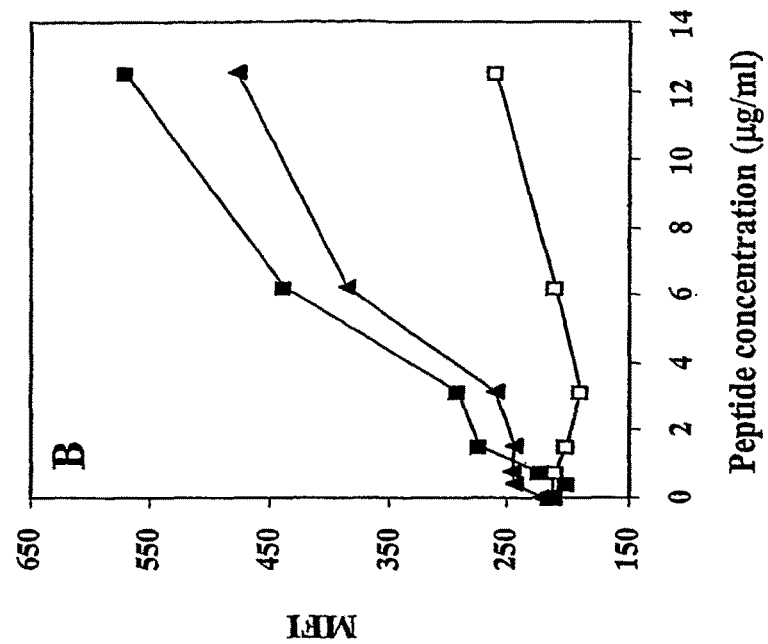
FIGS. 1A and 1B are graphs showing binding of MUC-1 peptide P-92 and the agonists P-93L and P-93I to HLA-A2 molecule.

TRICOM. Monoclonal antibodies COL-1 and DF-3 were used for the detection of CEA and MUC-1, respectively.

FIG. 9 is the nucleotide sequence of the wMUC-1(6) vector (SEQ ID NO: 41).

FIG. 10 is the amino acid sequence of wMUC-1(6) vector (SEQ ID NO: 42).

DETAILED DESCRIPTION OF THE INVENTION

We describe herein, inter alia, the identification of a novel class I HLA-A2 epitopes of MUC-1 that reside outside of the variable number of tandem repeat (VNTR) region that are important for immune based therapies in the treatment of cancer. We have demonstrated the ability of these epitopes to activate human T cells as measured by IFN-γ production. In particular, one epitope, ATWGQDVTSV (SEQ ID NO: 1), at amino acid position 92-101 and designated P-92), demonstrated the highest level of binding the HLA-A2 and which induced the highest level of IFN-γ in human T cells. The invention also provides for the generation of enhancer agonist epitopes, as identified by epitope, ALWGQDVTSV, (SEQ ID NO: 19; designated P-93L).

Virtually all tumors express multiple tumor-associated antigens and the vast majority of them are heterogeneously expressed in tumor masses. This has been shown to be attributable to inherent antigenic heterogeneity, environmental factors in the tumor milieu such as spatial configuration, or antigenic drift due to therapeutic intervention. Thus, vaccines expressing multiple transgenes may well help to alleviate this obstacle of antigenic heterogeneity. CEA is expressed on the vast majority of colorectal, pancreatic, and gastric tumors, and in approximately 70% of non-small-cell lung cancers, 50% of breast cancers, as well as other tumor types such as head and neck carcinoma and subsets of ovarian carcinoma (Thompson J A, Grunert F, Zimmermann, W. Carcinoembryonic antigen gene family: molecular biology and clinical perspectives. J Clin Lab Anal 1991; 5:344-66; and Robbins P F, Eggensperger D, Qi C F, Schlom J. Definition of the expression of the human carcinoembryonic antigen and non-specific cross-reacting antigen in human breast and lung carcinomas. Int J Cancer 1993; 53:892-7). MUC-1, on the other hand, is overexpressed on the vast majority of colorectal, pancreatic, breast and ovarian cancers as well as other carcinoma types (Kufe D, Inghirami G, Abe M. Differential reactivity of a novel monoclonal antibody (DF3) with human malignant versus benign breast tumors. Hybridoma 1984; 3:223-32; Burchell J, Gendler S, Taylor-Papadimitriou J, et al. Development and characterization of breast cancer reactive monoclonal antibodies directed to the core protein of the human milk mucin. Cancer Res 1987; 47: 5476-82; Zotter S, Hageman P C, Lossnitzer A, Mooi W J, Hilgers J. Tissue and tumor distribution of human polymorphic epithelial mucin. Cancer Rev 1988; 11-12: 55-101; Kotera Y, Fontenot J D, Pcher G, Metzgar R S, Finn O J. Humoral immunity against a tandem repeat epitope of human mucin MUC-1 in sera from breast, pancreatic, and colon cancer patients. Cancer Res 1994; 54:2856-60; and Goydos J S, Eler E, Whiteside T L, Finn O J, Lotze M T. A phase I trial of a synthetic mucin peptide vaccine. Induction of specific immune reactivity in patients with adenocarcinoma. J Surg Res 1996; 63:298-304). Thus, either individual or multi-targeting of these two antigens may prove advantageous for those cancer types expressing both antigens.

In certain embodiments the nucleic acid molecule does not have a sequence as described in FIG. 9.

In certain embodiments the peptide molecule does not have a sequence as described in FIG. 10.

In certain embodiments the nucleic acid molecule has a sequence as described in FIG. 9.

In certain embodiments the peptide molecule has a sequence as described in FIG. 10.

In certain embodiments the nucleic acid molecule does not have about a 30 nucleotide portion of consecutive nucleotides of a sequence as described in FIG. 9.

In certain embodiments the peptide molecule does not have about a 30 amino acid portion of consecutive amino acids of a sequence a sequence as described in FIG. 10.

In certain embodiments the nucleic acid molecule has a sequence as described in FIG. 9.

In certain embodiments the peptide molecule has a sequence as described in FIG. 10.

Figure 7:
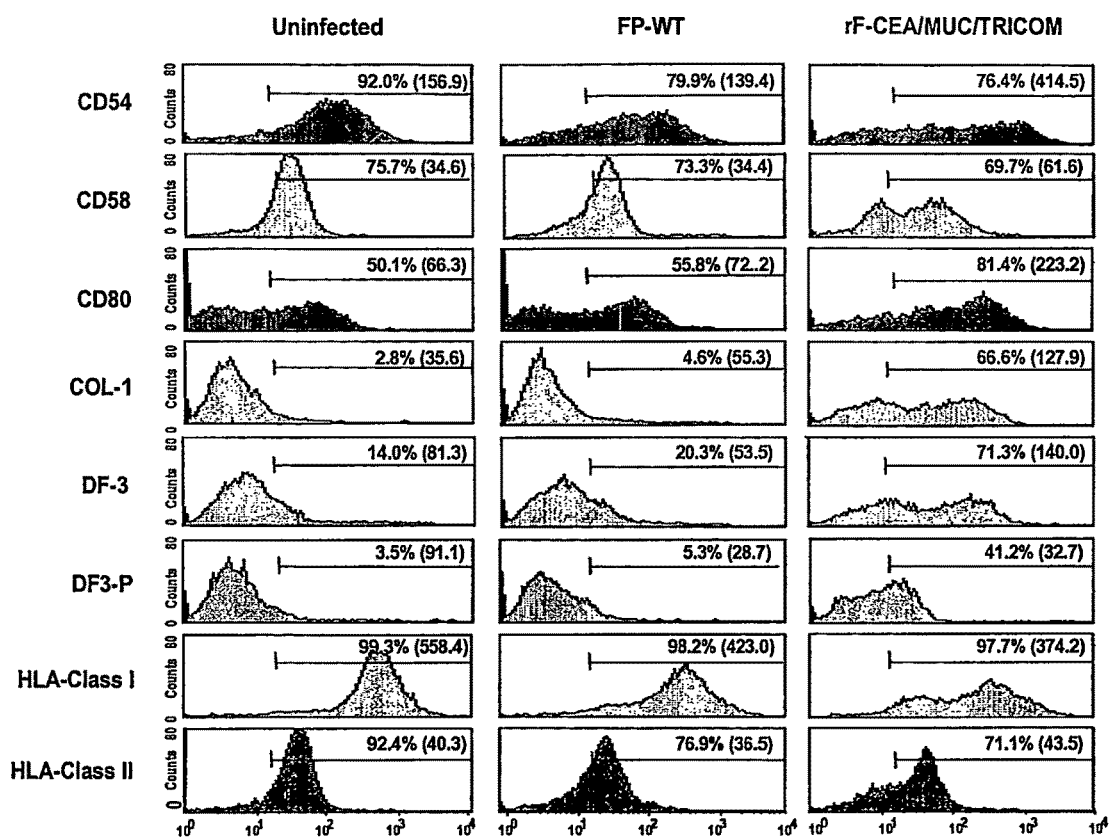
FIG. 7 is a graphical representation of a flow cytometric analysis of surface marker expression on human DCs uninfected, infected with control vector (FP-WT), or infected with rF-CEA/MUC/TRICOM. DCs (1×10⁶) were incubated in 1 ml of Opti-MEM medium at 37° C. with rF-CEA/MUC/TRICOM or control vector (FP-WT) for 2 hours, at an MOI of 40:1. The infected DCs were suspended in 10 ml of fresh, warm complete medium containing 100 ng/ml of rhGM-CSF and 20 ng/ml of rhIL-4, and then cultured for 24 h. Numbers in each histogram indicate the percentage of positive cells and the mean fluorescence intensity (in parentheses).

In certain embodiments the nucleic acid molecule does not have about a 30 nucleotide portion of consecutive nucleotides of a sequence a sequence as described in FIG. 7 and/or 8 of PCT Applications: PCT/US04/37810, filed Nov. 12, 2004 and PCT/US04/38643, filed Nov. 12, 2004.

In certain embodiments the nucleic acid molecule has a sequence as described in FIG. 7 and/or 8 of PCT Application: PCT/US04/37810, filed Nov. 12, 2004 and PCT/US04/38643, filed Nov. 12, 2004

In certain embodiments the nucleic acid molecule does not have about a 30 nucleotide portion of consecutive nucleotides of a sequence as described in PCT/US04/37810, filed Nov. 12, 2004 or PCT/US04/38643, filed Nov. 12, 2004.

In certain embodiments the nucleic acid molecule has a sequence as described in PCT/US04/37810, filed Nov. 12, 2004 or PCT/US04/38643, filed Nov. 12, 2004.

The following definitions of certain terms that are used herewith, are set forth below.

As used herein, "molecule" is used generically to encompass any vector, antibody, protein, drug and the like which are used in therapy and can be detected in a subject by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "administering a molecule to a cell" (e.g., an expression vector, nucleic acid, cytokines, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

The term "or" may be inclusive or exclusive.

A "genetic modification" refers to any addition, deletion or disruption to a cell's normal nucleotides. Any method which can achieve the genetic modification of APCs are within the spirit and scope of this invention. Art recognized methods include viral mediated gene transfer, liposome mediated transfer, transformation, transfection and transduction.

The terms "nucleic acid molecule" or "polynucleotide" will be used interchangeably throughout the specification, unless otherwise specified. As used herein, "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

It must be noted that as used herein and in the appended claims, the singular forms "a," "an," and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

As used herein, the term "fragment or segment," as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A "vector" is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

"Transcriptional regulatory sequence" is a generic term used throughout the specification to refer to DNA sequences, such as initiation signals, enhancers, promoters, silencing elements, which induce, inhibit or control transcription of protein coding sequences with which they are operably linked.

As used herein, the term "downstream" when used in reference to a direction along a nucleotide sequence means in the direction from the 5' to the 3' end. Similarly, the term "upstream" means in the direction from the 3' to the 5' end.

As used herein, the term "gene" means the gene and all currently known variants thereof and any further variants which may be elucidated.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target genes. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The resulting polypeptides generally will have significant amino acid identity relative to each other. A polymorphic variant is a variation in the polynucleotide sequence of a particular gene between subjects of a given species. Polymorphic variants also may encompass "single nucleotide polymorphisms" (SNPs,) or single base mutations in which the polynucleotide sequence varies by one base.

The terms, "complementary" or "complements" are used interchangeably throughout and mean that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

The term "substantial sequence identity", when used in connection with peptides/amino acid sequences, refers to peptides/amino acid sequences, which are substantially identical to or similar in sequence, giving rise to a sequence identity in conformation and thus to similar biological activity. The term is not intended to imply a common evolution of the sequences.

Typically, peptides/amino acid sequences having "substantial sequence identity" are sequences that are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

To determine the percent sequence identity of two peptides/amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). For example, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "sequence identity"). The percent identity between the two sequences is a function of the number of identical positions shared by the sequences, taking into account the number of gaps, and the length of each gap, which need to be introduced for optimal alignment of the two sequences.

The terms "protein" and "polypeptide" are used interchangeably herein. The term "peptide" is used herein to refer to a chain of two or more amino acids or amino acid analogs (including non-naturally occurring amino acids), with adjacent amino acids joined by peptide (—NHCO—) bonds. Thus, the peptides of the invention include oligopeptides, polypeptides, proteins, mimetopes and peptidomimetics. Methods for preparing mimetopes and peptidomimetics are known in the art.

The terms "mimetope" and "peptidomimetic" are used interchangeably herein. A "mimetope" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) Science 260:1937-1942) and "retro-inverso" peptides (see U.S. Pat. No. 4,522,752 to Sisto). The terms "mimetope" and "peptidomimetic" also refer to a moiety, other than a naturally occurring amino acid, that conformationally and functionally serves as a substitute for a particular amino acid in a peptide-containing compound without adversely interfering to a significant extent with the function of the peptide. Examples of amino acid mimetics include D-amino acids. Peptides substituted with one or more D-amino acids may be made using well known peptide synthesis procedures. Additional substitutions include amino acid analogs having variant side chains with functional groups, for example, b-cyanoalanine, canavanine, djenkolic acid, norleucine, 3-phosphoserine, homoserine, dihydroxyphenylalanine, 5-hydroxytryptophan, 1-methylhistidine, or 3-methylhistidine As used herein an "analog" of a compound X refers to a compound which retains chemical structures of X necessary for functional activity of X, yet which also contains certain chemical structures which differ from X. An example of an analog of a naturally-occurring peptide is a peptide which includes one or more non-naturally-occurring amino acids. The term "analog" is also intended to include modified mimetopes and/or peptidomimetics, modified peptides and polypeptides, and allelic variants of peptides and polypeptides. Analogs of a peptide will therefore produce a peptide analog that is substantially homologous or, in other words, has substantial sequence identity to the original peptide. The term "amino acid" includes its art recognized meaning. Preferred amino acids include the naturally occurring amino acids, as well as synthetic derivatives, and amino acids derived from proteins, e.g., proteins such as casein, i.e., casamino acids, or enzymatic or chemical digests of, e.g., yeast, an animal product, e.g., a meat digest, or a plant product, e.g., soy protein, cottonseed protein, or a corn steep liquor (see, e.g., Traders' Guide to Fermentation Media, Traders Protein, Memphis, Tenn. (1988), Biotechnology: A Textbook of Industrial Microbiology, Sinauer Associates, Sunderland, Mass. (1989), and Product Data Sheet for Corn Steep Liquor, Grain Processing Corp., IO).

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

A "heterologous" component refers to a component that is introduced into or produced within a different entity from that in which it is naturally located. For example, a polynucleotide derived from one organism and introduced by genetic engineering techniques into a different organism is a heterologous polynucleotide that if expressed can encode a heterologous polypeptide. Similarly, a promoter or enhancer that is removed from its native coding sequence and operably linked to a different coding sequence is a heterologous promoter or enhancer. Possible alternative terminology includes "foreign" or "exogenous". A heterologous nucleotide sequence may encode a sequence of amino acids, i.e. a peptide or a polypeptide.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or subject sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or subject sources). A number of polynucleotides comprising promoter sequences (such as the commonly-used CMV promoter) also comprise enhancer sequences.

"Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

As used herein, a "target cell" or "recipient cell" refers to an subject cell or cell which is desired to be, or has been, a recipient of exogenous nucleic acid molecules, polynucleotides and/or proteins. The term is also intended to include progeny of a single cell.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, "homologous recombination" means a nucleotide sequence on one vector is homologous to a nucleotide sequence on another vector. Using restriction enzymes to cut the two sequences and ligating the two sequences results in the two vectors combining. Typically, several kilobases of unaltered flanking DNA (both at the 5' and 3' ends) are included in the vector (see, e.g., Thomas and Capecchi, Cell, 51:503 (1987) for a description of homologous recombination vectors).

Homologous nucleic acid sequences, when compared, exhibit significant sequence identity or similarity. The standards for sequence identity in nucleic acids are either measures for sequence identity generally used in the art by sequence comparison or based upon hybridization conditions. The hybridization conditions are described in greater detail below.

Sequence homology and sequence identity are used interchangeably herein.

"Stringency" is meant the combination of conditions to which nucleic acids are subject that cause the duplex to dissociate, such as temperature, ionic strength, and concentration of additives such as formamide. Conditions that are more likely to cause the duplex to dissociate are called "higher stringency", e.g. higher temperature, lower ionic strength and higher concentration of formamide.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C.

For certain applications, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

The phrase "hybridizing conditions" and its grammatical equivalents, when used with a maintenance time period, indicates subjecting the hybridization reaction admixture, in context of the concentration of the reactants and accompanying reagents in the admixture, to time, temperature, pH conditions sufficient to allow the polynucleotide probe to anneal with the target sequence, typically to form the nucleic acid duplex. Such time, temperature and pH conditions required to accomplish the hybridization depend, as is well known in the art on the length of the polynucleotide probe to be hybridized, the degree of complementarity between the polynucleotide probe and the target, the guanidine and cytosine content of the polynucleotide, the stringency of the hybridization desired, and the presence of salts or additional reagents in the hybridization reaction admixture as may affect the kinetics of hybridization. Methods for optimizing hybridization conditions for a given hybridization reaction admixture are well known in the art.

As used herein, "substantial sequence identity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial sequence identity exists when the segments will hybridize under selective hybridization conditions, to a strand, or its complement, typically using a fragment derived from SEQ ID NO: 1. Typically, selective hybridization will occur when there is at least about 55% sequence identity over a stretch of at least about 14 nucleotides, preferably at least about 65%, more preferably at least about 75%, and most preferably at least about 90%. See Kanehisa (1984) *Nuc. Acids Res.* 12:203-213. The length of sequence identity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations. In determining sequence identity or percent homology the below discussed protocols and programs for sequence similarity are suitably employed including the BLAST algorithm.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The nucleic acid and protein sequences of the present invention can further be used as a "query sequence" to perform a search against public databases to identify, for example, other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., XBLAST and NBLAST) can be used. See www.ncbi.nlm.nih.gov.

Sequence similarity searches can be also performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for sequence identity searching, gene finding, multiple sequence alignment, secondary structure prediction, and motif identification. GeneThesaurus 1.0™ is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

As used herein, the term "specifically hybridizes" or "specifically detects" refers to the ability of a nucleic acid molecule to hybridize to at least approximately 6 consecutive nucleotides of a sample nucleic acid.

"Substantially purified" refers to nucleic acid molecules or proteins that are removed from their natural environment and are isolated or separated, and are at least about 60% free, preferably about 75% free, and most preferably about 90% free, from other components with which they are naturally associated.

An "antigen" is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to, an MHC molecule or T cell receptor. "Antigen processing" refers to the degradation of an antigen into fragments (e.g., the degradation of a protein into peptides) and the association of one or more of these fragments (e.g., via binding) with MHC molecules for presentation by "antigen-presenting cells" to specific T cells.

"Dendritic cells" (DC) are potent antigen-presenting cells, capable of triggering a robust adaptive immune response in vivo. It has been shown that activated, mature DC provide the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. The second type of signal, called a co-stimulatory signal, is neither antigen-specific nor MHC-restricted, and can lead to a full proliferation response of T cells and induction of T cell effector functions in the presence of the first type of signals. This two-fold signaling can, therefore, result in a vigorous immune response. As noted supra, in most non-avian vertebrates, DC arise from bone marrow-derived precursors. Immature DC are found in the peripheral blood and cord blood and in the thymus. Additional immature populations may be present elsewhere. DC of various stages of maturity are also found in the spleen, lymph nodes, tonsils, and human intestine. Avian DC may also be found in the bursa of Fabricius, a primary immune organ unique to avians. In a preferred embodiment, the dendritic cells of the present invention are mammalian, preferably human, mouse, or rat.

A "co-stimulatory molecule" encompasses any single molecule or combination of molecules which, when acting together with a peptide/MHC complex bound by a T cell receptor on the surface of a T cell, provides a co-stimulatory effect which achieves activation of the T cell that binds the peptide.

As used herein, "immunoreceptors" will refer to class I MHC (HLA-A, -B, -C, -G) and the like) and other immune related receptors, such as for example Gp49, PIR, PIRA, PIRB, LIR, NKR-P1, NKp46, Digr1, ILT, MIR, KIR and the like. MHC may also include other classes such as MHC class II and MHC class III, derivatives and mutants thereof. The human MHC complex is also called the human leukocyte antigen (HLA) complex. MHC antigens are divided into MHC class I antigens (in humans, this class includes HLA-A, -B, and -C antigens) and MHC class II antigens (in humans, this class includes HLA-DP, -DQ, and -DR antigens). Thus, the terms "MHC-II antigens", "MHC class II antigens", and "MHC class II transplantation antigens" are used interchangeably herein to refer to the class of proteins, which in humans, includes HLA-DP, -DQ and -DR antigens. While the terms "MHC class II genes" and "MHC-II genes" are used interchangeably herein to refer to the genes which encode the MHC class II transplantation antigens. The term "MHC-II" is used herein to refer to the gene locus which encodes the MHC class II transplantation antigens, as well as the group of proteins encoded by that locus. Transplantation antigens also include cell surface molecules other than MHC class I and II antigens. These antigens include the following: (1) the ABO antigens involved in blood cell recognition; (2) cell adhesion molecules such as ICAM, which is involved in leukocyte cell-cell recognition; and (3) β2-microglobulin, a polypeptide associated with the 44 kd heavy chain polypeptide that comprises the HLA-I antigens but is not encoded by the MHC complex. HLA haplotypes/allotypes vary from subject to subject and it is often helpful to determine the subject's HLA type. The HLA type may be determined via standard typing procedures and the peripheral blood lymphocytes (PBLs) purified by Ficoll gradients.

"Diagnostic" or "diagnosed" means identifying the presence or nature of a pathologic condition. Diagnostic methods differ in their sensitivity and specificity. The "sensitivity" of a diagnostic assay is the percentage of diseased subjects who test positive (percent of "true positives"). Diseased subjects not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "subject" or "subject" are used interchangeably herein, and is meant a mammalian subject to be treated, with human subjects being preferred. In some cases, the methods of the invention find use in experimental animals, in veterinary application, and in the development of animal models for disease, including, but not limited to, rodents including mice, rats, and hamsters; and primates.

"Label molecules" are chemical or biochemical moieties used for labeling a polynucleotide, a polypeptide, or an antibody. They include, but are not limited to, radionuclides, enzymes, substrates, cofactors, inhibitors, fluorescent agents, chromogenic agents, chemiluminescent agents, magnetic particles, and the like. Reporter molecules specifically bind, establish the presence of, and allow quantification of a particular polynucleotide, polypeptide, or antibody.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

As used herein, "fresh tumors" refer to tumors removed from a host by surgical or other means.

As used herein, "proliferative growth disorder, "neoplastic disease," "tumor", "cancer" are used interchangeably as used herein refers to a condition characterized by uncontrolled, abnormal growth of cells. Preferably the cancer to be treated is MUC-1 positive cancer and the abnormal proliferation of cells can be any cell in the organ. Examples of cancer include but are not limited to, carcinoma, blastoma, and sarcoma. As used herein, the term "carcinoma" refers to a new growth that arises from epithelium, found in skin or, more commonly, the lining of body organs.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "in need of such treatment" as used herein refers to a judgment made by a care giver such as a physician, nurse, or nurse practitioner in the case of humans that a subject requires or would benefit from treatment. This judgment is made based on a variety of factors that are in the realm of a care giver's expertise, but that include the knowledge that the subject is ill, or will be ill, as the result of a condition that is treatable by the compositions of the invention.

"Cells of the immune system" or "immune cells" as used herein, is meant to include any cells of the immune system that may be assayed, including, but not limited to, B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, macrophage, activation, B-cell activation) or for the cytokines they produce.

The term "activated T cell," as used herein, refers to a T cell that expresses antigens indicative of T-cell activation (that is, T cell activation markers). Examples of T cell activation markers include, but are not limited to, CD25, CD26, CD30, CD38, CD69, CD70, CD71, ICOS, OX-40 and 4-1BB. The expression of activation markers can be measured by techniques known to those of skill in the art, including, for example, western blot analysis, northern blot analysis, RT-PCR, immunofluorescence assays, and fluorescence activated cell sorter (FACS) analysis.

The term "resting T cell," as used herein, refers to a T cell that does not express T-cell activation markers. Resting T cells include, but are not limited to, T cells which are $CD25^-$, $CD69^-$, $ICOS^-$, $SLAM^-$, and $4\text{-}1BB^-$. The expression of these markers can be measured by techniques known to those of skill in the art, including, for example, western blot analysis, northern blot analysis, RT-PCR, immunofluorescence assays, and fluorescence activated cell sorter (FACS) analysis.

"CD4" is a cell surface protein important for recognition by the T cell receptor of antigenic peptides bound to MHC class II molecules on the surface of an APC. Upon activation, naïve CD4 T cells differentiate into one of at least two cell types, Th1 cells and Th2 cells, each type being characterized by the cytokines it produces. "Th1 cells" are primarily involved in activating macrophages with respect to cellular immunity and the inflammatory response, whereas "Th2 cells" or "helper T cells" are primarily involved in stimulating B cells to produce antibodies (humoral immunity). CD4 is the receptor for the human immunodeficiency virus (HIV). Effector molecules for Th1 cells include, but are not limited to, IFN-γ, GM-CSF, TNF-α, CD40 ligand, Fas ligand, IL-3, TNF-β, and IL-2. Effector molecules for Th2 cells include, but are not limited to, IL-4, IL-5, CD40 ligand, IL-3, GS-CSF, IL-10, TGF-β, and eotaxin. Activation of the Th1 type cytokine response can suppress the Th2 type cytokine response.

"CD8" is a cell surface protein important for recognition by the T cell receptor of antigenic peptides bound to MHC class I molecules. CD8 T cells usually become "cytotoxic T cells" or "killer T cells" and activate macrophages. Effector molecules include, but are not limited to, perforin, granzymes, Fas ligand, IFN-γ, TNF-α, and TNF-β.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein comprising epitope A (or free, unlabeled A) in a reaction comprising labeled "A" and the antibody will reduce the amount of labeled A bound to the antibody. "Specific binding" in general, refers to any immune related molecule binding to its ligand, such as for example the binding of a T cell receptor expressed by a T lymphocyte, to an MHC molecule and peptide on an antigen presenting cell.

"Activity," "activation," or "augmentation" is the ability of immune cells to respond and exhibit, on a measurable level, an immune function. Measuring the degree of activation refers to a quantitative assessment of the capacity of immune cells to express enhanced activity when further stimulated as a result of prior activation. The enhanced capacity may result from biochemical changes occurring during the activation process that allow the immune cells to be stimulated to activity in response to low doses of stimulants.

Immune cell activity that may be measured include, but is not limited to, (1) cell proliferation by measuring the cell or DNA replication; (2) enhanced cytokine production, including specific measurements for cytokines, such as IFN-γ, GM-CSF, or TNF-α; (3) cell mediated target killing or lysis; (4)

cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

An "adjuvant" is any substance capable of enhancing the immune response to an antigen with which it is mixed. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol, as well as BCG (bacilli Calmette-Guerin) and *Corynabacterium parvum*, which are often used in humans, and ligands of CCR6 and other chemokine receptors.

A "chemokine" is a small cytokine involved in the migration and activation of cells, including phagocytes and lymphocytes, and plays a role in inflammatory responses. Three classes of chemokines have been defined by the arrangement of the conserved cysteine (C) residues of the mature proteins: the CXC or α chemokines that have one amino acid residue separating the first two conserved cysteine residues; the CC or β chemokines in which the first two conserved cysteine residues are adjacent; the C or γ chemokines which lack two (the first and third) of the four conserved cysteine residues. Within the CXC subfamily, the chemokines can be further divided into two groups. One group of the CXC chemokines have the characteristic three amino acid sequence ELR (glutamic acid-leucine-arginine) motif immediately preceding the first cysteine residue near the amino terminus. A second group of CXC chemokines lack such an ELR domain. The CXC chemokines with the ELR domain (including IL-8, GROα/β/γ, mouse KC, mouse MIP-2, ENA-78, GCP-2, PBP/CTAPIII/β-TG/NAP-2) act primarily on neutrophils as chemoattractants and activators, inducing neutrophil degranulation with release of myeloperoxidase and other enzymes. The CXC chemokines without the ELR domain (e.g., IP-10/mouse CRG, Mig, PBSF/SDF-1, PF4), the CC chemokines (e.g., MIP-1α, MIP-1β, RANTES, MCP-1/2/3/4/mouse JE/mouse MARC, eotaxin, I-309/TCA3, HCC-1, C10), and the C chemokines (e.g., lymphotactin), chemoattract and activate monocytes, dendritic cells, T-lymphocytes, natural killer cells, B-lymphocytes, basophils, and eosinophils.

A "cytokine" is a protein made by a cell that affect the behavior of other cells through a "cytokine receptor" on the surface of the cells the cytokine effects. Cytokines manufactured by lymphocytes are sometimes termed "lymphokines." Examples of cytokines include interleukins, interferons and the like.

By "immunologically effective" is meant an amount of the peptide or fragment thereof which is effective to activate an immune response to prevent or treat proliferative cell growth disorders, such as cancer. Obviously, such amounts will vary between species and subjects depending on many factors. For example, higher doses will generally be required for an effective immune response in a human compared with a mouse.

As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

An "epitope", as used herein, is a portion of a polypeptide that is recognized (i.e., specifically bound) by a B-cell and/or T-cell surface antigen receptor. Epitopes may generally be identified using well known techniques, such as those summarized in Paul, Fundamental Immunology, 3rd ed., 243-247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

As used herein, the term "agonist polypeptide" refers to epitopes in the polypeptide which activate a stronger immune response than a native polypeptide. Examples of differences in properties between an agonist polypeptide versus a native polypeptide include, but not limited to a) binding HLA molecules at lower peptide concentrations, (b) demonstrate a higher avidity for HLA molecules in dissociation assays, (c) when used with antigen-presenting cells induce the production of more IFN-γ by T cells derived with the use of the native peptide. Increased or augmented immune response are measured as described above.

As used herein, "native polypeptide" refers to a polypeptide as found in its natural environment. For example, a native MUC-1 tumor antigen is expressed by a tumor cell in a subject.

In a preferred embodiment, agonist polypeptides generate stronger immune responses, as compared to the native polypeptide. For example, compared with the native P-92 peptide, agonist polypeptides (a) bind HLA-A2 at lower peptide concentrations, (b) demonstrate a higher avidity for HLA-A2 in dissociation assays, (c) when used with antigen-presenting cells induce the production of more IFN-γ by T cells derived with the use of the native peptide, and (d) were capable of more efficiently generating MUC-1-specific human T-cell lines from normal volunteers and pancreatic cancer subjects. Most importantly, the T-cell lines generated using the agonist epitope were more efficient than those generated with the native epitope, in the lysis of targets pulsed with the native epitope and in the lysis of HLA-A2 human tumor cells expressing MUC-1.

In another preferred embodiment, subjects, suffering from or susceptible to tumors, infectious diseases and the like are treated with autologous antigen presenting cells, such as for example dendritic cells (DCs), that have been transduced with polypeptide antigen derived from a tumor antigen, such as for example, MUC-1, wherein the agonist polypeptide stimulates a stronger immune response as compared to a native polypeptide. Other examples of tumor antigens, include, but are not limited to HER2/neu, carcinoembryonic antigen (CEA), p53.

In another preferred embodiment, the invention provides a nucleic acid molecule comprising a nucleic acid sequence corresponding to any one of the amino acid sequences as identified by SEQ ID NO: 1 through 19, fragments or variants thereof. SEQ ID NO: 1 through 19 are identified by

| SEQ ID NO (peptide) | Peptide sequence | Nucleotide sequence | SEQ ID NO (n.t.) |
|---|---|---|---|
| 1 | ATWGQDVTSV | GCC/ACC/TGG/GGA/CAG/GAT/GTC/ACC/TCG/GTC | 20 |
| 2 | ALWGQDVTSV | GCC/CTG/TGG/GGA/CAG/GAT/GTC/ACC/TCG/GTC | 21 |
| 3 | ALLVLVCVLV | GCC/CTG/CTG/GTC/CTG/GTC/TGC/GTC/CTG/GTC | 22 |
| 4 | TISDVSVSDV | ACC/ATC/TCG/GAT/GTC/TCG/GTC/TCG/GAT/GTC | 23 |
| 5 | ALAIVYLIAL | GCC/CTG/GCC/ATC/GTC/TAC/CTG/ATC/GCC/CTG | 24 |
| 6 | VLVALAIVYL | GTC/CTG/GTC/GCC/CTG/GCC/ATC/GTC/TAC/CTG | 25 |
| 7 | YLIALAVCQC | TAC/CTG/ATC/GCC/CTG/GCC/GTC/TGC/CAA/TGC | 26 |
| 8 | WGQDVTSVPV | TGG/GGA/CAG/GAT/GTC/ACC/TCG/GTC/CCA/GTC | 27 |
| 9 | REGTINVHDV | AGA/GAA/GGT/ACC/ATC/AAC/GTC/CAC/GAT/GTC | 28 |
| 10 | GTQSPFFLLL | GGC/ACC/CAG/TCT/CCT/TTC/TTC/CTG/CTG/CTG | 29 |
| 11 | LAFREGTINV | CTG/GCC/TTC/AGA/GAA/GGT/ACC/ATC/AAC/GTC | 30 |
| 12 | TLASHSTKTD | ACT/CTG/GCC/TCG/CAC/TCG/ACC/AAG/ACC/GAT | 31 |
| 13 | LQRDISEMFL | CTG/CAA/AGA/GAT/ATC/TCG/GAA/ATG/TTC/CTG | 32 |
| 14 | AIWGQDVTSV | GCC/ACT/TGG/GGA/CAG/GAT/GTC/ACC/TCG/GTC | 33 |
| 15 | ALWGQDVTSL | GCC/CTG/TGG/GGA/CAG/GAT/GTC/ACC/TCG/CTG | 34 |
| 16 | AMWGQDVTSV | GCC/ATG/TGG/GGA/CAG/GAT/GTC/ACC/TCG/GTC | 35 |
| 17 | AMWGQDVTSL | GCC/ATG/TGG/GGA/CAG/GAT/GTC/ACC/TCG/CTG | 36 |
| 18 | AIWGQDVTSL | GCC/ACT/TGG/GGA/CAG/GAT/GTC/ACC/TCG/CTG | 37 |
| 19 | ALWGQDVTSV | | | a viral vector encoding anyone of the polypeptides as identified by SEQ ID NO: 1 through 19, fragments or variants thereof, optionally expressing co-stimulatory molecules. For example, autologous DCs infected with rF-MUC-1/TRICOM were used as APC. rF-MUC-1/TRICOM is a replication-defective avipox vector containing the transgenes for MUC-1 and for a triad of human costimulatory molecules (B7-1, ICAM-1 and LFA-3, designated TRICOM). rF-MUC-1/TRICOM was shown to efficiently infect human DCs and hyperexpress each of the costimulatory molecules, as well as MUC-1, on the DC surface (Table 2).

In another preferred embodiment, the invention provides a method for generating an immune response to a weakly immunogenic antigen comprising administering to an subject an agonist polypeptide, as identified by any one of SEQ ID NO: 1 through 19, variants or fragments thereof, with a high avidity for HLA fused to the weak immunogen.

In a preferred embodiment, the invention provides an isolated nucleic acid molecule which encodes an agonist In another preferred embodiment, the invention provides for a vector comprising an isolated nucleic acid molecule expressing any one of amino acids identified by SEQ ID NO: 1 through 19, fragments or variants, thereof. The vector preferably encodes encoding immune cell co-stimulatory molecules, such as for example, B7-1, ICAM-1 and LFA-331.

In yet another preferred embodiment, the invention provides for the transduction of dendritic cells with a vector comprising any one of the molecules as identified by SEQ ID NO: 1 through 19, fragments or variants thereof, and optionally, immune cell co-stimulatory molecules, such as for example, B7-1, ICAM-1 and LFA-3.35. These recombinant vectors provide specific anti-tumor effect for subjects who have been diagnosed with MUC-1⁺ tumors. However, this antigen is merely an illustrative example and is not meant to be construed as limiting in any way. Examples of other antigens that are useful for treating different types of cancers, include, but not limited to overexpressed or mutated forms of antigens. For example, Her2/neu⁺ tumors such as breast, renal, prostate, and other HER2 tumors, carcinogenic embryonic antigen (CEA) for gastro-intestinal cancers; K-ras for lung, gastrointestinal and bladder cancers; p53 which affects a wide variety of neoplastic growth; SARDT3 in neck and head cancers.

In another preferred embodiment, dendritic cells of an subject, suffering from or susceptible to, cancer, are transduced in vivo with recombinant vectors expressing agonist polypeptide epitopes. Dendritic cells can be isolated from a subject, cultured ex vivo with a vector, and then re-infusing the cultured dendritic cells into the subject. Culturing of dendritic cells is described in detail in the examples which follow. Alternatively, the vector may be administered to a subject in need of such treatment.

In a preferred embodiment, transduced dendritic cells present antigen, for example, agonist peptide fragments of the MUC-1 antigen on their surface. Lymphocytes, specific for the presented antigens, are activated, proliferate and recognize tumor cells expressing the MUC-1 antigen. Lymphocytes include, B cells, T helper cells and cytotoxic T cells. Recognition, of any cell expressing antigenic epitopes by the immune cells, results in the destruction of a tumor cell.

In another preferred embodiment, the invention provides a nucleic acid vector comprising one or more nucleic acid sequences encoding polypeptides as identified by any one of SEQ ID NO: 1 through 19, fragments or variants thereof, operably linked to an inducible promoter.

In another preferred embodiment the nucleic acid vector is a viral vector, plasmid and the like. Preferably the nucleic acid vector comprises an inducible promoter which is tissue specific, and optionally, immune cell co-stimulatory molecules.

In another preferred embodiment, the vector comprising a nucleic acid sequence encoding any one of the polypeptides identified by SEQ ID NO: 1 through 19.

In another preferred embodiment, the vector codes for any one of the polypeptides identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%.

In another preferred embodiment, the invention provides a host cell expressing the polypeptide products of the vector as identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%. Preferably the host cell is an antigen presenting cell, such as for example, a monocyte/macrophage, dendritic cell or the like.

In accordance with the invention, the transduced dendritic cells present antigen to cells of the immune system and activate the immune system to recognize tumor antigen epitopes, such as for example a tumor cell expressing the MUC-1 antigen.

In a preferred embodiment, the vector is a avipox vector comprising nucleic acid molecules encoding agonist polypeptides and co-stimulatory molecules, as described in detail in the examples which follow. Other vectors may also be used. Preferred vectors include viral vectors, fusion proteins and chemical conjugates. Retroviral vectors include moloney murine leukemia viruses. DNA viral vectors are preferred. Viral vectors can be chosen to introduce the genes to cells of choice. Such vectors include pox vectors such as orthopox or avipox vectors, herpesvirus vectors such as herpes simplex I virus (HSV) vector (Geller et al., 1995, *J. Neurochem.*, 64:487; Lim et al., 1995, in *DNA Cloning: Mammalian Systems*, D. Glover, ed., Oxford Univ. Press, Oxford, England; Geller et al., 1990, Proc. Natl. Acad. Sci. U.S.A. 87: 1149), other adenovirus vectors (LeGal LaSalle et al., 1993, *Science* 259: 988; Davidson et al., 1993, *Nat. Genet.* 3: 219; Yang et al., 1995, *J. Virol.* 69: 2004) and adeno-associated virus vectors (Kaplitt et al., 1994, *Nat. Genet.* 8: 148; Kotin, et al. WO 98/11244 (Mar. 19, 1998) and Chiorini, et al WO 99/61601 (Dec. 2, 1999)).

Pox viral vectors introduce the gene into the cells cytoplasm. Avipox virus vectors result in only short term expression of the nucleic acid. Adenovirus vectors, adeno-associated virus vectors and herpes simplex virus vectors are preferred for introducing the nucleic acid into neural cells. The adenovirus vector results in a shorter term expression (about 2 months) than adeno-associated virus (about 4 months), which in turn is shorter than HSV vectors. The vectors can be introduced by standard techniques, e.g. infection, transfection, transduction or transformation. Examples of modes of gene transfer include for example, naked DNA, calcium phosphate precipitation, DEAE dextran, electroporation, protoplast fusion, lipofection, cell microinjection and viral vectors.

The vector can be employed to target essentially any desired target cell. For example, stereotaxic injection can be used to direct the vectors (e.g. adenovirus, HSV) to a desired location. Other methods that can be used include catheters, intravenous, parenteral, intraperitoneal, and subcutaneous injection, and oral or other known routes of administration.

Another preferred method is DNA immunization. DNA immunization employs the subcutaneous injection of a plasmid DNA (pDNA) vector encoding a tumor marker. The pDNA sequence is taken up by antigen presenting cells (APC), preferably by dendritic cells. Once inside the cell, the DNA encoding protein is transcribed and translated and presented to lymphocytes.

Genetic constructs comprise a nucleotide sequence that encodes the nucleic acid sequence of choice and preferably includes an intracellular trafficking sequence operably linked to regulatory elements needed for gene expression.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers may be required for gene expression of the sequence of choice, for example, the agonist polypeptides identified by SEQ ID NO: 1 through 19, variants or fragments thereof. It is necessary that these elements be operably linked to the sequence that encodes the desired proteins and that the regulatory elements are operable in the subject to whom they are administered.

Initiation codons and stop codons are generally considered to be part of a nucleotide sequence that encodes the immunogenic target protein. However, it is necessary that these elements are functional in the subject to whom the gene construct is administered. The initiation and termination codons must be in frame with the coding sequence.

Promoters and polyadenylation signals used must be functional within the cells of the subject.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metallothionein.

Examples of polyadenylation signals useful to practice the present invention, especially in the production of a genetic vaccine for humans, include but are not limited to SV40 polyadenylation signals and LTR polyadenylation signals.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. For example, plasmids pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The method of the present invention comprises the steps of administering nucleic acid molecules to tissue of the subject. In some preferred embodiments, the nucleic acid molecules are administered intramuscularly, intranasally, intraperitoneally, subcutaneously, intradermally, or topically or by lavage to mucosal tissue selected from the group consisting of vaginal, rectal, urethral, buccal and sublingual.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in e.g. International Application No. PCT/US94/00899 filed Jan. 26, 1994 and International Application No. PCT/US95/04071 filed Mar. 30, 1995, both incorporated herein by reference. Facilitating agents which are administered in conjunction with nucleic acid molecules may be administered as a mixture with the nucleic acid molecule or administered separately simultaneously, before or after administration of nucleic acid molecules.

In some preferred embodiments, the genetic constructs of the invention are formulated with or administered in conjunction with a facilitator selected from the group consisting of, for example, benzoic acid esters, anilides, amidines, urethans and the hydrochloride salts thereof such as those of the family of local anesthetics. The facilitating agent is administered prior to, simultaneously with or subsequent to the genetic construct. The facilitating agent and the genetic construct may be formulated in the same composition.

In some embodiments of the invention, the subject is first subject to injection of the facilitator prior to administration of the genetic construct. That is, for example, up to a about a week to ten days prior to administration of the genetic construct, the subject is first injected with the facilitator. In some embodiments, the subject is injected with the facilitator about 1 to 5 days; in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical composition.

In some embodiments, the genetic constructs are administered free of facilitating agents, that is in formulations free from facilitating agents using administration protocols in which the genetic constructions are not administered in conjunction with the administration of facilitating agents.

Nucleic acid molecules which are delivered to cells according to the invention may serve as genetic templates for proteins that function as prophylactic and/or therapeutic immunizing agents. In preferred embodiments, the nucleic acid molecules comprise the necessary regulatory sequences for transcription and translation of the coding region in the cells of the animal.

In further embodiments of the present invention, the agonist polypeptides described herein may be used for the immunotherapy of MUC-1 positive tumors. In these embodiments, the compounds (which may be polypeptides, antibodies or nucleic acid molecules) are preferably incorporated into pharmaceutical compositions or vaccines. Pharmaceutical compositions comprise one or more such compounds and a physiologically acceptable carrier. Vaccines may comprise one or more polypeptides and an immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, including one or more separate polypeptides.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

In another preferred embodiment, the invention provides a method for treating a subject suffering from or susceptible to a MUC-1 tumor comprising administering to a subject any one of the peptides identified by SEQ ID NO: 1 through 19, fragments or variants thereof.

In accordance with the invention, an immune response to a MUC-1 tumor antigen, is generated, by administering an agonist polypeptides in a therapeutically effective dose sufficient to generate a cellular immune response, wherein the agonist polypeptides are any one of polypeptides identified by SEQ ID NO: 1 through 19, fragments or variants thereof, and optionally immune cell co-stimulatory molecules. Preferably, the polypeptides as identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%.

The peptides are administered to an subject suffering from or susceptible to cancers. Definite clinical diagnosis of a particular cancer warrants the administration of the peptides, including the early stages of the disease. Prophylactic applications are warranted in cases where subjects with familial history of disease and predicted to be at risk by reliable prognostic indicators could be treated prophylactically to interdict cancer prior to onset, such as MUC-1 positive cancer; or can be administered post operatively.

Peptide vaccines can be administered in many possible formulations, in pharmacologically acceptable mediums. In the case of a short peptide, the peptide can be conjugated to a carrier, such as KLH, in order to increase its immunogenicity. The vaccine can be administered in conjunction with an adjuvant, various of which are known to those skilled in the art. After initial immunization with the vaccine, a booster can be provided. The vaccines are administered by conventional methods, in dosages which are sufficient to elicit an immunological response, which can be easily determined by those skilled in the art.

Efficacy of the peptide in the context of prevention is judged based on the following criteria: frequency of peptide reactive T cells determined by limiting dilution, proliferation response of peptide reactive T cell lines and clones, cytokine profiles of T cell lines and clones to the desired peptide established from subjects. Efficacy is established by decrease in frequency of reactive cells, a reduction in thymidine incorporation with altered peptide compared to native, and a reduction in TNF and IFN-α. Clinical measurements include the relapse rate in one and two year intervals, on a Kaplan-Meier curve, a delay in sustained cancer stage progression reduction in the number and size of tumors including a change in area and volume of T2 images on MRI, and the number and volume of lesions determined by gadolinium enhanced images.

Peptides, variants and fragments thereof, of the present invention may be administered either alone, or as a pharmaceutical composition. Briefly, pharmaceutical compositions of the present invention may comprise one or more of the peptides, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, cytokines like β-interferon.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

Pharmaceutical compositions of the present invention may be administered in a manner appropriate to the disease to be treated (or prevented). The quantity and frequency of administration will be determined by such factors as the condition of the subject, and the type and severity of the subject's disease. Within particularly preferred embodiments of the invention, the peptides, variants, or fragments thereof, or pharmaceutical compositions described herein may be administered at a dosage ranging from about 5 to 50 mg/kg, although appropriate dosages may be determined by clinical trials. Dosages of peptide analogue will be approximately 5-50 mg/kg, but are determined more accurately following trials. Subjects may be monitored for therapeutic effectiveness by MRI, and signs of clinical exacerbation, as described above.

MRI can be used to measure active lesions using gadolinium-DTPA-enhanced imaging (McDonald et al. *Ann. Neurol.* 36:14, 1994) or the location and extent of lesions using $T_2$-weighted techniques. Briefly, baseline MRIs are obtained. The same imaging plane and subject position are used for each subsequent study. Positioning and imaging sequences are chosen to maximize lesion detection and facilitate lesion tracing. The same positioning and imaging sequences are used on subsequent studies. The presence, location and extent of MS lesions are determined by radiologists. Areas of lesions are outlined and summed slice by slice for total lesion area. Three analyses may be done: evidence of new lesions, rate of appearance of active lesions, percentage change in lesion area (Paty et al., *Neurology* 43:665, 1993). Improvement due to therapy is established when there is a statistically significant improvement in an subject compared to baseline or in a treated group versus a placebo group.

In another aspect of the invention, any tumor antigen polypeptide can be administered to an subject diagnosed as suffering from or susceptible to cancers. The polypeptides corresponding to identified tumor antigens can be used to stimulate the cells of the immune system to recognize and lyse tumor cells expressing tumor antigens, such as for example, CEA, p53, K-ras, and the like.

While various procedures involving the use of antibodies have been applied in the treatment of tumors, few if any successful attempts using activated cytotoxic T-cells have been recorded. Theoretically, cytotoxic T-cells would be the preferable means of treating tumors. However, no procedures have been available to specifically activate cytotoxic T-cells. In contrast to antibodies, the T-cell receptors on the surface of CD8 cells cannot recognize foreign antigens directly. Antigen must first be presented to the T cell receptor, such as a dendritic cell.

The presentation of antigen to CD8 T-cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leukocyte antigen) complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T-cells.

MHC products are grouped into three major classes, referred to as I, II, and III. T-cells that serve mainly as helper cells express CD4 and primarily interact with Class II molecules, whereas CD8-expressing cells, which mostly represent cytotoxic effector cells, interact with Class I molecules.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T-cells. In contrast, complexes of MHC molecules with peptides derived from normal cellular products play a role in "teaching" the T-cells to tolerate self-peptides, in the thymus. Class I molecules do not present entire, intact antigens; rather, they present peptide fragments thereof, "loaded" onto their "peptide binding groove".

As will be recognized by those in the art, the term "host compatible" or "autologous" cells means cells that are of the same or similar haplotype as that of the subject or "host" to which the cells are administered.

The presentation of Class I MHC molecules bound to peptide alone has generally been ineffective in activating CD8 cells. In nature, the CD8 cells are activated by antigen-presenting cells, such as, for example, dendritic cells, which present not only a peptide-bound Class I MHC molecule, but also a costimulatory molecule. Such costimulatory molecules include B7 which is now recognized to be two subgroups designated as B7.1 and B7.2, ICAM-1 and LFA-3. It has also been found that cell adhesion molecules such as integrins assist in this process.

Dendritic cells are antigen-presenting cells that are found in all tissues and organs, including the blood. Specifically, dendritic cells present antigens for T lymphocytes, i.e., they process and present antigens, and stimulate responses from naive and memory T cells. In addition to their role in antigen presentation, dendritic cells directly communicate with non-lymph tissue and survey non-lymph for an injury signal (e.g., ischemia, infection, or inflammation) or tumor growth. Once signaled, dendritic cells initiate the immune response by releasing IL-1 which triggers lymphocytes and monocytes. When the CD8 T-cell interacts with an antigen-presenting cell, such as a dendritic cell, having the peptide bound by a Class I MHC and costimulatory molecule, the CD8 T-cell is activated to proliferate and becomes an effector T-cell. See, generally, Janeway and Travers, Immunobiology, published by Current Biology Limited, London (1994), incorporated by reference.

Accordingly, what is needed and which the present invention provides, is a means to activate T-cells so that they proliferate, become cytotoxic for cells expressing the desired antigen, such as for example, MUC-1, and maintain memory cells specific for the administered antigen. Thus, the immune system is primed against various tumor epitopes so if spontaneous tumors arise, a pool of primed immune cells exist which become activated to recognize and kill the tumor cells.

Preferably, the epitopes presented to the immune system comprise agonist epitopes as described herein. Agonist polypeptides preferably comprise an amino acid sequence which is at least about 60% identical to the amino acid sequence of SEQ ID NO: 1 through 19, fragments or variants thereof, more preferably, the agonist polypeptide comprises an amino acid sequence which is at least about 80% identical to the amino acid sequence of SEQ ID NO: 1 through 19. more preferably, the agonist polypeptide comprises an amino acid sequence which is at least about 90%, 95%, or 99.9% identical to the amino acid sequence of SEQ ID NO: 1 through 19.

A review of the biology of memory T cells may be found in Dutton et al. (1998) *Ann. Rev Immunol* 16:201-23. Memory cells express a different pattern of cell surface markers, and they respond in several ways that are functionally different from those of naive cells. Human memory cells are $CD45RA^-$, $CD45RO^+$. In contrast to naïve cells, memory cells secrete a full range of T cell cytokines.

Chemokines and cytokines also play a powerful role in the development of an immune response. The role of chemokines in leukocyte trafficking is reviewed by Baggiolini (1998) *Nature* 392:565-8, in which it is suggested that migration responses in the complicated trafficking of lymphocytes of different types and degrees of activation will be mediated by chemokines. The use of small molecules to block chemokines is reviewed by Baggiolini and Moser (1997) *J. Exp. Med.* 186:1189-1191.

The role of various specific chemokines in lymphocyte homing has been previously described. For example, Campbell et al. (1998) Science, showed that SDF-1 (also called PBSF), 6-C-kine (also called Exodus-2), and MIP-3beta (also called ELC or Exodus-3) induced adhesion of most circulating lymphocytes, including most $CD4^+$ T cells; and MIP-3alpha (also called LARC or Exodus-1) triggered adhesion of memory, but not naïve, $CD4^+$ T cells. Tangemann et al. (1998) *J. Immunol.* 161:6330-7 disclose the role of secondary lymphoid-tissue chemokine (SLC), a high endothelial venule (HEV)-associated chemokine, with the homing of lymphocytes to secondary lymphoid organs. Campbell et al. (1998) *J. Cell Biol* 141(4):1053-9 describe the receptor for SLC as CCR7, and that its ligand, SLC, can trigger rapid integrin-dependent arrest of lymphocytes rolling under physiological shear.

Mature B cells can be measured in immunoassays, for example, by cell surface antigens including CD19 and CD20 with monoclonal antibodies labeled with fluorochromes or enzymes may be used to these antigens. B cells that have differentiated into plasma cells can be enumerated by staining for intracellular immunoglobulins by direct immunofluorescence in fixed smears of cultured cells.

Several different ways, to assess maturity and cell differentiation, are available. For example, one such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation or measure specific antibody production directed at a subject's tumor, tumor cell lines or cells from fresh tumors.

Immune cells express a variety of cell surface molecules which can be detected with either monoclonal antibodies or polyclonal antisera. Immune cells that have undergone differentiation or activation can also be enumerated by staining for the presence of characteristic cell surface proteins by direct immunofluorescence in fixed smears of cultured cells.

In vitro T cell cytotoxic assays are well known to those skilled in the art. A preferred method is to measure cytotoxicity in a 5 hr $^{51}$Sodium chromate ($^{51}$Cr) release assay. In particular, a 20 hr $^{51}$Cr-release assay is preferred. Tumor cells, also referred to herein as "target cells" are plated in flat-bottomed microtiter plates and incubated at 37° C. overnight. The targets are washed and labeled the next day with $^{51}$Cr at 37° C. $^{51}$Cr is taken up by the target cells, either by endocytosis or pinocytosis, and is retained in the cytoplasm. The wells containing tumor cells are washed, and then armed or unarmed ATC, referred to as "effector cells" are plated at different E:T ratios and incubated overnight at 37° C. Cytolysis is a measure of the $^{51}$Cr released from the target cells into the supernatant due to destruction of the target cells by the effector cells. The microtiter plates are centrifuged at 1000 rpm for 10 minutes and an aliquot of about 50 µl to about 100 µl is removed and the level of radioactivity is measured the next day by a gamma counter and the percent specific lysis calculated.

Percent specific lysis is measured by using the formula:

$$\frac{(^{51}\text{Cr released from the target cells}) - (\text{spontaneous } ^{51}\text{Cr released from the target cells})}{(\text{maximum } ^{51}\text{Cr released from the target cells}) - (\text{spontaneous } ^{51}\text{Cr released from the target cells})} \times 100$$

The spontaneous $^{51}$Cr released from the target cells is measured with tumor cells to which no effector cells have been added. Maximum $^{51}$Cr released from the target cells is obtained by adding, for example, 1M HCl and represents the total amount of $^{51}$Cr present in the cytoplasm of the target cell.

Other means of assaying for T lymphocyte activity is by the mixed lymphocyte reaction described in the examples which follow. Other cytotoxicity assays such as the labeling of target cells with tritiated thymidine ($^3$H-TdR) may also be used. $^3$H-TdR is taken up by target cells into the nucleus of the cell. Release of $^3$H-TdR is a measure of cell death by DNA fragmentation. The assay is conducted as above except the incubation period is at least about 48 hours and 50 µl to about 100 µl of the supernatant is measured by a beta-counter in the presence of at least about 1 ml of scintillation fluid. Calculation of percent specific lysis is performed using the above formula.

In a preferred embodiment the polypeptide is expressed at least at a higher level in a subject with cancer as compared to expression levels in normal subjects, preferably the polypeptide is expressed at least about 5 to about 10 fold higher in a subject with cancer as compared to expression in a normal subject. Preferably the cancer is a MUC-1$^+$ cancer and the subject sample is obtained from a mammalian subject, including a primate such as a human subject.

In another preferred embodiment, the invention provides for a method for treating a subject suffering from or susceptible to a MUC-1 tumor comprising isolating dendritic cells from a subject suffering from cancer; and, treating the dendritic cells with one or more of the polypeptides identified by SEQ ID NO: 1 through 19; fragments and variants thereof. Preferably, the treated dendritic cells are administered to the subject.

In yet another preferred embodiment, autologous dendritic cells can be isolated from a subject, transduced with the vectors described in detail herein, cultured, and re-infused into the subject.

An "isolated" or "purified" population of cells is substantially free of cells and materials with which it is associated in nature. By substantially free or substantially purified APCs is meant at least 50% of the population are APCs, preferably at least 70%, more preferably at least 80%, and even more preferably at least 90% free of non-APCs cells with which they are associated in nature.

Dendritic cells of different maturation stages can be isolated based on the cell surface expression markers. For example, mature dendritic cells are less able to capture new proteins for presentation but are much better at stimulating resting T cells to grow and differentiate. Thus, mature dendritic cells can be of importance. Mature dendritic cells can be identified by their change in morphology; by their nonadherence; and by the presence of various markers. Such markers include, but are not limited to, cell surface markers such as B7.2, CD40, CD11c$^+$, and MHC class II. Alternatively, maturation can be identified by observing or measuring the production of pro-inflammatory cytokines Dendritic cells can be collected and analyzed using typical cytofluorography and cell sorting techniques and devices, such as a fluorescence-activated cell sorter (FACS). Antibodies specific to cell surface antigens of different stages of dendritic cell maturation are commercially available.

The amount of dendritic cells administered to the subject will also vary depending on the condition of the subject and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ dendritic cells are utilized for adult humans. These amounts will vary depending on the age, weight, size, condition, sex of the subject, the type of tumor to be treated, the route of administration, whether the treatment is regional or systemic, and other factors. Those skilled in the art should be readily able to derive appropriate dosages and schedules of administration to suit the specific circumstance and needs of the subject.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8 cells via intravenous infusion is appropriate. Any toxicity, from donor cell infusion, observed in a pregnant female will result in immediate cessation of any further infusions. Toxicity is measured according to the National Cancer Institute (NCI) scale.

Toxicity Grading—the NCI Common Toxicity Scale.

If Grade I-II toxicities occur, the subject may continue with the infusion schedule.

If Grade III toxicity occurs, the "drug" will be held until the toxicity decreases to Grade I or II, then the infusion will be restarted. If Grade III or IV toxicity occurs after the restart, the "drug" infusions will be stopped.

If Grade IV toxicity occurs, the subject is scored as having Grade IV toxicity and the next infusion is reduced to the previous dose. If the previous dose causes Grade IV toxicity, then the "drug" will be stopped.

If Grade IV toxicity occurs in 1 of 3 subjects at a specific dose level, an additional 3 subjects must be entered at that cell-dose level for a total of 6 subjects at that dose level. If 2 of 6 subjects at a cell-dose level develop Grade IV toxicity, this dose is defined as the maximum tolerated dose (MTD). The next 3 subjects will be given 66% (two-thirds) of the previous cell-dose level. For the purposes of evaluation for dose-escalation, each subject at the same dose level should received at least 4 of 6 infusions.

Large quantities of antigen-presenting dendritic cells can be generated ex vivo as described in U.S. Pat. No. 6,497,876, which is incorporated herein, in its entirety. Following collection of an subject's CD34$^+$ hematopoietic progenitors and stem cells, cytokines such as granulocyte-macrophage colony stimulating factor (GM-CSF) and flt-3 ligand (flt3-L) can be used to expand the cells in vitro and to drive them to differentiate into cells of the dendritic cell lineage. Cytokines can also be used to increase the numbers of CD34$^+$ cells in circulation prior to collection. The resulting dendritic cells are exposed to an antigen one wishes to elicit an immune response against, and allowed to process the antigen (this procedure is sometimes referred to in the art as "antigen-pulsing"). The antigen-pulsed (or antigen-expressing) dendritic cells are then activated with a CD40 binding protein, and subsequently administered to the subject.

Dendritic cells comprise a heterogeneous cell population with distinctive morphology and a widespread tissue distribution. The dendritic cell system and its role in immunity is reviewed by Steinman, R. M., *Annu. Rev. Immunol.,* 9:271-296 (1991), incorporated herein by reference. The cell surface of dendritic cells is unusual, with characteristic veil-like projections, and is characterized by having the cell surface markers CD1a$^+$, CD4$^+$, CD86$^+$, or HLA-DR$^+$. Dendritic cells have a high capacity for sensitizing MHC-restricted T cells and are very effective at presenting antigens to T cells in situ, both self-antigens during T cell development and tolerance and foreign antigens during immunity.

Because of their effectiveness at antigen presentation, autologous dendritic cells preferably are used ex vivo as alloantigen adjuvants (see, for example, Romani, et al., *J. Exp. Med.,* 180:83 (1994). The use of dendritic cells as immunostimulatory agents has been limited due to the low frequency of dendritic cells in peripheral blood, the limited accessibility of lymphoid organs and the dendritic cells' terminal state of differentiation. Dendritic cells originate from CD34 bone marrow or peripheral blood progenitors and peripheral blood mononuclear cells, and the proliferation and maturation of dendritic cells can be enhanced by the cytokines GM-CSF sargramostim, Leukine™ (Immunex Corporation, Seattle, Wash.), TNF-α, c-kit ligand (also known as stem cell factor (SCF), steel factor (SF), or mast cell growth factor (MGF)) and interleukin-4 Recently, flt3-L has been found to stimulate the generation of large numbers of functionally mature dendritic cells, both in vivo and in vitro.

Ex Vivo Culture of Dendritic Cells

A procedure for ex vivo expansion of hematopoietic stem and progenitor cells is described in U.S. Pat. No. 5,199,942, incorporated herein by reference. Other suitable methods are known in the art. Briefly, ex vivo culture and expansion comprises: (1) collecting CD34$^+$ hematopoietic stem and progenitor cells from a subject from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used.

Stem or progenitor cells having the CD34 marker constitute only about 1% to 3% of the mononuclear cells in the bone marrow. The amount of CD34$^+$ stem or progenitor cells in the peripheral blood is approximately 10- to 100-fold less than in bone marrow. Cytokines such as flt3-L may be used to increase or mobilize the numbers of dendritic cells in vivo. Increasing the quantity of a subject's dendritic cells may facilitate antigen presentation to T cells for antigen(s) that already exists within the subject, such as a tumor antigen, or a bacterial or viral antigen. Alternatively, cytokines may be administered prior to, concurrently with or subsequent to administration of an antigen to a subject for immunization purposes.

Peripheral blood cells are collected using apheresis procedures known in the art. See, for example, Bishop et al., *Blood,* vol. 83, No. 2, pp. 610-616 (1994). Briefly, peripheral blood progenitor cells (PBPC) and peripheral blood stem cells (PBSC) are collected using conventional devices, for example, a Haemonetics Model V50 apheresis device (Haemonetics, Braintree, Mass.). Four-hour collections are performed typically no more than five times weekly until approximately $6.5 \times 10^8$ mononuclear cells (MNC)/kg are collected. The cells are suspended in standard media and then centrifuged to remove red blood cells and neutrophils. Cells located at the interface between the two phases (the buffy coat) are withdrawn and resuspended in HBSS. The suspended cells are predominantly mononuclear and a substantial portion of the cell mixture are early stem cells.

A variety of cell selection techniques are known for identifying and separating CD34$^+$ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (i.e., flt-3, CD34, My-10, and Thy-1) are known in the art, as are specific binding proteins.

In one method, antibodies or binding proteins are fixed to a surface, for example, glass beads or flask, magnetic beads, or a suitable chromatography resin, and contacted with the population of cells. The stem cells are then bound to the bead matrix. Alternatively, the binding proteins can be incubated with the cell mixture and the resulting combination contacted with a surface having an affinity for the antibody-cell complex. Undesired cells and cell matter are removed providing a relatively pure population of stem cells. The specific cell binding proteins can also be labeled with a fluorescent label, e.g., chromophore or fluorophore, and the labeled cells separated by sorting. Preferably, isolation is accomplished by an immunoaffinity column.

Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. The substrate should, either by its own properties, or by the addition of a chemical moiety, display high-affinity for a moiety found on the cell-binding protein. Typical substrates include avidin and streptavidin, while other conventional substrates can be used.

In one useful method, monoclonal antibodies that recognize a cell surface antigen on the cells to be separated are typically further modified to present a biotin moiety. The affinity of biotin for avidin thereby removably secures the monoclonal antibody to the surface of a packed bed (see Berenson, et al., *J. Immunol. Meth.,* 91:11, 1986). The packed bed is washed to remove unbound material, and target cells are released using conventional methods. Immunoaffinity columns of the type described above that utilize biotinylated anti-CD34 monoclonal antibodies secured to an avidin-coated packed bed are described for example, in WO 93/08268.

An alternative means of selecting the quiescent stem cells is to induce cell death in the dividing, more lineage-committed, cell types using an antimetabolite such as 5-fluorouracil (5-FU) or an alkylating, agent such as 4-hydroxycyclophosphamide (4-HC). The non-quiescent cells are stimulated to proliferate and differentiate by the addition of growth factors that have little or no effect on the stem cells, causing the non-stem cells to proliferate and differentiate and making them more vulnerable to the cytotoxic effects of 5-FU or 4-HC. See Berardi et al., *Science,* 267:104 (1995), which is incorporated herein by reference.

Isolated stem cells can be frozen in a controlled rate freezer (e.g., Cryo-Med, Mt. Clemens, Mich.), then stored in the vapor phase of liquid nitrogen using dimethylsulfoxide as a cryoprotectant. A variety of growth and culture media can be used for the growth and culture of dendritic cells (fresh or frozen), including serum-depleted or serum-based media. Useful growth media include RPMI, TC 199, Iscoves modified Dulbecco's medium (Iscove, et al., F. *J. Exp. Med.,* 147: 923 (1978)), DMEM, Fischer's, alpha medium, NCTC, F-10, Leibovitz's L-15, MEM and McCoy's. Particular nutrients present in the media include serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES, or Tris, that acts to stabilize the pH of the media, and various inorganic salts. A variety of serum-free cellular growth media is described in WO 95/00632, which is incorporated herein by reference. The collected $CD34^+$ cells are cultured with suitable cytokines, for example, as described herein. $CD34^+$ cells then are allowed to differentiate and commit to cells of the dendritic lineage. These cells are then further purified by flow cytometry or similar means, using markers characteristic of dendritic cells, such as CD1a, HLA DR, CD80 and/or CD86. The cultured dendritic cells are exposed to an antigen, for example, an allogeneic class I HLA molecule, allowed to process the antigen, and then cultured with an amount of a CD40 binding protein to activate the dendritic cell. Alternatively, the dendritic cells are transfected with a gene encoding an allogeneic HLA class I molecule or immune related receptors, and then cultured with an amount of a CD40 binding protein to activate the antigen-presenting dendritic cells.

The activated, antigen-carrying dendritic cells are them administered to an subject in order to stimulate an antigen-specific immune response. The dendritic cells can be administered prior to, concurrently with, or subsequent to, antigen administration. Alternatively, T cells may be collected from the subject and exposed to the activated, antigen-carrying dendritic cells in vitro to stimulate antigen-specific T cells, which are administered to the subject.

Useful Cytokines

Various cytokines will be useful in the ex vivo culture of dendritic cells. Flt3-L refers to a genus of polypeptides that are described in EP 0627487 A2 and in WO 94/28391, both incorporated herein by reference. A human flt3-L cDNA was deposited with the American Type Culture Collection, Rockville, Md., USA (ATCC) on Aug. 6, 1993 and assigned accession number ATCC 69382. IL-3 refers to a genus of interleukin-3 polypeptides as described in U.S. Pat. No. 5,108,910, incorporated herein by reference. A DNA sequence encoding human IL-3 protein suitable for use in the invention is publicly available from the American Type Culture Collection (ATCC) under accession number ATCC 67747. c-kit ligand is also referred to as Mast Cell Growth Factor (MGF), Steel Factor or Stem Cell Factor (SCF), and is described in EP 423,980, which is incorporated herein by reference. Other useful cytokines include Interleukin-4 (IL-4; Mosley et al., *Cell* 59:335 (1989), Idzerda et al., *J. Exp. Med.* 171:861 (1990) and Galizzi et al., *Intl. Immunol.* 2:669 (1990), each of which is incorporated herein by reference) and granulocyte-macrophage colony stimulating factor (GM-CSF; described in U.S. Pat. Nos. 5,108,910, and 5,229,496 each of which is incorporated herein by reference). Commercially available GM-CSF (sargramostim, Leukine™) is obtainable from Immunex Corp., Seattle, Wash.). Moreover, GM-CSF/IL-3 fusion proteins (i.e., a C-terminal to N-terminal fusion of GM-CSF and IL-3) will also be useful in ex vivo culture of dendritic cells. Such fusion proteins are known and are described in U.S. Pat. Nos. 5,199,942, 5,108,910 and 5,073, 627, each of which is incorporated herein by reference. A preferred fusion protein is PIXY321 as described in U.S. Pat. No. 5,199,942.

Useful cytokines act by binding a receptor present on the surface of a dendritic cell and transducing a signal. Moreover, additional binding proteins can be prepared as described herein for CD40 binding proteins, that bind appropriate cytokine receptors and transduce a signal to a dendritic cell. For example, WO 95/27062 describes agonistic antibodies to Flt-3, the receptor for Flt-3L, from which various Flt-3 binding. proteins can be prepared. Additional useful cytokines include biologically active analogs of cytokines that are useful for culturing dendritic cells. Useful cytokine analogs have an amino acid sequence that is substantially similar to the native cytokine, and are biologically active capable of binding to their specific receptor and transducing a biological signal. Such analogs can be prepared and tested by methods that are known in the art.

An alternate method for preparing dendritic cells that present antigen is to transfect the dendritic cells with a gene encoding an antigen or a specific polypeptide derived therefrom. Once the dendritic cells express the antigen in the context of MHC, the dendritic cells are activated with a CD40 binding protein, and subsequently administered to the subject to provide a stronger and improved immune response to the antigen.

The activated antigen-presenting dendritic cells can also be used as a vaccine adjuvant and can be administered prior to, concurrently with or subsequent to antigen administration. Moreover, the dendritic cells can be administered to the subject prior to, concurrently with or subsequent to administration of cytokines that modulate an immune response, for example a CD40 binding protein (i.e., soluble CD40L), or a soluble CD83 molecule. Additional useful cytokines include, but are not limited to, Interleukins (IL) 1, 2, 4, 5, 6, 7, 10, 12 and 15, colony stimulating factors (CSF) such as GM-CSF, granulocyte colony stimulating factor (G-CSF), or GM-CSF/IL-3 fusion proteins, or other cytokines such as TNF-α or c-kit ligand. Moreover, biologically active derivatives of these cytokines; and combinations thereof will also be useful.

CD40 is a member of the tumor necrosis factor (TNF)/nerve growth factor (NGF) receptor family, which is defined by the presence of cysteine-rich motifs in the extracellular region (Smith et al., *Science* 248:1019, 1990; Mallett and Barclay, *Immunology Today* 12:220; 1991). This family includes the lymphocyte antigen CD27, CD30 (an antigen found on Hodgkin's lymphoma and Reed-Stemberg cells), two receptors for TNF, a murine protein referred to as 4-1BB, rat OX40 antigen, NGF receptor, and Fas antigen. Human CD40 antigen (CD40) is a peptide of 277 amino acids having a molecular weight of 30,600 (Stamenkovic et al., *EMBO J.* 8:1403, 1989). CD40L is believed to be important in feedback regulation of an immune response. For example, a CD40+ antigen presenting cell will present antigen to a T cell, which will then become activated and express CD40L. The CD40L will, in turn, further activate the antigen presenting cell, increasing its efficiency at antigen presentation, and upregulating expression of Class I and Class II MHC, CD80 and CD86 costimulatory molecules, as well as various cytokines (Caux et al., *J. Exp. Med.* 180:1263, 1994).

Purified dendritic cells are then pulsed with (exposed to) antigen, to allow them to take up the antigen in a manner suitable for presentation to other cells of the immune systems. Antigens are classically processed and presented through two pathways. Peptides derived from proteins in the cytosolic compartment are presented in the context of Class I MHC molecules, whereas peptides derived from proteins that are found in the endocytic pathway are presented in the context of Class II MHC. However, those of skill in the art recognize that there are exceptions; for example, the response of CD8+ tumor specific T cells, which recognize exogenous tumor antigens expressed on MHC Class I. A review of MHC-dependent antigen processing and peptide presentation is found in Germain, R. N., *Cell* 76:287 (1994).

Numerous methods of pulsing dendritic cells with antigen are known; those of skill in the art regard development of suitable methods for a selected antigen as routine experimentation. In general, the antigen is added to cultured dendritic cells under conditions promoting viability of the cells, and the cells are then allowed sufficient time to take up and process the antigen, and express antigen peptides on the cell surface in association with either Class I or Class II MHC, a period of about 24 hours (from about 18 to about 30 hours, preferably 24 hours). Dendritic cells may also be exposed to antigen by transfecting them with DNA encoding the antigen. The DNA is expressed, and the antigen is presumably processed via the cytosolic/Class I pathway.

The present invention provides methods of using therapeutic compositions comprising activated, antigen-pulsed dendritic cells. The use of such cells in conjunction with soluble cytokine receptors or cytokines, or other immunoregulatory molecules is also contemplated. The inventive compositions are administered to stimulate an allogeneic immune response, and can be given by bolus injection, continuous infusion, sustained release from implants, or other suitable technique. Typically, the cells on the will be administered in the form of a composition comprising the antigen-pulsed, activated dendritic cells in conjunction with physiologically acceptable carriers, excipients or diluents. Such carriers will be nontoxic to recipients at the dosages and concentrations employed. Neutral buffered saline or saline mixed with serum albumin are exemplary appropriate diluents.

For use in stimulating a certain type of immune response, administration of other cytokines along with activated, antigen-pulsed dendritic cells is also contemplated. Several useful cytokines (or peptide regulatory factors) are discussed in Schrader, J. W. (*Mol Immunol* 28:295; 1991). Such factors include (alone or in combination) Interleukins 1, 2, 4, 5, 6, 7, 10, 12 and 15; granulocyte-macrophage colony stimulating factor, granulocyte colony stimulating factor; a fusion protein comprising Interleukin-3 and granulocyte-macrophage colony stimulating factor; Interferon-γ, TNF, TGF-β, flt-3 ligand and biologically active derivatives thereof. A particularly preferred cytokine is CD40 ligand (CD40L). Other cytokines will also be useful, as described herein. DNA encoding such cytokines will also be useful in the inventive methods, for example, by transfecting the dendritic cells to express the cytokines Administration of these immunomodulatory molecules includes simultaneous, separate or sequential administration with the cells of the present invention.

In another preferred embodiment, the invention provides for a polypeptide identified by any one of SEQ ID NO: 1 through 19 having a sequence identity to anyone one of SEQ ID NO: 1 through 19 of at least about 10%, more preferably, 25%, even more preferably about 40%, 50%, 60%, 70%, 80%, 90%, or 99.9%. Dendritic cells can be pulsed with any of these polypeptides during ex-vivo culture.

In one aspect of the invention, the polypeptide comprises SEQ ID NO: 19. Preferably, the polypeptide binds to HLA molecules with a high avidity and has a higher association constant ($K_a$) for the HLA than a native polypeptide and/or a lower dissociation constant ($K_d$) for the HLA than a native polypeptide.

In another aspect of the invention, the polypeptide is derived from a mucin tumor antigen, preferably, the polypeptide is derived from a non-variable number of tandem repeats region of MUC-1.

In another aspect of the invention, antigen presentation, by antigen presenting cells of the polypeptides induces an immune response, preferably a cellular immune response. For example, the cellular immune response is a cytotoxic T cell response, a T helper cell response, or a B cell immune response.

In yet another aspect, variants of the nucleic acid molecule encoding polypeptides as identified by SEQ ID NO: 1 through 19 can be used to transduce immune cells for the detection and lysing of, for example, MUC-1 positive cancers. An "allele" or "variant" is an alternative form of a gene. Of particular utility in the invention are variants of the genes encoding any potential MUC-1+ tumor cell markers identified by the methods of this invention. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The compositions and methods of the present invention also encompass variants of the above polypeptides and nucleic acid sequences encoding such polypeptides. A polypeptide "variant," as used herein, is a polypeptide that differs from the native polypeptide in substitutions and/or modifications, such that the antigenic and/or immunogenic properties of the polypeptide are retained. Such variants may generally be identified by modifying one of the above polypeptide sequences and evaluating the reactivity of the modified polypeptide with antisera and/or T-cells as described above. Nucleic acid variants may contain one or more substitutions, deletions, insertions and/or modifications such that the antigenic and/or immunogenic properties of the encoded polypeptide are retained. One preferred variant of the polypeptides described herein is a variant that contains nucleotide substitutions, deletions, insertions and/or modifications at no more than 20% of the nucleotide positions.

Preferably, but not limited to, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) vat, ile, leu, met, ala, phe; (4) lys, arg, his; and (5) phe, tyr, trp, his. However, any type of substitution is within the scope and embodiments of the invention.

Variants may also (or alternatively) be modified by, for example, the deletion or addition of amino acids that have minimal influence on the immunogenic or antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, nucleotide sequences encoding all or a portion of the polypeptides described herein may be prepared using any of several techniques. For example, cDNA molecules encoding such polypeptides may be cloned on the basis of the MUC-1 tumor-specific expression of the corresponding mRNAs, using differential display PCR. This technique compares the amplified products from RNA template prepared from normal and MUC-1 positive tumor tissue. cDNA may be prepared by reverse transcription of RNA using a random primer, such as for example, $(dT)_{12}$ AG primer. Following amplification of the cDNA using a random primer, a band corresponding to an amplified product specific to the tumor RNA may be cut out from a silver stained gel and subcloned into a suitable vector, such as the adenovirus vector described in the examples which follow. Nucleotide sequences encoding all or a portion of the MUC-1 tumor-specific polypeptides disclosed by any one of SEQ ID NOs:1 through 6 and variants thereof may be amplified from cDNA prepared as described above using any random primers.

Alternatively, a gene encoding a polypeptide as described herein (or a portion thereof) may be amplified from human genomic DNA, or from tumor cell cDNA, via polymerase chain reaction.

In an embodiment of the invention the presence of the one or more nucleic acid molecules is correlated to a sample of a normal subject. The sample is preferably obtained from a mammal suspected of having a proliferative cell growth disorder, in particular, a MUC-1$^+$ cancer.

Percent identity and similarity between two sequences (nucleic acid or polypeptide) can be determined using a mathematical algorithm (see, e.g., *Computational Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In another preferred embodiment, MUC-1 peptide fragments and derivatives of the invention are of a sufficient length such that they activate the immune system resulting in the lysing of cancer cells, such as, for example cells expressing MUC-1. MUC-1 nucleic acid molecules, fragments and derivatives encoding for any one of the polypeptides identified by SEQ ID NO: 1 through 19, thus preferably comprise at least about 90% nucleotides as compared to the sequence identified by any one of SEQ ID NO: 1 through 19, usually at least about 80% nucleotides as compared to the sequence identified by any one of SEQ ID NO: 1 through 19, more usually at least about 70% nucleotides as compared to the sequence identified by anyone of SEQ ID NO: 1 through 19, even more typically at least about 40% or 50% nucleotides.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The nucleotides at corresponding nucleotide positions are then compared. When a position in the first sequence is occupied by the nucleotide as the corresponding position in the second sequence, then the molecules are identical at that position (as used herein nucleic acid "identity" is equivalent to nucleic acid "sequence identity"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two nucleotide sequences is determined using the GAP program in the GCG software package (available at online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (Comput. Appl. Biosci. 4:11-17 (1988)) which has been incorporated into the ALIGN program (version 2.0 or version 2.0U), using a PAM120 weight residue table, a gap length penalty of 12 and a gap penalty of 4.

The treatment of neoplastic disease or neoplastic cells, refers to an amount of the vectors and/or peptides, described throughout the specification and in the Examples which follow, capable of invoking one or more of the following effects (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

Thus in one aspect of the invention any variant, fragment, mutant can be used to transduce immune cells, such as for example dendritic cells, for the treatment of an subject suffering from, or, prophylactically to an subject susceptible to cancer. As discussed above, a preferred use of nucleic acid sequences identified in the present invention, is for the generation of treatments that lyse for example, MUC-1 cancer cells. The nucleic acid molecules can be expressed by a vector containing a DNA segment encoding the wild-type, alleles, variants, mutations or fragments of the genes. Mutations and alleles of the nucleic acid molecules are also preferably used in the construction of a vector for use in treatment. The vector comprising the desired nucleic acid sequence for conferring resistance to, for example, MUC-1 positive cancer, preferably has at least one such nucleic acid sequence. Alternatively, the vector may be comprised of more than one such nucleic acid sequence, or combinations of allelic variants. The vector can also be comprised of cassettes of different allelic variants or wild type nucleic acid molecules.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual, Second Edition* (1989) Cold Spring Harbor Laboratory Press, Cold Spring Harbor, N.Y. (herein "Sambrook et al., 1989"); *DNA Cloning: A Practical Approach, Volumes I and II* (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Introducing the genes, fragments or alleles thereof, into an subject can include use of vectors, liposomes, naked DNA, adjuvant-assisted DNA, gene gun, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc. The vectors can be chromosomal, non-chromosomal or synthetic.

In another preferred embodiment, cells are isolated and purified cell from a sample, subject or donor subject and are used in functional assays to determine any properties of the cells. Depending on the isolated and purified cellular population, appropriate functional assays known in the art can be conducted. For example, if the population of cells are T cells specific for a desired antigen such as a tumor antigen, cytotoxic T cell assays, T cell proliferation assays, cytokine profiles, determination of surface antigens for T cell maturity or memory T cells, etc., can be carried out.

Isolation of cells useful in the present invention are well known in the art. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells or B cells can be enriched or depleted, for example, by positive and/or negative selection using antibodies to T cell or B cell surface markers, for example by incubating cells with a specific primary monoclonal antibody (mAb), followed by isolation of cells that bind the mAb using magnetic beads coated with a secondary antibody that binds the primary mAb. Peripheral blood or bone marrow derived hematopoietic stem cells can be isolated by similar techniques using stem cell-specific mAbs (e.g., anti-CD34 mAbs). Specific cell populations can also be isolated by fluorescence activated cell sorting according to standard methods. Monoclonal antibodies to cell-specific surface markers known in the art and many are commercially available.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells can be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Procedures for screening can include, methods of screening for molecules to generate an immune response to a MUC-1 tumor antigen. The methods may include:

altering a nucleic acid encoding a portion of the non-variable number of tandem repeats of MUC-1;

expressing the altered nucleic acid to produce a molecule;

contacting a dendritic cell with the molecule; and contacting a T-cell with the dendritic cell, wherein a modulation of the IFN-γ production of the T-cell indicates that the molecule may generate an immune response.

Techniques providing accurate separation include but are not limited to, flow cytometry, which can have varying degrees of sophistication, e.g., a plurality of color channels, low angle and obtuse light scattering detecting channels, impedance channels, etc.

The peptide disclosed herein may be encoded by the corresponding sequences listed herein, but may also be encoded by degenerat codons, including:

| Amino acid | Code |
|---|---|
| A | GCT, GCC, GCA, GCG |
| R | CGT, CGC, CGA, CGG, AGA, AGG |
| N | AAT, AAC |
| D | GAT, GAC |
| C | TGT, TGC |
| G | GGT, GGC, GGA, GGG |
| Q | CAA, CAG |
| E | GAA, GAG |
| H | CAT, CAC |
| I | ATC, ATT, ATA |
| L | TTA, TTG, CTT, CTC, CTA, CTG |
| K | AAA, AAG |
| M | ATG |

-continued

| Amino acid | Code |
|---|---|
| F | TTT, TTC |
| P | CCT, CCC, CCA, CCG |
| S | TCT, TCC, TCA, TCG, AGT, AGC |
| T | ACT, ACC, ACA, ACG |
| W | TGG |
| Y | TAT, TAC |
| V | GTT, GTC, GTA, GTG |

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

EXAMPLES

Example 1

Materials and Methods

Cell Cultures.

The human breast adenocarcinoma cell line MCF-7 (HLA-A2 positive and MUC-1 positive), and SK-Mel-24 (HLA-A2 positive, MUC-1 negative) were purchased from American Type Culture Collection (Manassas, Va.). The cultures were free of mycoplasma and were maintained in complete medium [RPMI 1640 (Invitrogen Life Technologies, Carlsbad, Calif.) supplemented with 10% fetal bovine serum, 2 mM glutamine, 100 units/ml penicillin, and 100 μg/ml streptomycin (Invitrogen Life Technologies, Inc.)]. The C1R cell line is a human plasma leukemia cell line that does not express endogenous HLA-A or B antigens. C1R-A2 cells are C1R cells that express a transfected genomic clone of HLA-A2.1. These cells were obtained from Dr. William E. Biddison (National Institute of Neurological Disorders and Stroke, NIH, Bethesda, Md.). The 174CEM-T2 cell line (T2) transport deletion mutant was provided by Dr. Peter Cresswell (Yale University School of Medicine, New Haven, Conn.). C1R-A2 cells and T2 cells were mycoplasma free and were maintained in RPMI 1640 complete medium and in Iscove's modified Dulbecco's complete medium (Invitrogen Life Technologies), respectively.

Peptides.

The amino acid sequence of MUC-1 was scanned for matches to consensus motifs for HLA-A2 binding peptides. The computer algorithm from the BioInformatics and Molecule Analysis Section of NIH (BIMAS) that was developed by Parker K. C. et al., (*J. Immunol.*, 152: 163-175, 1994) was used, which ranks potential MHC binding peptides according to the predictive one-half-time dissociation of peptide/MHC complexes. The HLA-A2 allele was chosen because they are the most commonly expressed class I allele. Ten-mer peptides from the non-variable number of tandem repeat sequence were synthesized if they conformed to the respective consensus motif. A panel of 10-mer MUC-1 peptides (Table 1) and analogues with single amino acid substitution to positions P1 to P10 of P-92 MUC-1 peptide (see FIG. 1) were made by American Peptide Company (Sunnyvale, Calif.) with purity >90%. In addition, a CEA peptide CAP1-6D (28)>96% pure was made by American Peptide Company (Sunnyvale, Calif.).

Flow Cytometric Analysis.

(i) Single-Color Flow Cytometric Analysis.

The method for single-color flow cytometric analysis has been described previously (Gaudagni F. et al. *Cancer Res.*: 50: 6248-6255, 1990). Briefly, cells were washed three times with cold $Ca^{2+}$ and $Mg^{2+}$-free DPBS and then stained for 1 h at 4° C. using 1 μg of the mAb against HLA-A2 (A2, 28, One Lambda, Inc., Canoga Park, Calif.), CD3, CD4, CD8, and CD56 (BD Biosciences, San Jose, Calif.). Mineral oil plasmacytoma-104E (Cappel/Organon Teknika Corp., West Chester, Pa.) was used as an isotype control. The cells were then washed three times and incubated with a 1:100 dilution of fluorescein isothiocyanate (FITC)-labeled goat anti-mouse immunoglobulin (IgG) (Kirkegaard and Perry Laboratories, Gaithersburg, Md.). The cells were immediately analyzed using a Becton Dickinson FACScan equipped with a blue laser with an excitation of 15 nW at 488 nm. Data were gathered from 10,000 live cells, stored and used to generate results.

(ii) Dual-Color Flow Cytometric Analysis.

The procedure for dual-color flow cytometric analysis was similar to that for single-color analysis with the following exceptions. Anti-MHC-class II FITC/anti-CD11c PE, anti-MHC-class II FITC/anti-CD80 PE, anti-CD58 FITC/anti-CD54 PE, anti-MHC class I FITC/anti-MHC class II PE, and anti-IgG1 FITC/anti-IgG2a PE (isotype controls) were used for the analysis of dendritic cells; >96% of the dendritic cells were CD11c and MHC class II positive.

The antibodies used for the analysis of T cell lines were anti-CD56 FITC/anti-CD8 PE, anti-CD4 FITC/anti-CD8 PE and anti-CD45R0-FITC/anti-CD49d PE; >98% of the T-1191-P92 and T-1191-P-93L cells were CD8 positive. Antibodies to CD4, CD8, CD28, CD45RO, CD56, CD49d, CD54, CD80, CD86, CD58 and CD11c were purchased from BD Biosciences. Antibodies to MHC-class I and MHC-class II were purchased from Serotec, Oxford, UK. Staining was done simultaneously for 1 h, after which cells were washed three times, resuspended as above, and immediately analyzed using a Becton Dickinson FACScan equipped with a blue laser with an excitation of 15 mW at 488 nm with the use of the CELLQuest program.

Results were expressed in % of positive cells and mean fluorescence intensity (MFI). MFI was used to express the levels of fluorescence determined by measuring the average for all the cells in the gated fluorescence dot plot. The MFI value was collected in log scale on the FACSCAN.

Peptide Binding to HLA-A2.

Binding of P-92 and P-92 analogues to HLA-A2 molecules was evaluated by binding to T2A2 cells as demonstrated by flow cytometry. In this assay, increased stability (accumulation) of HLA-A2 molecules on the surface of T2 cells as a consequence of peptide binding is measured by increased binding of antibody directed against HLA-A2 molecule. Briefly, $1\times10^6$ cells in serum-free Iscove's modified Dulbecco's complete medium were incubated with peptides at a concentration of 50 μg/ml in 24-well culture plates at 37° C. in 5% $CO_2$. Flow cytometry for peptide binding was performed using T2 cells and single-color analysis. After cells were washed three times in DPBS, as described above, they were incubated for 1 h with a 1:100 dilution of HLA-A2- specific MAb (One Lambda, Inc.) per $10^6$ cells. UPC-10 (Cappel/Organon Teknika) was used as isotype control. The cells were then washed three times and incubated with 1:100 dilution of FITC-labeled anti-mouse IgG (BD Biosciences). Analysis was conducted with the FACScan, as described above. Cells were maintained on ice during all cell preparation and staining.

Culture of DCs from PBMCs.

HLA-A2 normal donor PBMCs were obtained from heparinized blood. PBMCs were separated using lymphocyte separation medium gradient (Organon Teknika, Durham, N.C.), as described previously (Boyum, A. *Scand. J. Clin. Lab. Invest.* 97(Suppl): 51-76, 1968). DCs were prepared using a modification of the procedure described by Sallusto et al. (*J. Exp. Med.,* 179: 1109-1118, 1994). PBMCs ($1.5 \times 10^8$) were resuspended in AIM-V medium containing 2 mM glutamine, 50 µg/ml streptomycin, and 10 µg/ml gentamycin (Invitrogen Life Technologies, Inc.), and allowed to adhere to a T-150 flask (Corning Costar Corp., Cambridge, Mass.). After 2 h at 37° C., the non-adherent cells were removed with a gentle rinse. The adherent cells were cultured for 6-7 days in AIM-V medium containing 100 ng/ml of recombinant human GM-CSF (rhGM-CSF) and 20 ng/ml of recombinant human IL-4 (rhIL-4). The culture medium was replenished every 3 days.

Recombinant Virus and Infection of DCs with Avipox Virus Containing MUC-1 (rF-MUC-1/TRICOM).

Recombinant fowlpox virus was constructed as described by Jenkins S., et al., *AIDS Res. Hum. Retroviruses,* 7: 991-998, 1991. A plaque-purified isolate from the PDXVAC-TC vaccine strain of fowlpox virus was used as the parental virus for this recombinant virus. The MUC-1, LFA-3, ICAM-1, and B7-1 sequences were inserted into the BamHI, J region of the fowlpox virus genome. In addition, the lacZ gene, under the control of the fowlpox C1 promoter, was included to identify and isolate recombinant viruses using a chromogenic assay for β-galactosidase. The MUC-1 gene that was inserted into fowlpox virus varies from the native MUC-1 gene. It encodes a 30-amino acid signal sequence, followed by the first 38 amino acids of the mature N-terminal sequence of the MUC-1 protein, 10 identical copies of the 20-amino acid repeated sequence, and the C-terminal portion of the protein. The 600 bp repeated sequence was produced using overlapping synthetic oligonucleotides containing codons with numerous third-base variations in each repeat sequence without changing the encoded amino acids. This was done to minimize duplicated nucleotide sequences, which are unstable in pox viruses, while maintaining the repeated amino acid sequences.

rF-MUC-1/TRICOM is a recombinant fowlpox virus that contains the MUC-1 gene under the control of the 40K promoter, the human LFA-3 gene under the control of the vaccinia 30K promoter, the human ICAM-1 gene under the control of the vaccinia I3 promoter, and the human B7-1 gene under the control of the synthetic early/late (sE/L) promoter. Dendritic cells (DCs) ($1 \times 10^6$) were incubated in 1 ml of Opti-MEM medium (Life Technologies, Inc.) at 37° C. with rF-MUC-1/TRICOM or control avipox virus vector (FP-WT). Titration experiments demonstrated that $4 \times 10^7$ plaque-forming units/ml, equal to an MOI of 40:1 for 2 h, were able to consistently induce transgene expression in approximately 75% of the infected DCs. The infected DCs were suspended in 10 ml of fresh, warm RPMI-1640 complete medium containing 100 ng/ml of rhGM-CSF, 20 ng/ml rhIL-4, and 20 ng/ml of TNF-α cultured for 24 h, and then subsequently used as APCs.

Generation of T-Cell Lines.

Modification of the protocol described by Tsang K. Y. et al., *J. Natl. Cancer Inst.,* 87: 982-990, 1995, was used to generate MUC-1-specific CTL. To generate T-cell lines T-1191-P-93L and T-1191-P-92, autologous DCs infected with rF-MUC-1/TRICOM were used as APCs. Autologous non-adherent cells were then added to APCs at an effector-to-APC ratio of 10:1. Cultures were then incubated for 3 days at 37° C. in a humidified atmosphere containing 5% CO2. The cultures were then supplemented with recombinant human IL-2 at a concentration of 20 units/ml for 7 days; the IL-2 containing medium was replenished every 3 days. The 3-day incubation with peptide and 7-day IL-2 supplement constituted one IVS cycle. Primary cultures were restimulated with rF-MUC-1/TRICOM-infected autologous DCs as described above on day 11 to begin the next IVS cycle. rF-MUC-1/TRICOM-infected autologous DCs were used as APCs for three IVS cycles. Irradiated (23,000 rads) autologous EBV-transformed B cells were used as APCs after the third IVS cycle. For the restimulation with EBV-transformed B cells, peptides at a concentration of 50 mg/ml were used to pulse the autologous EBV-transformed B cells at a ratio of effector-to-APC of 1:3 for restimulation. Cultures were then incubated for 3 days at 37° C. in a humidified atmosphere containing 5% CO2. After removal of the peptide containing medium, the cultures were then supplemented with recombinant human IL-2 at a concentration of 20 unit/ml for days. T cell lines from subjects 18 and 23 (T-18-P-92, T-18-P93L, T-23-P-92 and T-23-P93L) were generated by stimulation of PBMCs with autologous DCs pulsed with the P-92 or P93L peptides using the same stimulation protocol as described above. The markers used for the analysis and identification of DCs were CD11c, MHC-class 11, CD80, CD54, CD58 and CD83. CD3 was also used as a negative marker.

Cytotoxic Assay.

Target cells (C1R-A2 or tumor cells) were labeled with 50 µCi of $^{111}$Indium-labeled oxyquinoline (Medi-Physics Inc., Arlington, Ill.) for 15 min at room temperature. Target cells ($0.3 \times 10^4$) in 100 µl of RPMI-1640 complete medium were added to each of 96 wells in flat-bottomed assay plates (Corning Costar Corp). Labeled C1R-A2 target cells were incubated with peptides at the concentration indicated for 60 min at 37° C. in 5% $CO_2$ before adding effector cells. No peptide was used when carcinoma cell lines were used as targets. Effector cells were suspended in 100 µl of RPMI-1640 complete medium supplemented with 10% pooled human AB serum and added to the target cells. The plates were then incubated at 37° C. in 5% $CO_2$ for 4 or 16 h. Supernatant was harvested for gamma counting with the use of harvester frames (Skatron, Inc., Sterling, Va.). Determinations were carried out in triplicate, and standard deviations were calculated. Specific lysis was calculated with the use of the following formula (all values in cpm):

$$\% \text{ lysis} = \frac{\text{Observed release} - \text{Spontaneous release}}{\text{Total release} - \text{Spontaneous release}} \times 100$$

Spontaneous release was determined from wells to which 100 µl of RPMI-1640 complete medium was added. Total releasable radioactivity was obtained after treatment of targets with 2.5% Triton X-100.

Detection of Cytokines.

Supernatants of T cells exposed for 24 h to peptide-pulsed autologous EBV-transformed B cells, in IL-2-free medium at various peptide concentrations, were screened for secretion of IFN-γ using an ELISA kit (R & D Systems, Minneapolis, Minn.). The results were expressed in pg/ml. A CBA system (BD PharMingen, San Diego, Calif.) was also used to determine the secretion of multiple cytokines by specific T cells. The CBA system uses the fluorescence detection by flow cytometry to measure soluble analyses in a particles-based immunoassay. The BD human Th1/Th2 cytokine CBA Kit was used to measure IL-2, IL-4, IL-5, IL-10, TNF-α protein levels in a single sample. The cytokine capture beads were mixed with PE-conjugated detection antibodies and then incubated with recombinant cytokine standards or test samples to form sandwich complexes. The sample results were generated in graphic and tabular format, using BD PharMingen CBA analysis software. The results were expressed in pg/ml.

Statistical Analysis.

Statistical analysis of differences between means was done using a two-tailed paired t test (Stat View statistical software, Abacus Concepts, Berkeley, Calif.).

Toxicity Grading—the NCI Common Toxicity Scale.

If Grade I-II toxicities occur, the subject may continue with the infusion schedule.

If Grade III toxicity occurs, the "drug" is held until the toxicity decreases to Grade I or II, then the infusion is restarted. If Grade III or IV toxicity occurs after the restart, the "drug" infusions are stopped.

If Grade IV toxicity occurs, the subject is scored as having Grade IV toxicity and the next infusion is reduced to the previous dose. If the previous dose causes Grade IV toxicity, then the "drug" is stopped.

If Grade IV toxicity occurs in 1 of 3 subjects at a specific dose level, an additional 3 subjects are entered at that cell-dose level for a total of 6 subjects at that dose level. If 2 of 6 subjects at a cell-dose level develop Grade IV toxicity, this dose is defined as the MTD. The next 3 subjects are given 66% (two-thirds) of the previous cell-dose level. For the purposes of evaluation for dose-escalation, each subject at the same dose level must have received at least 4 of 6 infusions.

Example 2

Novel MUC-1 Binding Motifs

The primary amino acid sequence of human MUC-1 was analyzed for consensus motifs for novel HLA-A2 binding peptides. Twelve 10-mer peptides were identified, consequently synthesized, and studied for binding to the HLA-A2 molecule in a T2 cell binding assay. The amino acid sequences and positions of these 10-mer peptides are shown in Table 1. The CEA CAP1-6D peptide and a NCA peptide were used as a positive and negative control, respectively. The predicted binding of the 12 peptides are also given in Table 1. Three of these peptides (P-92, P-94 and P-1108) were shown to have the highest level of binding in the T2 assay.

TABLE 1

Binding of human MUC-1 peptides to HLA-A2 molecules

| Peptide | Amino acid Position in MUC-1 | Sequence | Predicted binding to HLA-A2* | T2 binding# | SEQ ID NO: |
|---------|------------------------------|----------|------------------------------|-------------|------------|
| P-92    | 92-101                       | ATWGQDVTSV | POS                        | 740         | 1          |
| P-94    | 94-103                       | WGQDVTSVPV | NEG                        | 591         | 8          |
| P-1108  | 1108-1117                    | REGTINVHDV | NEG                        | 482         | 9          |
| P-4     | 4-13                         | GTQSPFFLLL | NEG                        | 467         | 10         |
| P-1105  | 1105-1114                    | LAFREGTINV | NEG                        | 461         | 11         |
| P-1104  | 1004-1013                    | TLASHSTKTD | NEG                        | 442         | 12         |
| P-1069  | 1069-1078                    | LQRDISEMFL | NEG                        | 433         | 13         |
| P-1162  | 1162-1171                    | ALLVLVCVLV | POS                        | 431         | 3          |
| P-1135  | 1135-1144                    | TISDVSVSDV | POS                        | 422         | 4          |
| P-1172  | 1173-1181                    | ALAIVYLIAL | POS                        | 372         | 5          |
| P-1169  | 1169-1178                    | VLVALAIVYL | POS                        | 369         | 6          |
| P-1177  | 1177-1186                    | LIALAVCQC  | POS                        | 338         | 7          |
| CAP1-6D | NA                           | YLSGADLNL  | POS                        | 975         | 38         |
| NCA     | NA                           | YRPGENLNL  | NEG                        | 365         | 39         |

*Predicted binding on the basis of reported motif (37); POS = positive; NEG = negative.

Results are expressed in relative fluorescence. CAP1-6D is an HLA-A2 binding carcinoembryonic antigen peptide that was used as a positive control. NCA peptide was used as a negative control.

NA = not applicable.

Example 3

Establishment of MUC-1 Specific T Cell Lines

Studies were then conducted to determine if MUC-1-specific T-cell lines could be established from PBMCs of an apparently healthy donor. To accomplish this, autologous DCs infected with rF-MUC-1/TRICOM were used as APC. rF-MUC-1/TRICOM is a replication-defective avipox vector containing the transgenes for MUC-1 and for a triad of human costimulatory molecules (B7-1, ICAM-1 and LFA-3, designated TRICOM). rF-MUC-1/TRICOM was shown to efficiently infect human DCs and hyperexpress each of the costimulatory molecules, as well as MUC-1, on the DC surface (Table 2). Approximately 96% of the cells were CD11c and MHC-class II positive.

TABLE 2

Phenotypic analysis of DCs infected with rF-MUC-1/TRICOM

| Dendritic cells infected with | CD80 | CD54 | CD58 | Class I | MUC-1 |
|---|---|---|---|---|---|
| Uninfected | 4.8 (13.6) | 59.5 (62.3) | 68.1 (18.2) | 99.7 (271.8) | 5.0 (95.7) |
| FP/WT | 7.4 (13.3) | 79.3 (83.4) | 74.0 (19.5) | 99.5 (176.3) | 3.1 (50.7) |
| rF-MUC-1/TRICOM | 30.9 (35.7) | 84.5 (133.9) | 79.8 (27.4) | 99.9 (189.3) | 31.6 (213.1) |

Flow cytometric analysis of surface marker expression on DCs. DCs used were cultured in AIM-V medium containing 100 ng/ml of rhGM-CSF and 20 ng/ml of rhIL-4 for 7 days. DCs used for infection with FP/WT or rF-MUC-1/TRICOM were cultured as described in "Materials and Methods." Results indicate the percentage of positive cells; numbers in parentheses represent MFI.

The specificity of the MUC-1-specific T cells generated (designated T-1191-MUC-1) was analyzed after IVS cycle 3 (see Materials and Methods) for their ability to release IFN-γ after stimulation with autologous B cells pulsed with each of the MUC-1 peptides listed in Table 1. The results shown in Table 3 demonstrate that when the T-1191-MUC-1 cells were stimulated with autologous B cells pulsed with peptides P-92, P-1135, P-94, P-1004, P-1069 and P-4, the T cells produced IFN-γ, while the use of autologous B cells pulsed with the other peptides did not result in IFN-γ production. The results shown in Tables 1 and 3 demonstrate that the P-92 peptide had the highest level of T2 binding, as well as the ability to activate T-1191-MUC-1 cells to produce the highest levels of IFN-γ; this peptide was thus chosen for further study.

TABLE 3

Production of IFN-γ by T-1191-MUC-1 cells stimulated with autologous B cells pulsed with MUC-1 peptides

| | Production of IFN-γ (pg/ml) | |
|---|---|---|
| Peptide | With peptide | No peptide |
| P-92 | 380.8 | <52.3 |
| P-1135 | 347.2 | <52.3 |
| P-94 | 323.6 | <52.3 |
| P-1004 | 305.6 | <52.3 |
| P-1069 | 288.0 | <52.3 |
| P-4 | 260.0 | <52.3 |
| P-1105 | <52.3 | <52.3 |
| P-1108 | <52.3 | <52.3 |
| P-1162 | <52.3 | <52.3 |
| P-1169 | <52.3 | <52.3 |
| P-1172 | <52.3 | <52.3 |
| P-1177 | <52.3 | <52.3 |

T-1191-MUC-1 cells were used as effectors at IVS-3. T cells were stimulated with irradiated autologous EBV-transformed B cells pulsed with different MUC-1 peptides at a concentration of 25 μg/ml, and an effector-to-APC ratio of 1:3. Twenty-four-hour culture supernatants were collected and screened for the secretion of IFN-γ.

Example 4

Peptide Analysis

Analysis of the primary and secondary HLA-A2 anchor amino acid residues at positions 2 and 10 of the P-92 peptide revealed that modification of amino acids at these positions could potentially enhance the binding ability of the peptide to the HLA-A2 molecule. Thus, six different analogues of P-92 were synthesized, as shown in Table 4, and tested for their binding ability to T2 cells along with the native P-92 peptide. The CEA CAP-7 (HLA-A3 binding peptide), which has previously been shown not to bind to HLA-A2, was used as a negative control. As shown in Table 4, four of the six analog peptides bound to HLA-A2 at higher levels than the P-92 peptide. Analogues P-93L and P-93I bound HLA-A2 with greatest efficiency.

TABLE 4

MUC-1 peptide analogues

| Amino acid sequence | Initial designation | T2 binding* | SEQ ID NO: |
|---|---|---|---|
| ATWGQDVTSV | P-92 (native) | 510 | 1 |
| A*I*WGQDVTSV | I-93 | 823 | 14 |
| A*L*WGQDVTSV | L-93 | 821 | 19 |
| A*L*WGQDVTS*L* | L-93/L-101 | 736 | 15 |
| A*M*WGQDVTSV | M-93 | 723 | 16 |
| A*M*WGQDVTS*L* | M-93/L-101 | 325 | 17 |
| A*M*WGQDVTS*L* | I-93/L-101 | 280 | 18 |

Amino acid sequences of the parental P-92 peptide (amino acid positions 92-101 of MUC-1) and analogue peptides. Amino acids are shown by the single-letter code. Substitution amino acids are indicated in bold and italic.
*Results are expressed in relative fluorescence values. HLA-A3 peptide (T2 binding = 200) was used as a negative control and CAP1-6D (T2 binding = 875) was used as a positive control.

Figure 1B:
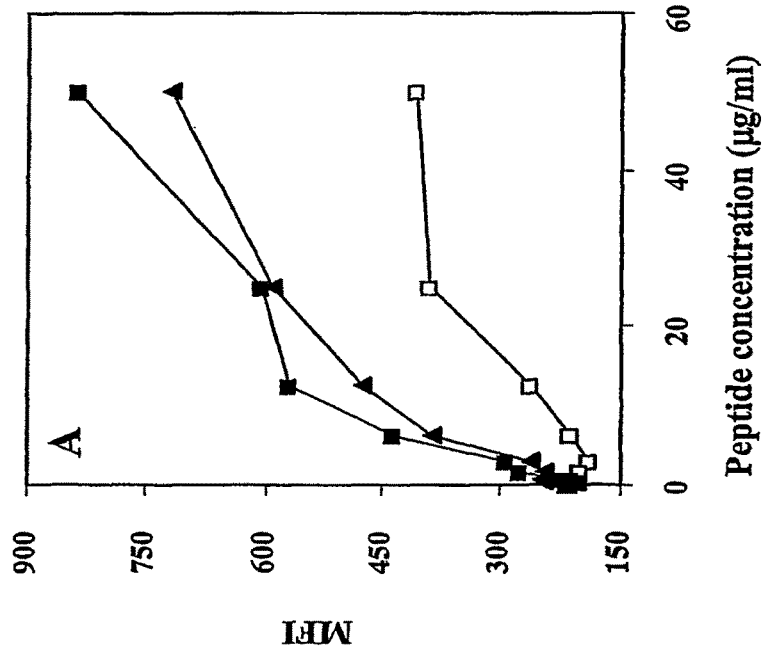

Experiments were then conducted to compare the ability of the P-93L and P-93I peptides to bind HLA-A2 at various peptide concentrations. As seen in FIG. 1, the P-93L and P-93I peptides bound to HLA-A2 at higher levels than P-92 at all peptide concentrations. The levels of binding were similar for P-93L and P-93I at the various peptide concentrations. These data thus indicated that both P-93L and P-93I with modification in the primary anchor position 2 (position 93 of the MUC-1 molecule) were potential agonists of peptide P-92.

Example 5

Stability of Peptide-MHC Complex

Figure 2:
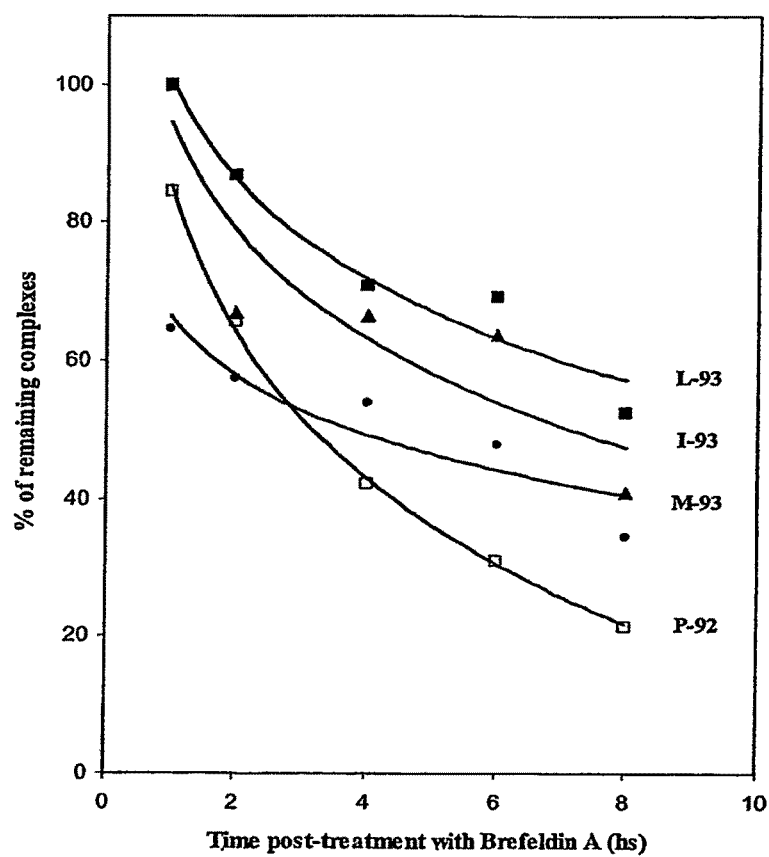
FIG. 2 is a graph showing the comparison of the stability of the complex of the P-92, P-93L or P-93I peptide with HLA-A2. T2 cells were incubated overnight with P-92 (open square), P-93L (closed square) or P-93I (closed triangle) peptide at a concentration of 50 μg/ml and then washed free of unbound peptide and incubated with brefeldin-A to block delivery of new class I molecules to the cell surface. At the indicated times, cells were stained for the presence of surface peptide-HLA-A2 complexes. Results are expressed in relative percentage of binding compared with 100% at time 0.

The stability of the peptide-MHC complex for peptides P-92 (native), P-93L and P-93I, was examined. Peptides were incubated with T2 cells overnight, the unbound peptides were washed off, and then incubated with brefeldin-A to block delivery of new class I molecules to the cell surface; at various time points cells were analyzed for the presence of peptide-HLA-A2 complexes. As shown in FIG. 2, P-93L-HLA-A2 and P-93I-HLA-A2 complexes were more stable than P-92-HLA-A2 complexes over the 8-hour observation period, with P-93L-HLA-A2 complexes slightly more stable than the P-93I-HLA-A2 complexes over the same period of time. Thus, both the binding of peptides to MHC and the stability of the peptide-MHC complex were shown to be greater for the P-93L and P-93I peptides than the native P-92 peptide.

Figure 3:
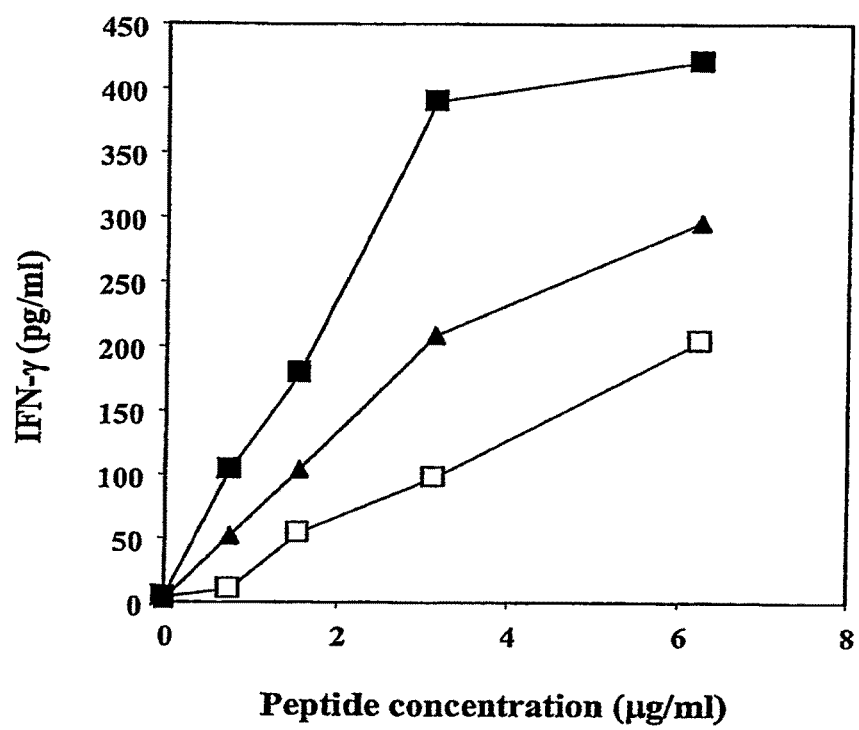
FIG. 3 is a graph showing the ability of autologous B cells pulsed with native MUC-1 peptide P-92 (open square), P-93L peptide (closed square) and P-93I peptide (closed triangle) to induce IFN-γ production by MUC-1-specific T cells. Peptides were used at concentrations of 0-6.25 μg/ml. Results are expressed in pg/ml.

The ability of the P-93L and P-93I agonist peptides at various peptide concentrations, to activate the T-1191-MUC-1 cells, was compared. As seen in FIG. 3, at each concentration of peptide, pulsing of APC with the P-93L peptide led to the greatest level of IFN-γ production by T-1191-MUC-1 cells as compared with the P-93I peptide or the native P-92 peptide. The P-93L agonist peptide was thus chosen for further study. The cytokine profile of T-1191-MUC-1 cells stimulated with APCs pulsed with either the P-92 or the P-93L peptide was then analyzed. A CBA assay was used for the analysis. Table 5 shows the levels of each of the six cytokines produced by T-1191-MUC-1 cell line stimulated with APCs pulsed with no peptide, P-92 peptide and P-93L peptide. These results demonstrated greater production of type 1 cytokine IL-2 and IFN-g by T cells stimulated with the P-93L peptide than with the P-92 peptide. Low or undetectable levels of type 2 cytokines IL-4 and IL-10 were seen with either peptide. No TNF-α could be detected in the supernatants at the 24-h time point.

TABLE 5

CBA assay for the production of cytokines by MUC-1 peptide-stimulated T cells

| Peptide | Cytokines | | | | | |
|---|---|---|---|---|---|---|
| | IL-2 | IL-4 | IL-5 | IL-10 | TNF-α | IFN-γ |
| None | <20 | <20 | <20 | <20 | <20 | <20 |
| P-92 | 58.8 | <20 | <20 | <20 | <20 | 266 |
| P-93L | 366.9 | <20 | 140.9 | <20 | <20 | 650 |

The production of IL-2, IL-4, IL-5, IL-10, TNF-α, and IFN-γ was analyzed. Standards at concentrations of each cytokine at 0 pg/ml, 312 pg/ml and 5000 pg/ml were used to determine the concentrations of these six cytokines in the samples. T-1191 MUC-1 cells at IVS-3 were used as effectors. T cells were stimulated with irradiated autologous EBV-transformed B cells pulsed without peptide or with P-92 or P-93L peptides at a concentration of 25 µg/ml, and an effector-to-APC ratio of 1:3. Twenty-four-hour culture supernatants were collected and screened for the secretion of cytokines. Results are expressed in pg/ml/$10^6$ cell/ml.

Figure 4:
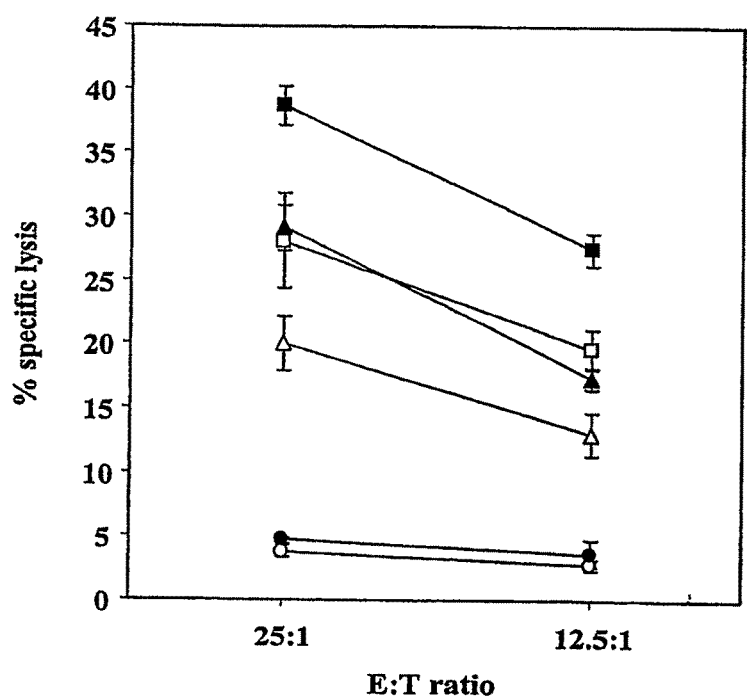
FIG. 4 is a graph showing the cytotoxicity of the MUC-1-specific T-cell lines against C1R-A2 cells pulsed with P-92 and P-93L peptide. T-1191-P-93L against C1R-A2 pulsed with P-93L peptide (closed square), T-1191-P-93L against C1R-A2 pulsed with P-92 peptide (open square), T-1191-P-93L against C1R-A2 pulsed with CAP1-6D peptide (closed circle), T-1191-P-92 against C1R-A2 pulsed with P-93L peptide (closed triangle), T-1191-P-92 against C1R-A2 pulsed with P-92 peptide (open triangle), T-1191-P-92 against C1R-A2 pulsed with CAP1-6D peptide (open circle). E:T ratio=25:1 and 12.5:1 in a 16-h $^{111}$In release assay. Bars=SD.

To further compare the biologic activity of the native P-92 peptide and the agonist P-93L peptide, two additional T-cell lines were established. This was accomplished using as APC autologous DCs infected with rF-MUC-1/TRICOM and autologous PBMCs as effectors from an apparently healthy donor. After three IVS, the T-cell lines were stimulated with autologous B cells pulsed with either the P-92 or the P-93L peptide. These two cell lines were designated T-1191-P-92 and T-1191-P-93L, respectively. The two cell lines were shown to be >98% CD8 positive, 99% CD49d positive, <2% CD56 positive and >75% CD45RO positive cells. The two T-cell lines were then analyzed for their ability to lyse peptide-pulsed targets. T-1191-P-93L was shown to lyse C1R-A2 cells pulsed with P-93L peptide to a greater extent than cells pulsed with the P-92 peptide (FIG. 4, squares). T-1191-P-92 also lysed target cells pulsed with the P-93L peptide to a greater extent than those pulsed with the P-92 peptide (FIG. 4, triangles). The data in FIG. 4 also show that when target cells are pulsed with the native peptide, the T-cell line established with the agonist P-93L peptide lyses target cells at greater levels than the T-cell line established with the native peptide. This was seen at two different E:T ratios. T-1191-P-93L cells and T-1191-P-92 cells did not lyse C1R-A2 cells when pulsed with control CEA CAP1-6D peptide (FIG. 4, circles).

Example 6

Target Cell Recognition

Studies were the conducted to determine whether these two T-cell lines could lyse the MUC-1 positive and HLA-A2 positive breast carcinoma cell line MCF-7. The MUC-1 negative HLA-A2 positive SK-Mel-24 melanoma cell line was used as a negative control. As shown in Table 5, MCF-7 cells were lysed by both the T-1191-P-92 and T-1191-P-93L cells. No lysis was observed against the SK-Mel-24 cells. T-1191-P-93L cells were shown to lyse MCF-7 cells to a greater degree as compared with the T-1191-P-92 cell line. The addition of unlabeled C1R-A2 cells pulsed with the corresponding MUC-1 peptide, but not the CEA CAP1-6D control peptide, decreased the cytotoxic activity of both T-cell lines, demonstrating the MUC-1 specificity of the lysis (Table 5). The cytotoxic activity of these T-cell lines against MCF-7 cells was also shown to be HLA-A2-restricted, as demonstrated by the inhibition of lysis with the addition of anti-HLA-A2 antibody, but not with the control antibody UPC-10 (Table 6).

TABLE 6

Ability of MUC-1-specific T-cell lines T-1191-P-92 and T-1191-P-93L to lyse a MUC-1-expressing tumor cell line (MCF-7)

| Target | T-1191-P-92 | T-1191-P-93L |
|---|---|---|
| MCF-7 | 16.5 (2.7)* | 24.5 (4.5)* |
| MCF-7 + C1R-A2 | 15.6 (3.2)* | 21.6 (2.9)* |
| MCF-7 + C1R-A2 + P-92 | 4.2 (2.2) | 6.1 (1.9) |
| MCF-7 + C1R-A2 + P-93L | 3.0 (1.5) | 3.5 (1.2) |
| MCF-7 + C1R-A2 + CAP1-6D | 17.1 (3.8)* | 20.8 (3.9)* |
| SK-Mel-24 | 0.5 (1.1) | 1.4 (0.8) |

Results are expressed in % of specific lysis at E:T = 25:1. The numbers in parentheses are the standard deviation. MCF-7 (human breast carcinoma cell line) cells are MUC-1 positive and HLA-A2 positive. SK-Mel-24 (melanoma) cells are MUC-1 negative and HLA-A2 positive. T-1191-P-92 cells and T-1191-P-93L cells were used at IVS-5. The T-1191-P-92 cell line was passaged on the native P-92 peptide, while the T-1191-P-93 cell line was passaged on the agonist P-93L peptide, from IVS 3 to IVS 5. MCF-7 cells were labeled with $^{111}$In. Labeled MCF-7 cells and unlabeled C1R-A2 cells were used at a ratio of 1:10. C1R-A2 cells were incubated with or without P-92 peptide (25 µg/ml), P-93L peptide (25 µg/ml) or CAP1-6D control peptide (25 µg/ml).
*Statistically significant lysis (p < 0.01, two-tailed t test) when comparing lysis of MCF-7 cells versus SK-Mel-24 cells. There is also a statistical significance (p < 0.01, two-tailed t test) when comparing lysis of MCF-7 + C1R-A2 versus MCF-7 + C1R-A2 + P-92 peptide or MCF-7 + C1R-A2 versus MCF-7 + C1R-A2 + P-93L.

The cytotoxic activity of these T-cell lines against MCF-7 cells was also shown to be HLA-A2-restricted, as demonstrated by the inhibition of lysis with the addition of anti-HLA-A2 antibody, but not with the control antibody UPC-10 (Table 7).

The T-1991-P-92 and T-1191-P-93L T-cell lines were derived from an apparently healthy subject. Studies were then conducted to determine if additional T-cell lines could be established from two subjects with pancreatic cancer (subjects 23 and 18). Four MUC-1-specific T-cell lines were generated and were designated T-23-P-92, T-23-P-93L, T-18-P-92 and T-18-P-93L. The T-cell lines T-18-P-92 and T-18-P-93L were generated from subject 18 by stimulation of PBMCs with autologous DCs pulsed with the P-92 and P-93L peptides, respectively. T-cell lines T-23-P-92 and T-23-P-93L were generated from subject 23 by stimulation of PBMCs by autologous DCs pulsed with the P-92 and P-93L peptides, respectively. As seen in Table 8, all four T-cell lines from both pancreatic cancer subjects could be stimulated to produce IFN-γ when stimulated with DCs pulsed with either the P-92 or the P-93L peptide. No IFN-γ production was observed, however, when these T cells were stimulated in a similar manner with the CEA peptide CAP1-6D. For all four T-cell lines, greater levels of IFN-γ production were seen when the P-93L agonist peptide was used as compared with the P-92 native peptide. It also should be noted that the T-cell lines derived using the agonist peptide always showed higher levels of stimulation than the T-cell lines derived from the native peptide, when a given peptide was used for stimulation.

TABLE 8

Production of IFN-γ by T-cell lines generated from two pancreatic cancer subjects, stimulated with P-92, and agonist P-93L peptide

| | Peptide | | |
|---|---|---|---|
| T-cell line | P-92 | P-93L | CAP1-6D |
| T-23-P-92 | 299.8 | 644.5 | <26 |
| T-23-P-93L | 400.5 | 973.0 | <26 |
| T-18-P-92 | 168.0 | 366.6 | <26 |
| T-18-P-93L | 378.2 | 524.1 | <26 |

$^a$Results are expressed as pg IFN-γ produced.
Cells from four MUC-1-specific T-cell lines established from two pancreatic cancer subjects (subjects 23 and 18) were used as effector cells at IVS-4. These T-cell lines were established by stimulation with P-92-pulsed autologous DCs (T-23-P-92 and P-18-P-92) or P-93L pulsed autologous DCs (T-23-P-93L and T-18-P-93L). For IFN-γ production, T-cell lines were stimulated with irradiated HLA-A-positive allogeneic DCs pulsed with either P-92 or P-93L peptide at a concentration of 25 µg/ml and an effector-to-APC ratio of 10:1. Twenty-four-hour culture supernatants were collected and screened for the secretion of IFN-γ.

Example 7

Cytolysis of Targets by Cancer Subject Derived Cell Lines

Studies were then conducted to determine if the T-cell lines derived from cancer subject 23 could lyse MUC-1 positive HLA-A2 positive cancer cells. The SK-Mel-24 cell line (MUC-1 negative and HLA-A2 positive) was used as a negative control for specificity. As can be seen in Table 9 and 10, the T-23-P-93L line, T-23-P-92 line, T-18-P-93L line and T-18-P-92 line showed lysis of the MCF-7 carcinoma cells at two different E:T ratios, but showed no lysis of the melanoma cell line. In concordance with the results shown above, the T-cell line (T-23-P-93L, T-18-P-93L) derived using the agonist peptide demonstrated greater lysis of the tumor cells than the T-cell line (T-23-P-92, T-18-P-92) derived using the native peptide. This was seen at two different E:T ratios.

TABLE 9

Ability of T-cell lines from a pancreatic cancer subject, generated with agonist peptide P-93L, to lyse cancer cells expressing native MUC-1

| | | E:T Ratios | |
|---|---|---|---|
| T-cell line | Target | 25:1 | 12.5:1 |
| T-23-P-93L | MCF-7 | 24.6 (1.0)*# | 17.9 (0.2)*# |
| T-23-P-93L | SK-Mel-24 | 1.3 (1.1) | 0.8 (0.6) |
| T-23-P-92 | MCF-7 | 14.4 (0.6)* | 10.1 (0.8)* |
| T-23-P-92 | SK-Mel-24 | 0.5 (1.6) | 0.4 (1.9) |

*Statistical significance (P < 0.01, two-tailed t test) when comparing lysis of MCF-7 cells versus SK-Mel-24 cells by T-23-P-93L and T-23P-92 cells.
Statistical significance (P < 0.01, two-tailed t test) when comparing lysis of MCF-7 cells by T-23-P-93L and T-23-P-92 cells.
Results are expressed as % lysis.

TABLE 10

Ability of T cells from a pancreatic cancer subject generated with agonist peptide P-93L to lyse cancer cells expressing native MUC-1

| | | E:T Ratios | |
|---|---|---|---|
| T-cell line | Target | 25:1 | 12.5:1 |
| T-18-P-93L | MCF-7 | 25 (0.8)*# | 14.6 (0.5)*# |
| T-18-P-93L | SK-Mel-24 | 1.1 (0.9) | 1.0 (0.8) |
| T-18-P-92 | MCF-7 | 12.1 (0.3)* | 8.4 (0.4)* |
| T-18-P-92 | SK-Mel-24 | 0.9 (1.4) | 1.0 (1.2) |

*Statistical significance (P < 0.01, two-tailed t test) when comparing lysis of MCF-7 cells versus SK-Mel-24 cells by T-18-P-93L and T-18-P-92 cells.
Statistical significance (P < 0.01, two-tailed t test) when comparing lysis of MCF-7 cells by T-18-P-93L and T-18-P-92 cells.

Example 8

Materials and Methods

The two viral vectors analyzed are the replication competent recombinant vaccinia virus (rV-), and the avipox vector, fowlpox (rF-), which is replication incompetent in mammalian cells. Each vector encodes the transgenes for three human costimulatory molecules (B7-1, ICAM-1, LFA-3, designated TRICOM); both the CEA and MUC-1 transgenes also contain agonist epitopes. The vectors are designated rV-CEA/MUC/TRICOM and rF-CEA/MUC/TRICOM.

Each of the vectors is shown to be capable of faithfully expressing all five transgenes in human dendritic cells (DCs). DCs infected with either vector are shown to activate both CEA-specific and MUC-1-specific T-cell lines to the same level as DCs infected with CEA-TRICOM or MUC-1-TRICOM vectors. Thus, no evidence of antigenic competition between CEA and MUC-1 was observed. Human DCs infected with rV-CEA/MUC/TRICOM or rF-CEA/MUC/TRICOM are also shown to be capable of generating both MUC-1 and CEA-specific T-cell lines; these T-cell lines are in turn shown to be capable of lysing targets pulsed with MUC-1 or CEA peptides, as well as human tumor cells endogenously expressing MUC-1 and/or CEA.

Cell Cultures

The human breast adenocarcinoma cell line MCF-7 (HLA-A2 positive, CEA negative and MUC-1 positive), the colorectal carcinoma cell line SW1463 (HLA-A2 positive, CEA positive and MUC-1 positive), and the melanoma cell line SKMel-24 (HLA-A2 positive, CEA negative and MUC-1 negative) were purchased from American Type Culture Collection (Manassas, Va.). The cultures were free of mycoplasma and were maintained in complete medium [RPMI 1640 (Invitrogen Life Technologies, Inc., Carlsbad, Calif.) supplemented with 10% fetal bovine serum, 2 mM glutamine, 100 units/ml penicillin, and 100 µg/ml streptomycin (Invitrogen Life Technologies)]. The C1R cell line is a human plasma leukemia cell line that does not express endogenous HLA-A or B antigens. C1R-A2 cells are C1R cells that express a transfected genomic clone of HLA-A2.1. These cells were obtained from Dr. William E. Biddison (National Institute of Neurological Disorders and Stroke, NIH, Bethesda, Md.). The 174CEM-T2 cell line (T2) transport deletion mutant was provided by Dr. Peter Cresswell (Yale University School of Medicine, New Haven, Conn.). C1R-A2 cells and T2 cells were mycoplasma free and were maintained in RPMI 1640 complete medium and Iscove's modified Dulbecco's complete medium (Invitrogen Life Technologies), respectively. The V8T cell line is a CD8+ CTL line directed against the CAP-1 epitope of CEA. The T-1191-P93L cell line is a CD8+ MUC-1-specific CTL line generated from peripheral blood mononuclear cells (PBMCs) from a healthy donor that was in vitro stimulated using a MUC-1 peptide. Both V8T and T-1191-P93L cell lines were cultured as described previously.

Peptides

HLA-A2 binding peptides used included: (a) the CEA agonist peptide CAP1-6D (YLSGADLNL) (SEQ ID NO: 38), designated CEA peptide, (b) the MUC-1 agonist peptide P-93L (ALWGQDVTSV) (SEQ ID NO: 2), designated MUC-1 peptide, (c) the prostate-specific antigen (PSA) peptide PSA-3 (VISNDVCAQV) (SEQ ID NO: 40). All peptides were greater than 96% pure and manufactured by American Peptide Company, Inc. (Sunnyvale, Calif.).

Culture of DCs from PBMCs

HLA-A2 normal donor PBMCs were obtained from heparinized blood. PBMCs were separated using lymphocyte separation medium gradient (Organon Teknika, Durham, N.C.), as described previously (51) (Boyum A. A one-stage procedure for isolation of granulocytes and lymphocytes from human blood. General sedimentation properties of white blood cells in 1 g gravity field, Scand J Clin Lab Invest 1968; 97(Suppl):51-76). DCs were prepared using a modification of the procedure described by Sallusto et al. Sallusto F, Lanzavecchia A., Efficient presentation of soluble antigen by cultured human dendritic cells is maintained by granulocyte/macrophage colony stimulating factor plus interleukin-4 and down-regulated by tumor necrosis factor alpha., J Exp Med 1994; 179:1109-18. PBMCs ($1.5 \times 10^8$) were resuspended in AIM-V medium containing 2 mM glutamine, 50 µg/ml streptomycin, and 10 µg/ml gentamycin (Invitrogen Life Technologies), and allowed to adhere to a T-150 flask (Corning Costar Corp., Cambridge, Mass.). After 2 hours at 37° C., the non-adherent cells were removed with a gentle rinse. The adherent cells were cultured for 6-7 days in AIM-V medium containing 100 ng/ml of recombinant human GM-CSF (rhGM-CSF) and 20 ng/ml of recombinant human IL-4 (rhIL-4). The culture medium was replenished every 3 days.

Recombinant Virus and Infection of DCs with rV-CEA/MUC/TRICOM and rF-CEA/MUC/TRICOM Both rV-CEA/MUC/TRICOM and rF-CEA/MUC/TRICOM encode the human CEA gene containing the 6D modification, the human MUC-1 gene containing the 93L modification and the genes for the human costimulatory molecules B7-1, ICAM-1, and LFA-3 (FIG. 5) (Zaremba S, Barzaga E, Zhu M et al. Identification of an enhancer agonist cytotoxic T lymphocyte peptide from human carcinoembryonic antigen. Cancer Res 1997; 57:4570-7, and Tsang K Y, Palena C, Gulley J, Arlen P, Schlom J. A human cytotoxic T-lymphocyte epitope and its agonist epitope from the non-variable number of tandem repeat sequence of MUC-1. Clin Cancer Res 2004; 10:2139-49) Recombinant vectors were generated by homologous recombination as described previously (Hodge J W, McLaughlin J P, Kantor J A, Schlom J. Diversified prime and boost protocols using recombinant vaccinia virus and recombinant nonreplicating avian pox virus to enhance T-cell immunity and antitumor responses. Vaccine 1997; 16:759-68). DCs ($1 \times 10^6$) were incubated in 1 ml of Opti-MEM medium (Invitrogen Life Technologies) at 37° C. with rF-CEA/MUC/TRICOM, rV-CEA/MUC/TRICOM, control avipox virus vector (FP-WT) or control vaccinia vector (V-WT). Titration experiments demonstrated that infection of DCs for 2 hours with $4 \times 10^7$ plaque-forming units (pfu)/ml of rF-CEA/MUC/TRICOM, equal to a multiplicity of infection (MOI) of 40 pfu/cell was able to consistently induce transgene expression in approximately 60% of the infected DCs. Similar titration experiments demonstrated that infection of DCs for 1 hour with $0.5 \times 10^7$ pfu/ml of rV-CEA/MUC/TRICOM, equal to an MOI of 5 pfu/cell, was able to consistently induce transgene expression in approximately 35% of the infected DCs. DCs from different donors were used for the infections with rF-CEA/MUC/TRICOM and rV-CEA/MUC/TRICOM, with the efficiency of infection ranging from 50%-65% for rF-CEA/MUC/TRICOM and 30%-59% for rV-CEA/MUC/TRICOM. The infected DCs were suspended in 10 ml of fresh, warm RPMI-1640 complete medium containing 100 ng/ml of rhGM-CSF and 20 ng/ml of rhIL-4, cultured for 24 hours, and subsequently used as APC.

Flow Cytometric Analysis

Dual-color flow cytometric analysis was performed on T cell lines by using the following antibody combinations: anti-CD56-FITC/anti-CD8-PE, anti-CD8-FITC/anti-CD45RA-FITC, and anti-CD8-FITC/anti-CD27-PE. Antibodies were all purchased from BD Biosciences (San Jose, Calif.). Staining was conducted simultaneously for 1 hour at 4° C., cells were then washed three times with cold $Ca^{2+}$ and $Mg^{2+}$ free phosphate-buffered saline (PBS), resuspended in the same buffer, and 11 immediately analyzed using a FACScan and the CELLQuest program (BD Biosciences). Data were gathered from 10,000 live cells, stored, and used to generate results. The procedure for analysis of DCs was similar to the one described above. The following antibody combinations were used: anti-MHC-class II-FITC/anti-CD80-PE, anti-CD58-FITC/anti-CD54-PE, anti-MHC class I-FITC/anti-MHC class II-PE, and anti-IgG1-FITC/anti-IgG2a-PE (isotype controls). Antibodies to MHC-class I and II were purchased from Serotec (Oxford, UK); other antibodies were purchased from BD Biosciences. The anti-CEA monoclonal antibody COL-1 and anti-MUC-1 antibodies (DF3 and DF3-P) were also used (Muraro R, Wunderlich D, Thor A, et al. Definition by monoclonal antibodies of a repertoire of epitopes on carcinoembryonic antigen differentially expressed in human colon carcinoma versus normal adult tissues. Cancer Res 1985; 45:5769-80). MOPC-104E (IgM) (Cappel/Organon Teknika Corp., West Chester, Pa.) was used as negative control.

After staining, cells were washed three times and subsequently incubated with a 1:100 dilution of FITC-labeled goat anti-mouse immunoglobulin (IgG) (Kirkegaard and Perry Laboratories, Gaithersburg, Md.). Analysis was conducted as described above. Results were expressed in percentage of positive cells and mean fluorescence intensity (MFI). The MFI value was collected in log scale, and was used to express the levels of fluorescence determined by measuring the average for all the cells in the fluorescence dot plot.

Immune Blot Analysis

Uninfected DCs, DCs infected with 40 MOI of rF-CEA/MUC/TRICOM, rF-CEA(6D)-TRICOM or rF-MUC-1-TRICOM vectors, and DCs infected with 5 MOI of the rV-CEA/MUC/TRICOM vector were lysed by using the MPER Mammalian Protein Extraction Reagent (Pierce, Rockford, Ill.). Protein concentration of the lysates was determined by using a MicroBCA Protein Assay Kit (Pierce), and 20 µg-fractions of protein per sample were blotted onto a PVDF membrane 12 using a Bio-Dot Microfiltration apparatus (Bio-Rad Laboratories, Hercules, Calif.), following the manufacturer's instructions. After blotting, the membranes were blocked for 1 hour at room temperature with PBS containing 5% BSA (Biosource International, Camarillo, Calif.). Membranes were then washed three times with PBS containing 0.25% Tween-20, and incubated for 2 hours at room temperature with a solution at 1 µg/ml of COL-1, DF-3 or DF3-P antibodies. Membranes were then washed three times as above, and incubated with a 1:3000 dilution of an anti-mouse IgG conjugated to HRP (Kirkegaard & Perry Laboratories) for 1 hour at room temperature. For immunodetection of the CEA and MUC-1 proteins, the SuperSignal West Pico Chemiluminescent Substrate was used (Pierce).

Generation of T-Cell Lines

Modification of the protocol described by Tsang et al. was used to generate CEA and/or MUC-1-specific CTL (Tsang K Y, Zaremba S, Nieroda C A, et al. Generation of human cytotoxic T cells specific for human carcinoembryonic antigen epitopes from patients immunized with recombinant vaccinia-CEA vaccine. J Natl Cancer Inst 1995; 87:982-90). To generate T-cell lines T-rV and T-rF, autologous DCs infected with rV-CEA/MUC/TRICOM or rF-CEA/MUC/TRICOM, respectively, were used as APC. Autologous non-adherent cells were added to APC at an effector-to-APC ratio of 10:1; cultures were incubated for 3 days at 37° C., in a humidified atmosphere containing 5% $CO^2$. The cultures were then supplemented with recombinant human IL-2 at a concentration of 20 units/ml for 7 days; the IL-2 containing medium was replenished every 3 days. The 3-day incubation with peptide and 7-day IL-2 supplement constituted one in vitro stimulation (IVS) cycle. T-rV and T-rF were restimulated with rV-CEA/MUC/TRICO- or rF-CEA/MUC/TRICOM-infected autologous DCs, respectively, as described above, on day 11 to begin the next IVS cycle. rV-CEA/MUC/TRICOM- and rF-CEA/MUC/TRICOM-infected autologous DCs were used as APC for three IVS cycles. For the generation of T-rF(CEA) and T-rF(MUC) cell lines, T cells were stimulated with autologous DCs infected with rF-CEA/MUC/TRICOM for one IVS, and then restimulated with uninfected autologous DCs pulsed with CAP1-6D or P-93L peptide, respectively, for two more IVS. After the third IVS cycle, irradiated (23,000 rads) autologous EBV-transformed B cells were used as APC. The EBV-transformed B cells were pulsed with 25 $\propto$g/ml of peptide, and used for restimulation at an effector-to-APC ratio of 1:3.

Cultures were then incubated for 3 days at 37° C. in a humidified atmosphere containing 5% $CO_2$. After removal of the peptide containing medium, the cultures were supplemented with recombinant human IL-2 at a concentration of 20 units/ml for 7 days. T-cell lines from patients 55, 49 and 41 were generated by stimulation of PBMCs with autologous DCs infected with rF-CEA/MUC/TRICOM, using the same stimulation protocol described above. Patient 55 initially underwent a Whipple procedure for localized pancreatic cancer followed by adjuvant radiation therapy to the pancreatic bed. The patient had local recurrence and received chemotherapy with 5FU/Leucovorin followed by an experimental vaccine study using both vaccinia-CEA and ALVAC-CEA prior to enrolling on this clinical trial. Patient 41 was diagnosed with colorectal carcinoma with liver metastasis. Prior to enrolling on study, this patient progressed on three different chemotherapy regimens, including 5FU/Leucovorin/CPT-11, 5FU/Leucovorin/Oxalliplatin, and XELODA™ (Capecitabine). Patient 49 had colorectal cancer with both liver and lung metastasis. The patient progressed following four cycles of chemotherapy with CPT-11/5FU/Leucovorin prior to enrolling on study.

Cytotoxic Assay

Target cells (C1R-A2 or tumor cells) were labeled with 50 µCi of [111]Indium-labeled oxyquinoline (Medi-Physics Inc., Arlington, Ill.) for 15 minutes at room temperature. Target cells ($0.3 \times 10^4$) in 100 µl of RPMI-1640 complete medium were added to each of 96 wells in flat-bottomed assay plates (Corning Costar Corp). Labeled C1R-A2 target cells were incubated with peptides at the concentration indicated for 60 minutes at 37° C. in 5% $CO_2$ before adding effector cells. No peptide was used when carcinoma cell lines were used as targets. Effector cells were suspended in 100 µl of RPMI-1640 complete medium supplemented with 10% pooled human AB serum and added to the target cells. The plates were then incubated at 37° C. in 5% $CO_2$ for 6 or 16 hours. Supernatant was harvested for gamma counting with the use of harvester frames (Skatron, Inc., Sterling, Va.). Determinations were carried out in triplicate, and standard deviations were calculated. Specific lysis was calculated with the use of the following formula (all values in cpm):

% lysis=(Observed release−Spontaneous release/Total release−Spontaneous release)×100.

Spontaneous release was determined from wells to which 100 µl of RPMI-1640 complete medium was added. Total releasable radioactivity was obtained after treatment of targets with 2.5% Triton x-100.

Detection of Cytokines

Supernatants of T cells exposed for 24 hours to peptide-pulsed autologous EBV-transformed B cells in IL-2-free medium, at various peptide concentrations, were screened for secretion of IFN-α using an ELISA kit (Biosource International). The results were expressed in pg/ml.

Statistical Analysis

Statistical analysis of differences between means was done using a two-tailed paired t test (Stat View statistical software, Abacus Concepts, Berkeley, Calif.).

Figure 6:
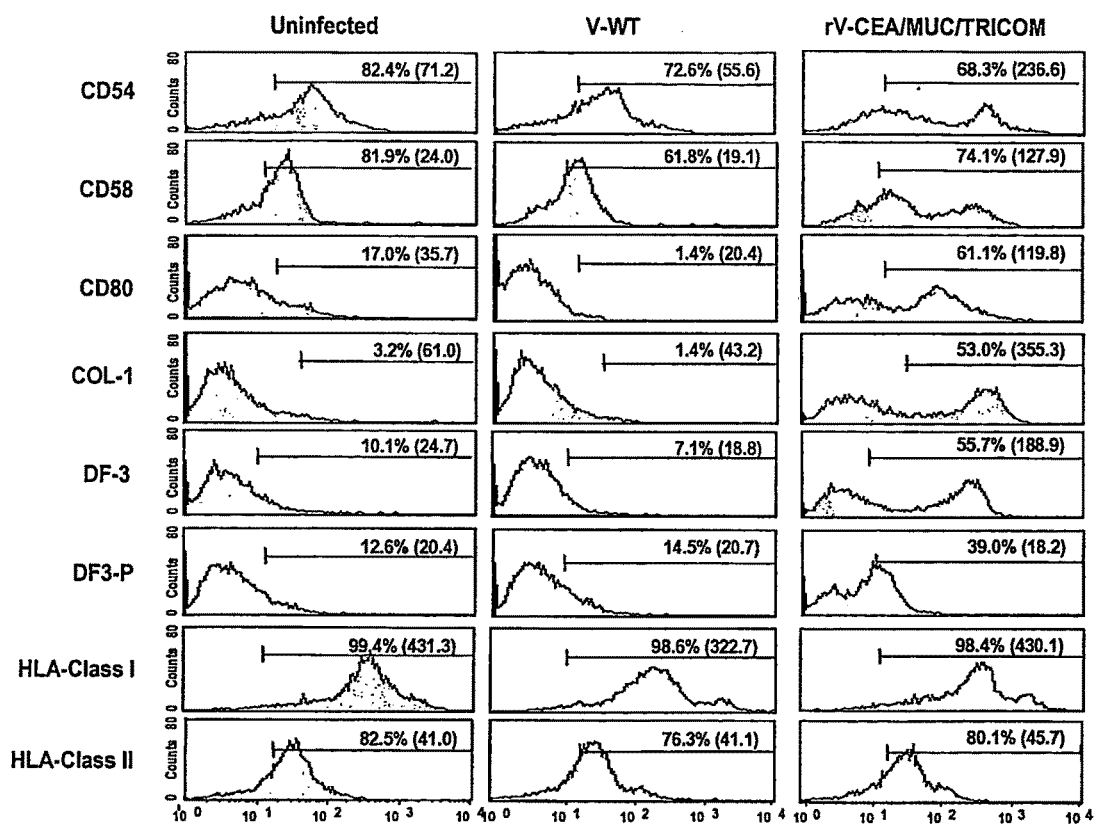
FIG. 6 is a graphical representation of a flow cytometric analysis of surface marker expression on human DCs uninfected, infected with control vector (V-WT), or infected with rV-CEA/MUC/TRICOM. DCs (1×10⁶) were incubated in 1 ml of Opti-MEM medium at 37° C. with rV-CEA/MUC/TRICOM or control vector (V-WT) for 1 hour, at an MOI of 5:1. The infected DCs were suspended in 10 ml of fresh, warm complete medium containing 100 ng/ml of rhGM-CSF and 20 ng/ml of rhIL-4, and then cultured for 24 hours. Numbers in each histogram indicate the percentage of positive cells and the mean fluorescence intensity (in parentheses).

Studies were first undertaken to determine if infection of human DCs with rV-CEA/MUC/TRICOM would result in the expression of each of the five transgenes. Initial studies used an MOI of 5 and 10 for rV-CEA/MUC/TRICOM; both MOI gave comparable results and thus an MOI of 5 was used in subsequent experiments. As seen in FIG. 6, uninfected human DCs do not express CEA (as detected by monoclonal antibody COL-1); expression of CD80, CD54, and CD58, MHC Class I and MHC Class II by DCs is similar to that previously reported in several studies (Tsang K Y, Zhu M Z, Even J., et al., The infection of human dendritic cells with recombinant avipox vectors expressing a costimulatory molecule transgene (CD80) to enhance the activation of antigen-specific cytotoxic T cells. Cancer Res 2001; 61:7568-76; and Zhu M Z, Terasawa H, Gulley J, et al. Enhanced activation of human T cells via avipox vector-mediated hyperexpression of a triad of costimulatory molecules in human dendritic cells. Cancer Res 2001; 61:3725-34). Infection with V-WT had little, if any, effect on any of these eight surface markers (FIG. 6). Infection with rV-CEA/MUC/TRICOM, however, is shown to substantially increase the level of expression of CEA, MUC-1, CD80, CD54 and CD58, and did not measurably affect the level of expression of MHC Class I and Class II. Consistent with results previously published, infection of DCs from the same donor with rV-CEA(6D)-TRICOM enhanced the level of CEA, CD80, CD54, and CD58 to levels similar to those seen with rV-CEA/MUC/TRICOM, but did not alter the expression of MUC-1 or MHC Class I or Class II. In addition, infection of DCs with rV-MUC-1 admixed with rV-TRICOM (rV-MUC-1-TRICOM construct was not available) showed levels of enhanced expression of MUC-1 and the three costimulatory molecules similar to those seen with rV-CEA/MUC/TRICOM, but had no effect on the level of expression of MHC Class I and Class II, and on the lack of expression of CEA (data not shown). Low levels of MUC-1 were detected in the uninfected and control vector-infected DCs. This is in agreement with that reported by Wykes et al., which showed that MUC-1 is expressed on human DCs and monocytederived DCs when cultured in vitro (Wykes M, MacDonald K P, Tran M, et al. MUC1 epithelial mucin (CD227) is expressed by activated dendritic cells. J Leukoc Biol 2002; 72:692-701.)

Figure 8:
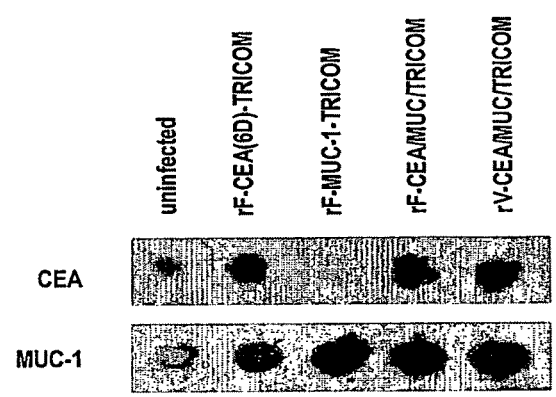
FIG. 8 shows an immunoblotting analysis of human DCs uninfected or infected with rF-CEATRICOM, rF-MUC-1-TRICOM, rF-CEA/MUC/TRICOM and rV-CEA/MUC/

Parallel studies were undertaken to determine if infection of human DCs with rF-CEA/MUC/TRICOM would result in the expression of each of the five transgenes. Initial studies used an MOI of 20 and 40 for rF-CEA/MUC/TRICOM; an MOI of 40 showed greater expression of transgenes and was thus used in subsequent experiments. As seen in FIG. 7, infection with FP-WT had little, if any, effect on any of the eight surface markers analyzed. Infection with rF-CEA/MUC/TRICOM, however, was shown to substantially increase the level of expression of CEA, MUC-1, CD80, CD54 and CD58, but did not affect the level of expression of MHC Class I and Class II. Infection of DCs from the same donor with rF-CEA(6D)-TRICOM enhanced the level of CEA, CD80, CD54, and CD58 to similar levels as seen with rF-CEA/MUC/TRICOM, but did not alter the expression of MUC-1 or MHC Class I or Class II. In addition, infection of DCs with rF-MUC-1-TRICOM showed similar levels of enhanced expression of MUC-1 and the three costimulatory molecules as seen with rF-CEA/MUC/TRICOM, but had no effect on the level of expression of MHC Class I and Class II and the lack of expression of CEA (data not shown). The expression of CEA and MUC-1 on DCs infected with rF-CEA/MUC/TRICOM, rF-CEA(6D)-TRICOM, rF-MUC-1-TRICOM vector or uninfected DCs was analyzed by immune blot analysis. As shown in FIG. 8, CEA was detected in DCs infected with rF-CEA(6D)-TRICOM, rF-CEA/MUC/TRICOM, and rV-CEA/MUC/TRICOM, but not in uninfected DCs or rF-MUC-1-TRICOM-infected DCs. As described above, DCs express a low level of MUC-1, but a great increase in MUC-1 expression was clearly observed in DCs infected with rF-MUC-1-TRICOM, rV-CEA/MUC/TRICOM, and rF-CEA/MUC/TRICOM, but not in DCs infected with rF-CEA(6D)-TRICOM (FIG. 8).

We have demonstrated the ability of DCs pulsed with the CEA agonist peptide CAP-1(6D) and the MUC-1 agonist peptide P-93L to activate human T cells. Studies were undertaken to determine if infection of human DCs with the rF-CEA/MUC/TRICOM vector could stimulate IFN-γ production by CEA-specific and MUC-1-specific T cells. These results were also compared with the ability of human DCs infected with rF-CEA(6D)-TRICOM or rF-MUC-1-TRICOM to activate these T cells. As seen in Table 11, uninfected DCs or DCs infected with FP-WT did not result in any IFN-γ production by the CEA-specific T-cell line (V8T), or the MUC-1-specific T cell line (T-1191-P93L). DCs pulsed with the CEA peptide induced IFN-γ production only by the CEA-specific T-cell line, while DCs pulsed with the MUC-1 peptide induced IFN-γ production only by the MUC-1-specific T-cell line. Similarly, DCs infected with rF-CEA(6D)-TRICOM induced IFN-γ production only by the CEA-specific T-cell line, while DCs infected with the rF-MUC-1-TRICOM induced IFN-γ production only by the MUC-1-specific T-cell line. Infection of DCs with rF-CEA/MUC/TRICOM, however, induced IFN-γ production in both the CEA-specific T-cell line and the MUC-1-specific T-cell line, and at comparable levels to those seen when using the vectors containing only the single tumor-antigen transgene. These studies may demonstrate the lack of antigenic competition between CEA and MUC-1 in the rF-CEA/MUC/TRICOM vector in the ability to activate T cells.

Studies were then undertaken to determine if infection of human DCs with the rV-CEA/MUC/TRICOM vector could stimulate IFN-γ production 19 by the CEA-specific and MUC-1-specific T cells. These results were also compared with the ability of human DCs infected with rV-CEA(6D)-TRICOM, or rV-MUC-1 plus rV-TRICOM, to activate those T cells. As seen in Table 12, uninfected DCs or DCs infected with V-WT did not result in any IFN-γ production by the CEA-specific T-cell line or the MUC-1-specific T-cell line. DCs pulsed with the CEA peptide induced IFN-γ production only by the CEA-specific T-cell line, while DCs pulsed with the MUC-1 peptide induced IFN-γ production only by the MUC-1-specific T-cell line. Similarly, DCs infected with rV-CEA(6D)-TRICOM induced IFN-γ production only by the CEA-specific T-cell line, while DCs infected with the MUC-1 vectors induced IFN-γ production only in the MUC-1-specific T-cell line. Infection of DCs with rV-CEA/MUC/TRICOM, however, induced IFN-γ production in both the CEA-specific T-cell line and the MUC-1-specific T-cell line and at comparable levels to those seen when using the vectors containing only the single tumor-antigen transgene. These studies may demonstrate the lack of antigenic competition between CEA and MUC-1 in the ability to activate T cells employing the rF-CEA/MUC/TRICOM vector. Studies were then undertaken to determine if human T cells could be established from PBMCs using autologous DCs infected with rF-CEA/MUC/TRICOM and/or rV-CEA/MUC/TRICOM as APC.

After three IVS, as described in the Materials and Methods section, resultant T cells were analyzed for their ability to be activated by DCs pulsed with peptides or infected with vector. As seen in Table 13, neither of the T cell lines established using rV-CEA/MUC/TRICOM- or rF-CEA/MUC/TRICOM-infected DCs as APC could be activated to produce IFN-γ, when stimulated by uninfected 20 DCs, or DCs infected with FP-WT. These results are consistent with previous observations in the murine system that there is no cross-reactivity in terms of T-cell epitopes between vaccinia virus and fowlpox (Hodge J W, Poole D J, Aarts W M, et al. Modified vaccinia virus ankara recombinants are as potent as vaccinia recombinants in diversified prime and boost vaccine regimens to elicit therapeutic antitumor responses. Cancer Res 2003; 63:7942-9); it is also consistent with previous murine and human studies (unpublished data), which showed it is difficult to generate mammalian T cells directed against fowlpox epitopes. On the other hand, the T-cell lines generated with rV-CEA/MUC/TRICOM- or rF-CEA/MUC/TRICOM-infected APC were both activated to produce IFN-γ when using as APC DCs pulsed with either the CEA or the MUC-1 peptides (Table 13). These results may indicate that DCs infected with either vector will generate T cells from PBMCs that are directed against both the CEA and MUC-1 antigens.

T cells generated by DCs infected with either rV-CEA/MUC/TRICOM or rF-CEA/MUC/TRICOM produced IFN-γ when exposed to DCs infected with rF-CEA/MUC/TRICOM. In additional experiments, T cells were generated initially employing rF-CEA/MUC/TRICOM-infected DCs as APC, and were then passaged with CEA peptide pulsed APC for two IVS. As seen from Table 13, these T cells lost their ability to be activated by DCs pulsed with the MUC-1 peptide, but retained their ability to be activated to produce IFN-γ by DCs pulsed with the CEA peptide. Conversely, when T cells generated initially using rF-CEA/MUC/TRICOM-infected DCs were then passaged in the presence of DCs pulsed with MUC-1 peptide, they lost their ability to be activated by DCs pulsed with CEA peptide, but retained their ability to be activated by MUC-1 peptide.

Studies were then conducted to determine if T-cell lines, established using as APC DCs infected with either the rV-CEA/MUC/TRICOM or rF-CEA/MUC/TRICOM vector, could lyse human target cells. As seen in Table 14, both T-cell lines were unable to lyse CIR-A2 cells, but could lyse C1R-A2 cells pulsed with either the CEA peptide or the MUC-1 peptide. Neither T-cell line could lyse C1R-A2 cells pulsed with the control PSA peptide. On the other hand, the T-cell line established using DCs infected with rF-CEA/MUC/TRICOM, and then passaged using as APC, CEA peptide-pulsed DCs, was able to lyse target cells pulsed with the CEA peptide but not target cells pulsed with MUC-1 or PSA peptides. Conversely, the T-cell line established using DCs infected with rF-CEA/MUC/TRICOM, and then passaged using as APC, MUC-1 peptide-pulsed DCs, was able to lyse target cells pulsed with the MUC-1 peptide but not target cells pulsed with CEA or PSA peptides.

Studies were then conducted to determine if the T-cell lines generated using DCs infected with rV-CEA/MUC/TRICOM or rF-CEA/MUC/TRICOM vectors had the ability to lyse human tumor cells expressing either native CEA or native MUC-1. Three HLA-A2+ target cell lines were evaluated: the MCF-7 human breast carcinoma line, which is positive for MUC-1 and negative for CEA; the human colon carcinoma cell line SW1463, which is positive for both CEA and MUC-1; and the SK-Mel-24 human melanoma line, which is negative for both MUC-1 and CEA expression. We were unable to identify an HLA-A2+ cell line that was negative for MUC-1 and positive for CEA. As seen in Table 14, the T-cell lines generated using DCs infected with rV-CEA/MUC/TRICOM or rF-CEA/MUC/TRICOM both were able to lyse the breast and colon carcinoma lines, but were unable to lyse the melanoma line.

On the other hand, the T-cell line generated using DCs infected with rF-CEA/MUC/TRICOM and then restimulated with DCs pulsed with the CEA peptide for two IVS was able to lyse the CEA positive/MUC-1 positive colon carcinoma line, but was unable to lyse the CEA negative/MUC-1 positive breast cancer line and the CEA negative/MUC-1 negative melanoma line. The T-cell line generated using DCs infected with rF-CEA/MUC/TRICOM and then restimulated with DCs pulsed with the MUC-1 peptide for two IVS was able to lyse both the colon and breast cell lines, but not the melanoma line. Collectively, these data may demonstrate that both recombinant vaccinia and avipox vectors can be constructed to each faithfully express five human transgenes, and that no antigenic competition is observed in the ability of these vectors to activate human T cells directed against two human tumor-associated antigens.

The T-rV, T-rF, T-rF(CEA) and T-rF(MUC) T-cell lines were generated from an apparently healthy individual. All four cell lines were shown to be >97% CD8 positive, <2% CD56 positive, >75% CD45RA positive, and >81% CD27 positive. Studies were then conducted to determine whether specific T-cell lines could be derived from a patient with pancreatic cancer (patient 55). A T-cell line was generated using rF-CEA/MUC/TRICOM-infected DCs as APC, and was designated T-55. As determined by flow cytometric analysis, the T-55 cell line was 99.9% CD8 positive, <2% CD56 positive, 73.6% CD45RA positive and 87% CD27 positive. As seen in Table 15, this T cell line was shown to produce IFN-γ when stimulated with autologous DCs infected with rF-CEA/MUC/TRICOM and DCs pulsed with either the CEA peptide or the MUC-1 peptide, but not the PSA-3 peptide.

Studies were then conducted to determine whether 23 this T-cell line could lyse CEA and/or MUC-1 positive and HLA-A2 positive cancer cell lines. The melanoma cell line SK-Mel-24 (MUC-1 negative, CEA negative and HLA-A2 positive) was used as a negative control. As seen in Table 16, the T-55 cell line showed lysis of the C1R-A2 cells pulsed with CEA peptide and MUC-1 peptide, but not PSA-3 peptide. In addition, the T-55 cell line lysed MCF-7 cells and SW1463 cells at various E:T ratios, but showed no lysis of the melanoma cell line. Two additional T-cell lines were established from colon carcinoma patients. These T-cell lines were designated T-41 and T-49. The T-41 cell line was 98.8% CD8 positive, <1% CD56 positive, 33.6% CD45RA positive and 96.8% CD27 positive. The T-49 cell line was 98.9% CD8 positive, <1% CD56 positive, 29.8% CD45RA positive and 95.3% CD27 positive. As seen in Table 15, both T-41 and T-49 cell lines were shown to produced IFN-γ when stimulated with autologous DCs infected with rF-CEA/MUC/TRICOM and DCs pulsed with either the CEA peptide or the MUC-1 peptide, but not the PSA-3 peptide. As seen in Table 17, both T-41 and T-49 cell lines showed lysis of MCF-7 and SW1463 at various E:T ratios, but showed no lysis of the SK-Mel-24 cell line.

Two of the major concerns in the development and use of vaccines for cancer therapy are: (a) the poor immunogenicity of tumor-associated antigens and (b) antigenic heterogeneity of tumors. The vectors described here were developed to address both these issues. These vectors are the first in which five complete transgenes are inserted into an avipox vector and, to our knowledge, any replication incompetent vector. A parallel five transgene construct recombinant vaccinia virus has also been developed. For both vectors, each transgene was driven by its own promoter. Previous studies in both preclinical models and clinical trials have demonstrated that diversified prime and boost vaccine regimens using two different vaccines are superior to the continued use of one vaccine. It is for this reason that both the recombinant vaccinia and recombinant fowlpox vectors were developed.

As demonstrated in Tables 12-17, infection of DCs with the rV-CEA/MUC/TRICOM or rF-CEA/MUC/TRICOM vector resulted in the activation of T cells as efficiently as the use of DCs as APC that were infected with either CEA-TRICOM or MUC-1-TRICOM vectors. Moreover, T cells generated using DCs infected with rV-CEA/MUC/TRICOM or rF-CEA/MUC/TRICOM were able to lyse target cells expressing either CEA or MUC-1.

TABLE 11

Production of IFN-γ by CEA-specific and MUC-1-specific T-cell lines stimulated with rF-CEA/MUC/TRICOM

| | IFN-γ (pg/ml) | |
| --- | --- | --- |
| Treatment of dendritic cells | CEA-specific CTL | MUC-1-specific CTL |
| Uninfected | <15 | <15 |
| FP-WT | <15 | <15 |
| Uninfected + CEA peptide | 772 | <15 |
| Uninfected + MUC-1 peptide | <15 | 458 |
| FP-WT + CEA peptide | 689 | <15 |
| FP-WT + MUC-1 peptide | <15 | 404 |
| rF-CEA(6D)-TRICOM | 475 | <15 |
| rF-MUC-1-TRICOM | <15 | 298 |
| rF-CEA/MUC/TRICOM | 455 | 278 |

CEA-specific T cells (V8T) and MUC-1-specific T cells (T-1191-P93L) were stimulated with autologous uninfected DCs alone or pulsed with either the CEA peptide (CAP1-6D) or the MUC-1 peptide (P-93L); DCs infected with the control vector FP-WT alone or pulsed with either the CEA or MUC-1 peptides; DCs infected with rF-CEA/MUC/TRICOM, rF-CEA(6D)-TRICOM or rF-MUC-1/TRICOM. Peptides were used at a concentration of 25 μg/ml. The effector-to-APC ratio was 10:1. Twenty-four hour culture supernatants werecollected and screened for the production of IFN-γ.

TABLE 12

Production of IFN-γ by CEA-specific and MUC-1-specific T-cell lines stimulated with rV-CEA/MUC/TRICOM

| | IFN-γ (pg/ml) | |
| --- | --- | --- |
| Treatment of dendritic cells | CEA-specific CTL | MUC-1-specific CTL |
| Uninfected | <15 | <15 |
| V-WT | <15 | <15 |
| Uninfected + CEA peptide | 820 | <15 |
| Uninfected + MUC-1 peptide | <15 | 550 |
| V-WT + CEA peptide | 720 | <15 |
| V-WT + MUC-1 peptide | <15 | 358 |
| rV-CEA(6D)-TRICOM | 384 | <15 |
| rV-MUC-1 + rV-TRICOM | <15 | 213 |
| rV-CEA/MUC/TRICOM | 285 | 256 |

CEA-specific T cells (V8T) and MUC-1-specific T cells (T-1191-P93L) were stimulated with autologous uninfected DCs alone or pulsed with either the CEA peptide (CAP1-6D) or the MUC-1 peptide (P-93L); DCs infected with the control vector V-WT alone or pulsed with either the CEA or MUC-1 peptides; DCs infected with rV--CEA/MUC/TRICOM, rV-CEA(6D)-TRICOM or rV-MUC-1 plus rV-TRICOM. Peptides were used at a concentration of 25 μg/ml. The effector-to-APC ratio was 10:1. Twenty-four hour culture supernatants were collected and screened for the production of IFN-γ.

TABLE 13

Production of IFN-γ by CEA- and MUC-1-specific T cells established by using rV-CEA/MUC/TRICOM or rF-CEA/MUC/TRICOM vectors

| | Dendritic cells used as APC | | | | |
| --- | --- | --- | --- | --- | --- |
| T-cell line | Uninfected | FP-WT | rF-CEA/MUC/TRICOM | Uninfected + CEA peptide | Uninfected + MUC-1 peptide |
| T-rV | <15.6 | <15.6 | >1,000 | 976.3 | 514.0 |
| T-rF | <15.6 | <15.6 | >1,000 | 550.0 | 446.0 |
| T-rF(CEA) | <15.6 | <15.6 | 403.9 | 729.2 | <15.6 |
| T-rF(MUC) | <5.6 | <15.6 | 381.4 | <15.6 | 626.8 |

Human T-cell lines T-rV, T-rF, T-rF(CEA) and T-rF(MUC) were generated as described in the Materials and Methods section. These T-cell lines were stimulated with autologous uninfected DCs alone or pulsed with either the CEA or MUC-1 peptide, DCs infected with the control vector FP-WT, and DCs infected with rF-CEA/IMUC/TRICOM. Peptides were used at a concentration of 25 μg/ml; the effector-to-APC ratio was 10:1. Twenty-four hour culture supernatants were collected and screened for the secretion of IFN-γ.

TABLE 14

Ability of T-cell lines established by using DCs infected with rV-CEA/MUC/TRICOM and rF-CEA/MUC/TRICOM as APC, to lyse human tumor cells

| | C1R-A2 cells pulsed with | | | | | | |
| --- | --- | --- | --- | --- | --- | --- | --- |
| T-cell line | No Peptide | CEA peptide' | MUC-1 peptide | PSA peptide | MCF-7 | SW1463 | SK-Mel-24 |
| T-rV | −2.1 (1.26) | 57.9 (4.5)$^a$ | 50.0 (1.3)$^a$ | 0.6 (2.4) | 34.4 (0.1)$^b$ | 27.8 (0.5)$^b$ | 1.6 (1.1) |
| T-rF | 3.58 (3.9) | 62.0 (4.6)$^a$ | 59.7 (0.8)$^a$ | 3.8 (0.2) | 31.0 (2.4)$^b$ | 25.6 (1.2)$^b$ | 2.7 (2.0) |
| T-rF(CEA) | 4.3 (1.6) | 62.8 (1.9)$^a$ | −1.9 (1.0) | 2.7 (1.0) | 4.2 (3.2) | 32.3 (2.1)$^b$ | 0.6 (3.5) |
| T-rF(MUC) | −1.6 (3.2) | −3.6 (5.5) | 46.4 (3.3)$^a$ | 1.4 (4.5) | 38.2 (1.3)$^b$ | 25.2 (1.3)$^b$ | 0.1 (1.1) |

Results are expressed in % lysis (SD). The human T-cell lines T-rV, T-rF, T-rF(CEA) and T-rF(MUC) were established as described in the Materials and Methods section. A 6-hour $^{111}$In release assay was performed on C1R-A2 cells and a 16-hour $^{111}$In release assay was performed on MCF-7, SW1463 and SK-Mel-24 cells. CEA peptide (CAP1-6D), MUC-1 peptide (P-93L), and PSA peptide (PSA-3) were used at a concentration of 25 μg/ml. MCF-7 (human breast carcinoma cell line: HLA-A2+, MUC-1-positive and CEA-negative); SW1463 (colon carcinoma cell line: HLA-A2+, MUC-1 positive and CEA positive); SK-Mel-24 (human melanoma cell line: HLA-A2+, MUC-1 negative, CEA negative). The effector-to-target ratio was 25:1.

$^a$Statistical significance (P < 0.01, two-tailed t test) when comparing lysis to C1R-A2 cells.

$^b$Statistical significance (P < 0.01, two-tailed t test) when comparing lysis to SK-Mel-24 cells.

TABLE 15

Establishment of T-cell lines from cancer patients using rF-CEA/MUC/TRICOM-infected autologous DCs demonstrates reactivity to both CEA and MUC-1 epitopes

| | Dendritic cells used as APC | | | | | |
| --- | --- | --- | --- | --- | --- | --- |
| T-cell line | Uninfected | FP-WT | rF-CEA/MUC1/TRICOM | Uninfected + CEA peptide | Uninfected + MUC-1 peptide | Uninfected + PSA peptide |
| T-55 | <15.6 | <15.6 | >1,000 | >1,000 | 985.8 | <15.6 |
| T-49 | <15.6 | <15.6 | >1,000 | 974.2 | 819.0 | <15.6 |
| T-41 | <15.6 | <15.6 | 846.4 | 933.4 | 745.0 | <15.6 |

T-55, T-49 and T-41 were established by stimulating T cells isolated from a pancreatic cancer patient (#55) and colon carcinoma patients (#49 and #41) with autologous DCs infected with rF-CEA/MUC/TRICOM (40 MOI), for three IVS. The effector-to-APC ratio was 10:1. Peptides were used at a concentration of 25 μg/ml. Twenty-four hour culture supernatants were collected and screened for the secretion of IFN-γ. Results are expressed in pg/ml of IFN-γ.

TABLE 16

Ability of a T-cell line (T-55) established from a pancreatic patient
using rF-CEA/MUC/TRICOM-infected DCs as APC, to lyse human tumor cells

| Effector: Target | C1R-A2 cells pulsed with | | | MCF-7 | SW1463 | SK-Mel-24 |
|---|---|---|---|---|---|---|
| | No peptide | CEA Peptide[a] | MUC-1 peptide | PSA peptide | | | |

| Effector: Target | No peptide | CEA Peptide[a] | MUC-1 peptide | PSA peptide | MCF-7 | SW1463 | SK-Mel-24 |
|---|---|---|---|---|---|---|---|
| 50:1 | 0 (0.6) | 52.4 (3.3)[a] | 53.3 (0.4)[a] | 0 (0.1) | 23.8 (1.2)[b] | 24.1 (1.2)[b] | 0.5 (0.2) |
| 25:1 | 0 (0.9) | 30.3 (1.3)[a] | 34.4 (0.8)[a] | 0.6 (0.5) | 20.4 (1.1)[b] | 17.6 (0.3)[b] | 0.4 (0.3) |
| 12.5:1 | 0 (0.2) | 16.4 (1.8)[a] | 26.2 (5.0)[a] | 0 (0.2) | 13.8 (1.2)[b] | 15.2 (0.4)[b] | 0 (0.3) |

A 6-hour $^{111}$In release assay was performed on C1R-A2 cells and a 16-hour $^{111}$In release assay was performed on MCF-7, SW1463 and SK-Mel-24 cells. Results are expressed in % lysis (SD). CEA peptide (CAP1-6D), MUC-1 peptide (P-93L), and PSA peptide (PSA-3) were all used at a concentration of 25 μg/ml. MCF-7 (human breast carcinoma cell line: HLA-A2+, MUC-1-positive and CEA-negative); SW1463 (colon carcinoma cell line: HLA-A2+, MUC-1 positive and CEA positive); SK-Mel-24 (human melanoma cell line: HLA-A2+, MUC-1 negative, CEA negative).
T-55 was established by stimulating T cells isolated from a pancreatic patient (#55) with autologous DCs infected with rF-CEA/MUC/TRICOM (40 MOI) for three IVS.
[a]Statistical significance (P < 0.01, two-tailed t test) when comparing lysis to C1R-A2 cells.
[b]Statistical significance (P < 0.01, two-tailed t test) when comparing lysis to SK-Mel-24 cells.

TABLE 17

Ability of T-cell lines (T-49 and T-41) established
from colon carcinoma patients using rF-CEA/MUC/TRICOM-
infected DCs as APC, to lyse human tumor cells

| T-cell lines | | MCF-7 | SW1463 | SK-Mel-24 |
|---|---|---|---|---|
| T-49 | 40:1 | 20.6 (0.9)[a] | 42.9 (1.9)[a] | 0.8 (0.1) |
| | 20:1 | 12.0 (1.6)[a] | 30.2 (0.3)[a] | 0.2 (0.2) |
| | 10:1 | 6.7 (1.0) | 21.9 (2.1)[a] | 1.9 (0.8) |
| T-41 | 40:1 | 24.4 (1.6)[a] | 33.4 (1.3)[a] | 0.9 (0.3) |
| | 20:1 | 20.5 (1.2)[a] | 26.1 (1.1)[a] | 1.2 (0.5) |
| | 10:1 | 11.0 (2.0)[a] | 20.1 (0.1)[a] | 2.0 (0.2) |

T-49 and T-41 cell lines were established by stimulating T cells isolated from colon carcinoma patients (#49 and #41) with autologous DCs infected with rF-CEA/MUC/TRICOM (40 MOI), for three IVS. A 16-hour $^{111}$In release assay was performed on MCF-7, SW1463 and SK-Mel-24 cells. Results are expressed in % lysis (SD). MCF-7 (human breast carcinoma cell line: HLA-A2+, MUC-1-positive and CEA-negative); SW1463 (colon carcinoma cell line: HLA-A2+, MUC-1 positive and CEA positive); SK-Mel-24 (human melanoma cell line: HLA-A2+, MUC-1 negative, CEA negative).
[a]Statistical significance (P < 0.01, two-tailed t test) when comparing lysis to SK-Mel-24 cells.

All documents mentioned herein are incorporated herein by reference.

The foregoing description is illustrative thereof, and it will be understood that variations and modifications can be effected without departing from the scope or spirit of the invention as set forth in the following claims.

What is claimed is:

1. An isolated nucleic acid molecule consisting of a nucleic acid sequence that encodes an agonist polypeptide up to 12 amino acids in length comprising the amino acid sequence of SEQ ID NO: 14, 15, 16, 17, 18, or 19.

2. The nucleic acid molecule of claim 1, wherein the agonist polypeptide comprises the amino acid sequence of SEQ ID NO: 19.

3. The nucleic acid molecule of claim 1, wherein the agonist polypeptide comprises the amino acid sequence of SEQ ID NO: 14.

4. The nucleic acid molecule of claim 1, wherein the agonist polypeptide comprises the amino acid sequence of SEQ ID NO: 15.

5. The nucleic acid molecule of claim 1, wherein the agonist polypeptide comprises the amino acid sequence of SEQ ID NO: 16.

6. The nucleic acid molecule of claim 1, wherein the agonist polypeptide comprises the amino acid sequence of SEQ ID NO: 17.

7. The nucleic acid molecule of claim 1, wherein the agonist polypeptide comprises the amino acid sequence of SEQ ID NO: 18.

8. An isolated nucleic acid vector comprising one or more nucleic acid molecules consisting of a nucleic acid sequence encoding a polypeptide up to 12 amino acids in length comprising the amino acid sequence of SEQ ID NO: 1, 14, 15, 16, 17, 18 or 19, wherein the nucleic acid sequence is operably linked to an inducible promoter.

9. The nucleic acid vector of claim 8, wherein the vector is a viral vector.

10. The nucleic acid vector of claim 8, wherein the vector is a plasmid.

11. The nucleic acid vector of claim 8, wherein the inducible promoter is tissue specific.

12. A recombinant vector comprising a nucleic acid molecule consisting of a nucleic acid sequence encoding a polypeptide up to 12 amino acids in length comprising the amino acid sequence of SEQ ID NO: 1, 14, 15, 16, 17, 18 or 19.

13. A host cell comprising the vector of claim 8.

14. A host cell comprising the vector of claim 12.

15. The nucleic acid molecule of claim 1, wherein the nucleic acid sequence comprises SEQ ID NO: 21, 33, 34, 35, 36, or 37.

16. A method for generating an immune response to a MUC-1 tumor antigen in a subject comprising administering to the subject at least one nucleic acid molecule of claim 1 in a therapeutically effective dose sufficient to generate a cellular immune response in the subject.

17. A method for generating an immune response to a MUC-1 tumor antigen in a subject comprising administering to the subject the vector of claim 8.

18. The method of claim 17, wherein the polypeptide comprises the amino acid sequence of SEQ ID NO: 19.

19. The method of claim 18, wherein an immune response is generated against a MUC-1 tumor.

20. The method of claim 16, wherein the immune response is a cytotoxic T cell response.

21. A method for treating a subject suffering from a MUC-1 tumor comprising:
    isolating dendritic cells from a subject suffering from cancer;
    transducing the dendritic cells with the recombinant vector of claim 12, and
    administering the transduced dendritic cells to the subject, such that the subject is treated.

22. A method for generating an immune response to a MUC-1 tumor antigen in a subject comprising administering to the subject the recombinant vector of claim 12.

* * * * *